United States Patent
Yoon et al.

(10) Patent No.: US 10,227,570 B2
(45) Date of Patent: Mar. 12, 2019

(54) *LACTOBACILLUS BREVIS* BACTERIOPHAGE LAC-BRP-1 AND USE THEREOF FOR INHIBITING *LACTOBACILLUS BREVIS* PROLIFERATION

(71) Applicant: Intron Biotechnology, Inc., Gyeonggi-do (KR)

(72) Inventors: Seong Jun Yoon, Seoul (KR); Sang Hyeon Kang, Seoul (KR); Soo Youn Jun, Seoul (KR); Jee Soo Son, Seoul (KR); Hyoun Rok Paik, Incheon (KR); Byung Kuk Kim, Gyeonggi-do (KR)

(73) Assignee: INTRON BIOTECHNOLOGY, INC., Gyeonggi-Do (KR)

( * ) Notice: Subject to any disclaimer, the term of this patent is extended or adjusted under 35 U.S.C. 154(b) by 0 days.

(21) Appl. No.: 15/543,634

(22) PCT Filed: Jan. 5, 2016

(86) PCT No.: PCT/KR2016/000029
§ 371 (c)(1),
(2) Date: Jul. 14, 2017

(87) PCT Pub. No.: WO2016/122127
PCT Pub. Date: Aug. 4, 2016

(65) Prior Publication Data
US 2017/0369852 A1 Dec. 28, 2017

(30) Foreign Application Priority Data
Jan. 28, 2015 (KR) .......................... 10-2015-0013453

(51) Int. Cl.
*A61K 48/00* (2006.01)
*C12N 7/00* (2006.01)
*C12P 7/06* (2006.01)
*A01N 63/00* (2006.01)

(52) U.S. Cl.
CPC ............... *C12N 7/00* (2013.01); *A01N 63/00* (2013.01); *C12P 7/06* (2013.01); *C12N 2795/10321* (2013.01); *C12N 2795/10331* (2013.01); *Y02E 50/17* (2013.01)

(58) Field of Classification Search
CPC ....................................................... C12N 7/00
See application file for complete search history.

(56) References Cited

U.S. PATENT DOCUMENTS

| 2009/0104157 A1 | 4/2009 | Solomon et al. |
| 2014/0273137 A1 | 9/2014 | Donovan et al. |

FOREIGN PATENT DOCUMENTS

| WO | WO-2016/122127 A1 | 8/2016 |
| WO | WO-2016/122128 A1 | 8/2016 |

OTHER PUBLICATIONS

Marco et al (International Dairy Journal vol. 39, pp. 64-70) (Year: 2014).*
Marco et al (Applied and Environmental Microbiology vol. 78 (24), pp. 8719-8734) (Year: 2012).*
Mahony et al (Virology vol. 434, pp. 143-150) (Year: 2012).*
Fukao, M. et al. (2013) Genomic Analysis by Deep Sequencing of the Probiotic *Lactobacillus brevis* KB290 Harboring Nine Plasmids Reveals Genomic Stability. PLoS ONE. 8(3): e60521. https://doi.org/10.1371/journal.pone.0060521.
Kelly, D. et al. (2011) Isolation and Characterization of Bacteriophages the Inhibit Strains of *Pediococcus damnosus*, *Lactobacillus brevis*, and *Lactobacillus paraplantarum* that Cause Beer Spoilage. J Amer Soc Brewing Chemists. 69(1):8-12 (See abstract, pp. 9-12).
Lu, Z. et al. (2012) Bacteriophage Ecology in a Commercial Cucumber Fermentation. Appl Environ Microbiol. 78(24):8571-8.
NCBI, *Lactobacillus brevis* KB290 DNA, Complete Genome. GenBank accession No. AP012167.1 (Mar. 29, 2013).
Roach, D.R. et al. (2013) Bacteriophage-encoded Lytic Enzymes Control Growth of Contaminating Lactobacillus Found in Fuel Ethanol Fermentations. Biotechnol for Biofuels. 6:20 (inner pp. 1-11).
International Search Report dated Apr. 25, 2016 by the International Searching Authority for International Patent Application No. PCT/KR2016/000029, which was filed on Jan. 5, 2016 and published as WO 2016/122127 on Aug. 4, 2016 (Inventor—Yoon et al.; Applicant—Intron Biotechnology, Inc.) (Original—5 pages/Translation—3 pages).
Lu, Z. et al., Isolation and Characterization of a *Lactobacillus plantarum* Bacteriophage, ΦJL-1, from a Cucumber Fermentation. Int J Food Microbiol. 2003; 84(2):225-35.
NCBI, *Lactobacillus* phage ATCC 8014-B2, complete Genome. GenBank accession No. JX486088.1. 2012 (44 pages).
NCBI, *Lactobacillus plantarum* Bacteriophage LP65, Complete Genome. GenBank Accession No. AY682195.1. 2006 (66 pages).
Silva, J.B. et al., Bacteriophages as Antimicrobial Agents Against Bacterial Contaminants in Yeast Fermentation Processes. Biotechnol Biofuels. 2014; 7:123 (inner pp. 1-11; See abstract, pp. 3-8).
International Search Report dated Apr. 25, 2016 by the International Searching Authority for International Patent Application No. PCT/KR2016/000030, which was filed on Jan. 5, 2016 and published as WO 2016/122128on Aug. 4, 2016 (Inventor—Yoon et al.; Applicant—Intron Biotechnology, Inc.) (Original—5 pages/Translation—3 pages).
Non-Final Office Action dated Jun. 14, 2018 by the U.S. Patent and Trademark Office for U.S. Appl. No. 15/543,723, filed Jul. 14, 2017 and published as US 2018/0119109 on May 3, 2018 (Inventor—Yoon et al.; Applicant—Intron Biotechnology, Inc.; (8 pages).

(Continued)

*Primary Examiner* — Albert M Navarro
(74) *Attorney, Agent, or Firm* — Ballard Spahr LLP

(57) ABSTRACT

The present invention relates to a Siphoviridae bacteriophage Lac-BRP-1 that is isolated from the nature and can kill *Lactobacillus brevis* cells specifically, which has a genome represented by the nucleotide sequence of SEQ. ID. NO: 1 (Accession NO: KCTC 12659BP), and a method for preventing and treating the contaminations of *Lactobacillus brevis* by using the composition comprising the bacteriophage as an active ingredient.

2 Claims, 2 Drawing Sheets
Specification includes a Sequence Listing.

(56) References Cited

OTHER PUBLICATIONS

U.S. Appl. No. 15/543,723 (2018/0119109), filed Jul. 14, 2017 (May 3, 2018), Seong Jun Yoon (Intron Biotechnol., Inc.).
10-2015-0013453 (10-1679548), Jan. 28, 2015 (Dec. 6, 2016) Seong Jun Yoon (Intron Biotechnol., Inc.).
PCT/KR2016/000029 (WO 2016/122127), Jan. 5, 2016 (Aug. 4, 2016), Seong Jun Yoon (Intron Biotechnol., Inc.).
10-2015-0014188 (10-1678549), Jan. 29, 2015 (Dec. 6, 2016), Seong Jun Yoon (Intron Biotechnol., Inc.).
PCT/KR2016/000030 (WO 2016/122128), Jan. 5, 2016 (Aug. 4, 2016), Seong Jun Yoon (Intron Biotechnol., Inc.).

\* cited by examiner

SEQUENCE LISTING

<160> NUMBER OF SEQ ID NOS: 1

<210> SEQ ID NO 1
<211> LENGTH: 136174
<212> TYPE: DNA
<213> ORGANISM: Bacteriophage Lac-BRP-1

<400> SEQUENCE: 1

```
aataataata ataataatac gttacctcta ttttgacagg agttctggtg cctaactttg      60
acaactcaat taatatatct aattggcttt caccatgctt caattaacct cggcatatat     120
tcagtcaaac tctcaggaag tctgagctac aagaagctat ctcataactt cttcctgcgt     180
tataaagagc tatcagtctc aatggactat atgatggaca caaacattca gattgtattt     240
tagagtaatt gaattcattt tcaatgtctt gtactgccgt aacgttgtgc ctattcaact     300
ggtaagtata agctaactgg tcacccagta ttctcggcat aatcgaactt ttagcatttc     360
tagcgttaag taatagtgca acctattcct gatactagat tcttagccat ctgactcgtc     420
tattatattc gacctttctt accatacctt tataccacag tctatccaca cctatcttat     480
tgctaagata aacatcctag ctccctgtat attattatat aggaattcca catgtataag     540
tatccttgta catgtattat atcaagataa gcccactgca atttgttcaa aaatcttcac     600
gtggttatta gatatattaa ttcagttgtc aagaactat tttctatata ttaattataa     660
cacattttaa catattatac aacactttcg ttaaatattt aattcttttt gtttcttgta     720
gagagatgtt tgcacaccct tagcccactc agagtgatgt tcttctctaa taacctgacc     780
taactcaata cattctttaa tgctatctgc atcttttgta tcaaattcat acccatcaaa     840
aacatcgtac attaaaacgg acttcttaat acccagacga acctgttctt cttctgtacc     900
tactacagat aagtctgcat agtatacatt aataccgaat tcaactgagt catctaagtt     960
ttgaatagta tattcattat ccacataatt ttctttaatt tcccaatgct ttgggttaaa    1020
tccttctttt agaagtaagt gtacaacaac tgtttttgca agttctaatt cttccactat    1080
aaaggcccct tttctaggta tgcataattt ctgtaaacag tctctgctgg aatcgaacca    1140
acgtcttaag ttttggagac ttttattcta ccgctgaaat aagagactaa aaatacgcgc    1200
acgttgtttc caatggtacc ttatcgtact ccgtacatgc ccgctcttaa tattcattac    1260
aaacattaag cgtacttaat taaaagtata tggtgaaagc tggattcgaa ccaacgctgt    1320
tataggtttg aactatatca tttactagta tactatagtt cctaactaaa ttgagaacat    1380
gaacacggtc atctgaccgc cgcactacct ttatgctatt tcaccaaatt gcaaccatat    1440
aaccttagaa gtaaggttgc tttgcggagt gtcttaccct tgaacaagca cacaatctct    1500
ttacgcgatg atatacgtcc gctacttttt gtctagttta agcttgttta attatgctag    1560
acctacagga gacaagtttc ctttatttac cagaagctat ctggatgggt caaccgggac    1620
ccgattgcgg taatgggagt cgaacccaat atttataggt tatgagccta tcgtgattgt    1680
tccgtttcac tctaccgcat atcaggatag ctggatttga accagcgact tctcgcttac    1740
ttgtagtcct ttgtatgtgt cggaatgtta tatttttcac accatttttct tattcctttt    1800 cctgttcttc catacatcct tccaacagcc tcaaagtttt tagtacttt tatggcacat    1860 aataattctt ccttggatat aggaacaggt ttagtcctat ttatgcaagc acacttacga    1920
gaacagcata tttgttctct atccttttta ataatactt tatgacatac tggacaagtt    1980
gcttgttcat tagttctcct tggccttta cttctatgac cattttgtt tccataagta    2040 gatgtttgag agtgacaatt aggacatagc catctaagat tctcttttgt attgttagtg    2100
```

```
tagtctccat ctatatggtc tatttgtagg gttaaaggtt tattattcca gttaccgcct    2160
attccacaaa ttgaacattt ataatccata tagttatctt taaatacccg tctccgtata    2220
ttacagtatt tggaacctct aatgtatact tcactgtctg gaacagaatt ttcttgtatc    2280
tgtttatttc tgtttacact aatgcctaat tccttcatac gctttttaa tgggtttgct     2340 tgagacatcg aagagtatcc aatagtactt aatacctctt tgagcgatgt agacttacta    2400
acaattttct ttaactctcg gtctgaaaca ctgtctaata actttatagt atcatctcac    2460
ataaataatt ttactctttta ggcaatgccc ctagtaggag tcgaacctac acggtattac   2520
taccacaagg ttctaaacct tgtatgccta ccaattacat cataggggca tatatggcga    2580
atttcggatt caaaccgaat ttattccggg tcacgtttta atggttgcaa ccccggcgc     2640 tctaatctat aagctaatcc gcctatgctc ctgacaggac tcgaacctgc gacctcctgc    2700
ttacaaagca gatgctctac ccaactgagc tactggagct aactatcata tgtaccctat    2760
cggactcgaa ccgatgaccg atggattaga atccattgc tctatccaac tgagctaaga    2820
gtacctaata tagattaatt tctctatcaa tctatactta tagtatacca cgttttattg    2880
attaatcaag gattatttaa aattattttt atacgttgta aattgctttc aaattatcgc    2940
tactatactc cataatttga agtttatgat tagccattgt atacccattc tcttcctcat    3000
atgggtcatt taacttaggt gttccaaatt gacgtgtaac tactccatag tcatcattag    3060
ttacctcttt atgataatga ccataatgaa tttctctata cttagcatta ctccactcaa    3120
caggattttc agttgcaaat aacattggaa gtttcttttg tgccttatcc ccgtgagcca    3180
gtaaaatact tacagagcct aaagtaaagc actgacggta atgtgaagta ttgtgaactt    3240
caatctgagg gaatctatct gaaatagcat caataaacat gtagcttaaa tcaaaatcat    3300
gatttccccc tacagaatat aagtatacac tatttgagtt cagcaaagaa aattcaatta    3360
aatcatcata aaatctttta gcgtctgaaa tagccttaat catattaaca tggtctaatt    3420
gagttccttt aaccgtcata gtcttattga cataatctga gtgaaataaa tcaccgccat    3480
tttcaattac aatttttatca taacctcgac taataaattc ttttacctga tttaaatgcg    3540
ttaacatatt ttcataattc ataatgccga aatgtaaatc aaataaggga attactaaat    3600 tattttacc tgatttaatt gtattaactg ttttcgattt aatttcttta ttaaagattt      3660
tagaaaattc tttaggtgta actacatact taggtttaac actaattta gtttgataag      3720 aagttactcc ctcggactgt ttccaaaagt tacttacatt actaacaatt tcccattctt     3780
ttggattata gtgatgtgct ttaagcaaat cctccggtgt aatatcatgg ccctctacaa     3840
cctctaaaat agtagtagat gtttgtacac catctctatt atatgtttcc ccagttgatt     3900
ggctacttga tttaaaggac atcggttcac ctacagcctg tagtttacgc ctaacacttc     3960
tatctgaaac ctgtaatcct ttgttcttac ttaacttttc tgaaatttca tggctagata     4020
agcccttacc ttttaattta attgcataat caatttcatc ttggttccat tttgacatca     4080
gtcaattcag cccctaacat ttaataatat cttaattata ctctttttat ctttatatag     4140
ttaaaaagcc ctttaagggc tataaatcaa ttccgtgaaa ccatatccaa ttgagtattg     4200
ggaaatcata accaactaag ctacacccta aggatagaaa tagaggtatt ccaaaataaa     4260
aatgaaaaac taataatact agtgttccta taatatatcc aattatattt actcttttaa     4320
taaacttttc aaagctcatt tagtcacctt caataaccag aatgctttat ctctcaccca     4380
cggcttgtca taatttagat aatatccact agaggggtca aaccttttga agtcttcata    4440
```

```
gaatacggac ttcttgaagt cttctggata ctttttaatg agtctatcta agtcaaagct      4500
gagatggtcg tataaatcat cacctattag attttttattt aatttgtagt ataggtatgc      4560
atgtattaat acttgacgct ctcgttgatt taattcttat gaactacacc gtggttaaaa      4620
ccacgggttt ctaggaacac tgcatactta cacagcattc taggaatgta gtgcagaggt      4680
tacaactatt taccgcggtt cgttccaaac ctaattagtc tttttaagca tttagaatat      4740
tcttagcggc attaatatcc ctatcatggt gtataccaca attaggacaa gtccattgtc      4800
gaatatctaa agtatgcttt ccatcatcat atccgcagtt actgcaaatt tgagaggtct      4860
ttctaggatt aacagtgact aactgtttcc cataccactc gcatttgtat tctagttgag      4920
aacgcaaagc acgccaagat tgattagcaa tcgctcgagc aagtttgtga ttttttaagaa      4980 gatttttggt tttcaaatct tcaattttaa tcacatcata ttgctcgact aactgtttgg      5040
ttagattatg aagatagtta tttcgttgat tagcaatctt ttcactatat ttggctacca      5100
tatgcttagc tttaagatag ttcttaaaat cagatagttc tctaggttca ataaccttat      5160
tgtgtttatc ccaagcaatt tctttcatag cttgtaatcg tctacgagat aaccgtttct      5220
cccaataatg cttcttttta gctaaaagtt tatcaaaacg aatagtagga aatttaatgc      5280
catcactagt aatcattaag tccgctattc ccatatcaat tcctacggac tgattagttt      5340
tttgaagctt tttaacttcg gtatctacta agacaattgc atagaacttt ccagtagaag      5400
ataatctaat agttacattc ttaatcttac cttcaatctg acgaccggac ctaaagtaaa      5460
cagtacctag cttaggtaac ttaagtctat gttcaccaat ctgacaaata ttattgttag      5520
tgtatccaga ttgataactc tgcttaggaa acttacggga tttgaatttt ggatgaccgg      5580
agtgttcttt aaataatttc tgaaatgcct gattgaggtc acggctcaca tgctgtaaac      5640
tagttgattc tgcttgcttt aagaacgggt actcttgctt taagcattta atcagacgat      5700
tcatgccaaa ttcattaacg tatgaaccccc cattattata ccgttcaatc tgcatatcaa      5760
gcaactgatt ccagacaaat ctacagcatc caaaattgtt gactattttg tactgttgct      5820
caatactagg gtatatccta gttttgatag cttttaatgg cattatattc acctccttat      5880
atcttaattg tatcatactt tagaataata tgcaattcat cacgtaacta agtggcgag      5940 ttttctcccc taaattttaa taaatgttag ggtagtatct aaagtaatag gtcccccggt      6000
gaactgctcg ccacataagt aacgagcttc taggaacact acatgcttac acaacattat      6060
agggatgtag tgcagaggtt atagctattt tactaagggc cgttccggcc caatatagtc      6120 tttttatttgt taacttggtt ttcgttaaca actatagtat atctatattt gtcaatagat      6180
attcatttag aatagtccgg aattcatctc gtcactaaag tagcgagctt tctcccctca      6240
gttttgtaaa caggtacccct tatccagctt tacactttct tggtagtttt aagacatact      6300
ggtcatagta ttacttatta ttatcaattt tctcttgcat tctctttaac caaataggg      6360 attcttatc atttctagct tttaatcggc tagcaatatc atcatattcc ttcttatgct      6420
ccaaatattt attcttcatt accctatttg tttctcctaa ctcaccggaa taaatcccta      6480
aattgggtag cttcttgaaa taactaatag ttttagctaa ttcttatcc cgtttctttt      6540 tataagcctt agcttgttct tctgacatac caccaaggta gtaatcaaaa tagtccttaa      6600
tatctttatc taagttatca tagtcaatta acattattta cacatccaag tctttttata      6660
gtctatccaa gtatttctaa caaactcttc aaaagtatct tccttgaaaa tataatcgta      6720
ccaattataa tattttttct ttacaataat gtcagttcct atttaacat cattcatcat      6780 atcatctaaa gtataatgat aaggctttcc atctagggta taataacaat ctactgtata      6840
```

```
aattttatga attatggggc taaaaccatt actcttatac tcattataag acttactaat    6900
gtattttttt acgtctgata tgctataacg agaagcatat tcccaaatgt cccaattatc    6960
atacagtttt ttataaccac ctaaactcat aggaagacca tctgagtcac ctctatttat    7020
aaccctccta gtatgtctac tagctaattt ttttagctga tgcgctgatt ttccattctt    7080
taatactgga ttttttcggt aacttcttga cattctcatc acctacctaa ttttagaatg    7140
atataactaa caatatgtat taaaaatagc cccacctcat cgtatggata gggctatttt    7200
tattaatagt aagactctcc ctctagcctt actatatcaa ctaacaaagg tgcaataaaa    7260
agaactaata tcaccacatc tatagtatac cacaattaaa ttattttaaa agaattaaat    7320
tcctaaatat aatttattta ttttgtctac caattctttt ttagttacag gttccttatt    7380
cttaaactga taaagctcgt cattatgctt tggtttattt agaaacttaa gaattttatg    7440
cttcttaact tttttgacc tgaaagccat aacaacagta tcaaatacat aactatctgg    7500
caaattatca aagtaagtaa catttagtcc tgtgggatta cttaaatata aataaaagta    7560
accagaatct gttaacactt taaaatagtt taaatcgaca agttctaaac taaattcctt    7620
attattatcc aatactaaac acctcgaaca cgtgcttcat aatttagtgg aattaatcga    7680
ctagaattta acttattttt catcaactga tattcacctt tatagttacc ttctaataaa    7740 tcaattcat taaaatgata taagaaattt aaatcattag ttgggacata agaatcaatc    7800
caataagtta agtggttgaa tgagtatagt aaatcttttc taggcttaga actgatatta    7860
gtatcacctt taatacccga gttaataatt tcttccccta gagatttaac ataatctaat    7920
ccgctagcaa taaattttgg ttcactaact gcatatctag ctctaacacc atctgtagaa    7980
gttaaaccaa gctcaatctt accccgtctt gaaacacttt ctaggttatt aaagattttt    8040
ttataaacat cttggctaac gctttctgta ataacagaaa tactagcaga tgtccgacct    8100
acatacatat ctaaaacaat tgtataaatt cgttcatatg atttcttaat cttaatcacc    8160
tcgattatta actactattc cgtagtatta gtagggtctt cattattttc tgtttcatca    8220
ggttctttag ctgttagctt gtctacagca tcttctaatg tagatactct cttagtcata    8280
tctaacaaac gattattagt tttactaatt tctgtattat taaccttgta aacaccaaag    8340
gataccatca taattgtacc ttctgcggga atagaacgac catcttggaa tttaacatct    8400
accaaaggac cagaaacagg ttctaccaat ccatctaaag agaagattaa tcctaagtta    8460
acagcatccg ttagcaattt agttactctt gactgtgtat acccttaggg aattagagag    8520
ttgtctaaat gaactcttag agttacatta gttgagtctt tctccgaatc agaataaccc    8580
tctacatcta aactagaaaa atccaaaaca ttttcatcaa agtttcagc tacgtcaata    8640 ataaacttta attctcgtga attaaaccca taatcctcaa taggaacaac taaatctctt    8700
aaactaaatc ttttcatttt ttagtaccac ctttaataat tttgtataag agtattatat    8760
cacataatta cattggatta aaaaatccgc ccttgttatt atctaaagcg tcttttaaat    8820
cgctttccgt atatttgtta atagaattat tgcccccact taaactagta gattgaatac    8880
tattatctga gttatgaaga acatcgataa ttctattcat accaaccatg gcataaactg    8940
cggcttgaaa gaagtgtaat tagtacccct agtttcctag tatttaaaag ggtttagact    9000
atatcttaat cctactgttt ggtgtaggat tctctgcttt acttccctaa attaataagg    9060
ttttcttatc tagttctcac tattcccgtt tgaatagcta cctagaagtt tagtcgttag    9120
acctttacag ataattaaat tatctgattt agtacggtgg tcagctctat ccataactac    9180
```

```
ttggacttag cctttcttac cagtatattc gttattacta ctactgtagt tattattta    9240
ctttgcccgt ttaacagagt tttcgacaag gattactcct tgaaggaacc acttggttaa    9300
tccccttcct ttttacggga aatttcttta tgtgtcgtac cattatcatc ttcaacatca    9360
cgaataatga cattcttacc atgttgaata aacagtccta actctctgtc aacatgttta    9420
taaaacccaa tacgtcccat tttaatatga gtgattaata aagtattctg cattaattta    9480
tctaaagtaa ccttagaatt attttcatca aaatgagcat tcgggtcccc attagaacgt    9540
gcacttctaa caaatgctcc gtatactttt cctttgccaa aatacttaat cagtttatta    9600
acataattac cattataccc caagtctggg ataattatat caggttcata cgtgttgaga    9660
acggatacca ttctatgcag gtcggactca atattttcag ttcctgtaga agttggtatt    9720
ctaacgaatt taataaaatc ccaattcccg tcacctttca tgccaagtaa aactaaatgg    9780
tgataatgtg ttccccaatc tatgccagcc gctacataag cataaccatc acgagtatct    9840
ttaggctcag gtaaataatc tctacgattg ttaagaacat cttctttagt tactctaatc    9900
gtttcatctt gataagggta gcctaaagta tagttataaa agaactgtgg cgaggtttgt    9960
aaactatctt ggtatagttt atcagaagta agccaaacag cgttcatttg agagattaag   10020
taccctctcg aacgtgctga atctgtatac ttaggaaccc attccacatt ataccaacga   10080
gaagactcta aagacttacc gcaatattga caaacatatg ccgttgagcc aggtctaaca   10140
atattagcta ccctatctat tccatcttca tctaaaatct ttaagttctt ttcaaaattc   10200
ataacctgcc atttaccaca atggtcacat tttattgtcc aatatctttg gtctgattct   10260
ttaaacctag catcaatacc aaaatcacta gctgatgggg tactccaacg tctaattagt   10320
ccatatcgat tatcggactt tagggactcc ttgatagaag cttctgctgg ggtttccgca   10380
tatcgttcat actcatccat catagccata ttaatagcaa caccttcaac ttgtgcacta   10440
ccagaacctg aacggaaaaa tatacgtgaa tcccttattg acatttggtc cagagaattg   10500
ttatcaccat ttaataaact tctatagtaa tcacttttct caaattccgg cctaatacga   10560
gatttaacgt ggtcacgcat tctactgata gaagggaacg tgtatagaat actgacatta   10620
tcgaaagaaa aaacatctgc aaaatagatt aaagccataa ccccaacttc actaaaccccc  10680
agttgacgac ctttcatgat attaacttct tgcacattag ggtctactaa agactgtaag   10740
ggttcaattt gccaattacg gtgacctata gaacagagaag catcataatt tggaatatca  10800
aatgttactg gatgccccctt aaccttatga tgtttaagaa tataattaat tgggtctaac  10860
attgatatag catagtctaa tcttttccggt gtaatctctt taccaccata taaggacttt  10920
acataatttg ccaactgttt accgtccatg cttttccacc tttctaaaat tcattaccgt   10980
tgtctttgtt aagaatatca gcctgttctt tgactagttt agcaacatca tcttcgctca   11040
tattgtctaa tgacttttct agttcaacag gtttcggttt tgtgtcacca ggaagacctg   11100
cggtagaaga atataattta gctaaattaa tagatactgc ggggtgatta ctagttgatt   11160
ctccttcact agccagcatt tgaaaaatag agacaatatc tttaacgtcc ttaatatctc   11220
taaccttaat gctatcacta ttaacagcat ctactagttt tttgctaaga ataaaggccc   11280
cttttttctaa attagattta gttgtctttg aaatatctga tgtttcagga acatcactgt   11340
ccttgttgtt gttgacatac ttattcattt catcaaaataa actgctcact aacttgtcac   11400
cctttctttta taacgtaaat agcactcact agtattatag cacagtgaat aacgcatcaa   11460
ttcgtttgca cactggtaat atctaacatt tgctttccaa cttccattta catatgctga   11520
taatttttta ccacaaactg cacaaactct agctgttttg actaatccac tattacgact   11580
```

```
tattattttt gtatttttag agtcatttag aagattccgt cttttagta accatatgtt    11640
tttttcattc gacatgttgt ttacccctt attgttaata taattatata cccaattgag    11700
gtattttga ccaattaggg gactaaataa tactctaaaa tcgtcctctt aaattaggac    11760
atttcgtgac ctaattaagc ataatttaac aattttttat gtaattaaat taggacattt    11820
gttgccctaa ttaaaaataa atggattctt gttaatatca ttaactataa aataggaaaa    11880
aacatgtcct aatttaatcc ttactccgac aatgggtttg atgtgatttt tgaaaaaact    11940
tcgtcctatt gtttccctag agtatatata ttattattct ttactaagta attaagtaat    12000
aataaatata taataaatat acttagagaa attttttgat tcaaatcctg attatttta    12060
tcttttttca aatatatttt ctaatgattt ttcaaaaata atcatcaagt tcatttcaat    12120
atttttaaa atacactaac tgttttcaa aatattaatt atgcaaatat tacatttgta    12180
ataattgtt atatttatgt aataccttt gacacatcaa gtgttatact tactaagtaa    12240
gcaagaaaat aaaaatgtta aaagaaagg ttgattatta ttaatacgaa agtcaagagt    12300
cttatttag gagtatctgc attagttggt atgggggttg caatgacgac aacagcatca    12360
gctaatacaa aatacactgt taaatccgga gactctctat ggaaaatcgc taatgaacac    12420
ggaacaaacg tttctagttt agtaagtctt aaccaatcaa agttaacttc tggctctgct    12480
agttatattt atcccggaga tatttagaa gttggcaaga ctagcgcaaa tacttatact    12540
tacgctaata atcaaaacta taatgtccaa agctcagctg ggtatacaac caataccagt    12600
aatacaagta attattattac taatccacaa acgtctcaaa ataatacaac agtatcttct    12660
gtagggaatt ctaatgcttc tggttccacc tatagtcagt ttatccaagc aggtggtaca    12720
aaggctttat gggacgcaat tgttgttcct gaatccggtg gtaatccttc cgcatcaaat    12780
ggtcaatatc atggtttggg acaaacaaac caaagttggg gtagcggttc agttgcttca    12840
caaaccaaag gtatgattag ttatgctaat agccgttatg gctccgtagc aaatgctgta    12900
tcttatcgac aatcccacaa tatgtggtaa tatttttta aaagtaccgt ggtctaaata    12960
aggctatggt actttttttt atactttcac aatttgatat aatataacta tatgactaat    13020
ttaaaggcaa ccttatatta attaatagca acaaaacagt agaaaggagc tgattatttg    13080
ggaatttttg ataggtttaa cggcaagcca actatttcta gtggtgaaaa tataaataag    13140
gctattaatg atattgagag agactacgtt agtaagagta tgcacgccaa agccaaagca    13200
aataatgcta tttcagttgg ttcttttggat gttgatagta gtgactcaac tatggttgac    13260
aaaggttcta ttttgcaaca taaaaagtta cttagaataa aatcaacaaa tatcattgtt    13320
cagtcaatta ttagaacccg tactaatcaa gttgaaaagt attcaagacc tgctcgttat    13380
tcaagtgatg gggttggatt taaaattctc cctaaaaagc ttcccaagga tggtaagtta    13440
tctgctcaaa aattaaatag aattattgaa cttgaagaat ttattcaaaa ctctggtaat    13500
gtttggacag ctcagcgagg tggcgggttt cgtcaattct tatctgaatt tgtgtataat    13560
cggtatgtat atgaccaaat aaatgttgaa ctaattcgag atagtcaagg gaagttagac    13620
cattttaact ttgttgatgc tggtacagtc gtttttacatg acttacctaa aagtgcagat    13680
tcccctagaa gttttgacca atatccaaac gaaacacct ctaaaccaat tcattttaat    13740
gaaaatgaat taactttcgt tgtctataat gctttagccg atgttactag aagagggtat    13800
ggttattcag aagttgaagc ttctctaagt cattaagat tcattgatga cacgaggac    13860
tttaatgcta gattctttgc tcagggtggt actactcgcg gtttgctatt aattaattct    13920
```

```
ggttcttctg cggcacaaaa tacggcggga ctaaatagtc ttaggcagga atggcaatca    13980
agcttctctg gtacaaatgg tgcatggaag attccagttg tttccgcaga ggatgctaaa    14040
ttcatcaaca tgactcaaac atctaaagat atggagtttg aaaagtggtt taattttcta    14100
ctaaatattg ttagtgctat tttccaaatg caacctgatg aaattaactt ccctaatccg    14160
ggaggttcta ctggtaaggg tgctggtaat tccattaacg aaggttctac gcaaaaagct    14220
aagatgaaac agtctcaggg taaagggctt gaacctctat taaattatat tgaagacttt    14280
attaataaat atattttgcg tgagattgat gacgactatt actttagatt tactttaggt    14340
gatactaaag atgaattaca acaacaacaa gtaattaatc agaaacttaa aaatggaatg    14400
acacttaatg aagctcgtaa ggaattaggg ttggaacctt tagatagtga gattggagat    14460
ttgccgggag accccgcaac cgttgtacag tttatgcaat tgctaactaa tgaagataag    14520
gttgttcagc aggttaaaca gcactctaat gactacaatc cagacgcatc agataacggt    14580
aaaccggagg aaggtatgcc cgttgaatct gtaactgata ataatattag ctctgacgat    14640
agtaaaaatg tagataatga taatccagat tctaactaat ttgtgtgaat aatcatgata    14700
cctttatatt attatttaga taaaattaat tagtattagt ttggaggtgt taatttacat    14760
gaaagaaaat aaacttaata ttttcctacc tatcgatgct gaattaacag aaaaatcaaa    14820
taacaataga aatagtgata aagatgataa ttcagtaatc gttgccgggt gggcttcaac    14880
accaaagttt gattttcagg gggaaactgt tgacccttta ggaattgatg attcatattt    14940
taaagaccaa ggttggatag attacgaaca tgataaagat aatatcattg gttatccaac    15000
tgaaaatacg tttacagact ctaaacgagg tttgtttgta gaagcaaaac tttttaagaa    15060
taataagtat gttaagtctt taatggatttt aattaataac ctgaaagaaa caggttcttc    15120
taggaaatta ggattttcta ttgagggttt tattaacaag cgagatgaaa ataagccctc    15180
aattatccgc aacattcaaa ttactggtat tgctgttact aaaaacccag ctaatccaga    15240
agctacatgg gaaacagtac agaagtctta ttatagtggt ttaactgctg gatatggggt    15300
aacgcctgat actcaggtag atggtggggc actaaaagtt gaatctatgt taggttccat    15360
gaataatatt tctacaatgc taagttctgc ggatgctaac ccagaattgt ttaagcagtt    15420
gggagaccaa ttagcaaata ttattgatga taaccaaaat tcaagtccta tgcttagtca    15480
attgtatctt caaatatttg aggggttgtc aagagatgaa gcacatgatt tactttttaa    15540
aaatgaaagc gaggaatagc tattggatac taaaaaaacg ttaaagaag ctttaaagag    15600 tttaactgct gaggataaag atgaatctga aaagaatgta atgccttctg ctaaaatgga    15660
taagcctgac ttaagtcatg gtcgtaatgg ggacattcaa cctgaaagtt cagatagcaa    15720
aggtactgct gttcgtgact cagacgaaga agataaaaag aaaaataaag aaccggttgc    15780
taagagtgaa acatcagaaa agagtgaaaa ccctgtatca gaaggaaata agctgatga    15840 agtagaatca ggtaaagatt ctgatggtgt aggtgcagat gatacagaaa gtctgaaaa    15900 gactagtaaa tcaaatgaaa agcctttaac tcctaagcat acgtccacaa ctaataagtc    15960
agtatgggat gataagcttg aagatattaa taagtcacta gatgctttaa ctaacaacaa    16020
cgaacgcttt aacgaactta tggagaagtt accagatgct cttgaaacag ttgtaactaa    16080
gtcaattagt agtgttagag aagagcttct aaagagcgta agttctggta agaataagac    16140
atcaatcact gaatctgaaa aggacattga cggaagtcaa gaccaatccc aaaaggatgt    16200
agatagtgat gaagatggtg acgaagtaga taaggacgtt caaacggta agaacactaa    16260 ggatttaact aagtctgaaa agtctgaaca cgtcaagaag gatgaagacg gcgatgaagg    16320
```

```
cgatgacgat gatggtgatg acatggatgc ttctatgggg gataagaagg gtaaggattg    16380
cgctactaaa tctctaaagg gtgtcggtaa ggctgttcaa actgacggag aaggcccaga    16440
agaagcttct aagtctgtag agtcccctgt agttaaaatg actccggaag aggttaagaa    16500
gtctgctact accctagagt tagctgtagc caatcaaaag cgaacagcat ctggcaaacg    16560
ttgggatgac ttagatgaag tatataacat tgctaaatct gctagagaaa caggtaaaga    16620
agaaatttat aagtcagcat tcagtaaatt tacagagact tttaattaat aattaaacaa    16680
aagtgtatac ttctttatat tattactaga acgtaattga ttcataaaat taaaactacg    16740
attaaaatac gaagggattg ttaaaatata tgaacgaaaa taaagcaaaa gaagcgttag    16800
aagaagctaa taagtcatta gtattaaatt cagaacaaga acaggctgtt aagtcagctc    16860
ttacagcagg ttatggtatc gcacctaacg aattatccga tggtggggcc ttgaaggttg    16920
aatcacttga cccagacatc aagaaccaat cctacggtgc taatgattgg acaatctacc    16980
ctcaattggt aggtcaaggt acagttactg ctaagtctac agttgaaaag tatgtaacct    17040
tcttgaagca tggtcgtgtt ggtcattctg ttttccaacc tgaaattggt attagtaatg    17100
ttaactctcc tcacttgaag caaaagactg ttaaccttaa attcttgact gatgttaagc    17160
aatctagttt tgctatgaac tatgccgcta caattgaaga cgcccaaaag attaatgaag    17220
aagactctat cattgttatt ggtaagacca ttgaatgggc tactttctac ggtgattcag    17280
acttaacttc tggtgaaaag ggcgaaggtc ttcaatttga tggtttggct aagttgattg    17340
atgaaagcaa ccatttggac ttacgaggtg gttctcttac accagaagta ttgaacaagg    17400
ctgctacttt aattggggaa gggttcggat atgccacgga tgcttatatg cctattggtg    17460
ttaaggctga cttcggtaac caattcttag gcgctcaacg ggttattgtt ccaagtaatg    17520
aaggtactac tgctggtgtc gatattgacc acttcttatc cgcacgtggt aatattcgcc    17580
tgaatggttc tactattatg gatgctgatg accggttgga tatggaccaa gttcctgatg    17640
cacaagctcc gggtgctcct gtagttacag cagaagaagt taagagcgca ggtggtcaat    17700
tccaaggtga acttaaggat gctgatggcg ttgtatattc acctgccgaa gtaggttctg    17760
cttttgaatta tcgggtaact gctgttggtc atcatggtga ttcttactca tctgatgttg    17820
ctacggctac accaacttct gctgattctg gtatcaagtt gactatcaag ctagatgcta    17880
tgcaacgtga aattccagat tacttggcta tctaccggca atcattagta caggatgaa    17940
ctaaggaacc agaattttat ctagttggta cagttgctac gcgtgaaatg caagaagacg    18000
gtagctttac ctttactgac ttgaatggtc ggattccggg tactgctgat gtctttgttg    18060
gtgaaatgaa gcgtaatgtt attgccttga tggaattcat gccattatca aaggttaact    18120
tggctgttgt tacaactgct gtttccttttg cggtaacgac ttctgttgct ttggcactat    18180
acttgccaaa acgttgggta atgattcaca atgttcgtta caataacgca gttgaaaatc    18240
atatggccgg tgttaactta cgtgcttatg taggtaacaa ataatataat atttaataat    18300
tagagggagt taataacttc ctctttttttg tgttataatg tgggtaatct aaaataatgg    18360
gaagcgaaaa aataatgaaa ttattagctg gaatcttctt agttattgtt ggctttacac    18420
tgttaagcac tattaataac ttagtaaaat atattggaaa tacgaagtgt tacagagaag    18480
gattatcttc acgagaagaa cttgataagt ccgggtatgg tgatttgcga aaatattta    18540
gtaaatctga atccgaaaaa ttaattagta ttccttaataa gagtgcttat tcttttgtat    18600
ttactgagtt attatttagt attattgtta tctctatttta tcctgttcca ctcgcttact    18660
```

-continued

```
tagttgctat ttcaattgca attgcgtatg aattagctac agatactaag caattaatta   18720
attataataa gtatggagtt attggagaaa cctattcagg acgtaaaaga tactatttag   18780
atgctttcaa tgtagttaca ggtattttgg gatttatttt accaacatta attgtgttaa   18840
ataattaagg gacctataaa gggttccttt ttttattgcc taaatttggt aaacttaggt   18900
tatgtaatac tcttatatta ttaactagat aaaataaaca agttttatta aggaaagggg   18960
acgttttctt gaagccacaa gactacttta aagtaactaa taataagaat gatggtctta   19020
gcatgtttta tggtaatcct aagaaaattc cagacgagtc taggcttagt gaaataactc   19080
tggaagattt agggttcacg gttcaatcag ttaaggacca gttattaggg atggacgatg   19140
acttagttaa tcctgcaaca ggagaacctt atgatgattc aatttataaa aacgttattc   19200
tccgtgcggt tgctacaaca gaaaaagaat taaatattgt aattagacca agagtaaata   19260
acgaaagatt aaactttaat aatactgagt atcagagttt tatgtatcta agaactgctg   19320
aaaagccaat tcttcaagtt gatagattgc ttatacaatt taatggtcaa cctgttatgg   19380
aatttccaga tgagttgatt aaagtaaata acttattcgg tcaaattaat gttcagccaa   19440
ctattctaat gcagtcatct atgagtaact taccaagctc tatggttgtt ggtaactatc   19500
cacaagcagg catgttaggt gttggtggtg ttgttaaccc taactgggta cctcaaatga   19560
ttggtgttag gtatattgct ggtatgattc cacaaccacc aactgacgaa ggtattaatc   19620
gtttctggta tccacatcca gatttaattt cctatgttgc taaaatggcg actgttgaaa   19680
ttcttgaacg ttggggtaga acaattattg gtgctggtat tgccggttac gatattgcta   19740
ttgatggtat tagtagcagt gttaattcaa cacaaagtgc tgaaaatact ggttctactg   19800
ctgatattat gttacttcaa aatgatatga agatattaa gaatggtctt agagcctact   19860
atggtgataa ctttggcgtt cttagttagg gggatatgtt atgtctgaaa ttgataaaga   19920
tattgattac agtgacccct attggtttaa aaataagaag ttaaaaaagg attcagagat   19980
taccaagact aagaattcaa ataatattaa tccgacttta cctcgaaata atacgcctag   20040
gcaagacgtt agtagaatcg caggtctatt agagagaaca ggtcttccta ctatttggga   20100
acaggccact ccttgtcctt gcattaatcc agaaactaac cagccaaaaa cagattgtcc   20160
cttgtgtttt ggtagaggtt ttatttatcg ggaaatgcat accctaacca ttgcatatac   20220
ctccgatgac cggggggctt attttggtag tcaaggtcag caagaccacg ggtaactac   20280 tggaactccc caagtgactg aaaatggtat tgaggatggt attgctatta gagatagatt   20340
aactataaag ggaatgaatt tgtctaatac ctacattgct aatgttagtg aaagacgata   20400
tagagatggt tttttaatac cttatcaagt tgttaaattt aataacgtta taagtattga   20460
tgataaattt aatgtctatc aacttaaaca gggtgaagat ttcgaatacg atgctaggag   20520
ttccatgttt aaggttttga atcctaagct taaaggtaaa aatatctcta tgaatctatc   20580
aacacaactt agatattatg tatctaatat cactaaggaa actcgtgtag ctgatattaa   20640
aaagatggaa gataaaaagg tattaactga taacgggaat attaaattag ataattatta   20700
tcgggttgac ttaggtgacg ttaagtattt tagaatgcca aaaaaattag ttcttaggcg   20760
tgaagatatg tttataggtg ctagcgattt tactgctgat agcactaacg aaaaatctaa   20820
atcccatata tttgatgcca agaatacga tagctcaatt aatcgattta tgggtggtgt   20880
ttaatattgg cagataatga aaactctctg gtaagtttaa acagttcaga atagataat   20940 gctttaaatt caatgcttaa ttcattaact atatcgactg aatatgctaa ggatttgtcg   21000
gattggatta atcagtcttc cacgggtatg cactctcata gttccggaaa tgacttacta   21060
```

```
gtaactaaaa aaggtatgga agcccaagct agatttcagg gaattagttt tgttgatatg   21120 aaagagttttt ttaagaactc acctaatgct aaacaaaaga aaaatggtgg ttggtacttg   21180
attgttccta ttgggcaaaa tgcgacaaat ttaaagtcat cttccccacg ttcattgtgg   21240
aaccagatgt caggtatgga ttttggaaaa acaggtagtt tgtctgatgg ggagactaat   21300
tttttggaac agtcatctaa tcaagaccaa tcgaatgtta ttaatccact taattataac   21360
tggaagtctg ctaatgtaac cagagtatct tcaaaaacag gtaatggttc cagaggacac   21420
tatatttcgt ttagaacggt ttctgacaag tctgacccta actcatggat tgtaggtaga   21480
gaagccttca cagatgataa tacgggtcct gaacagcaag aggacattgc aaacctaatg   21540
cttagtcaga ttgcaaaata taattaaggc ggtgagtata aatggcaatt ccgagtgtag   21600
atacttattt acgcaatgaa gtatcaaaac aaatatcact attacaggag aatccttata   21660
ttgttaagga gaacatctta aaggattttg atgacaaggt agcaagttcg ttcgttaata   21720
ccttttgtaa taccagtaaa ggttctggaa aagaaatacc agtaactttt acttttggta   21780
acaacaagaa tccagcagat gcttttatcg ttatccaatt caagggttcc tccgaaagcg   21840
atgacgatgt ttcttttaggc ggtgttatgt ccgaccatga tgttgcggat ggaaacttag   21900
tacaagaagt tagctatttta actatagaaa aattaaatgg attctataga gcttactttg   21960
aagttagcca gccaatttct aatttaggag atattagcac tttttcaggt aacttccaaa   22020
ttgatgggaa tcgaatctat attccatatg atgatagtat gcaggatggg ttaaataatt   22080
ctacttataa taaatctatt attacttata gtccacaaga tatagatgtt gacaacaaca   22140
aaaaggttca taaacaaact atattaactg gttatgagtt tattgaaaat tatacgatag   22200
atagcgtatc taataatcaa gacacattaa gatgcctaga tgctatttta aagactatcc   22260
taatttatat gagatataac gctacagagc aaacagaata taaggtagca caacttaaat   22320
ttatgggttc tgacctagtt gcagtaaatt caccagattc tacagtatt ggtgaacaga   22380 ttttctatag aagagcagaa gttagctaca aagtgactta ctctattgaa tcatcgtatg   22440 gtgtatttttt aaagaaatta aatgttaacg gagggttaa atatgaagac atcaacaaag   22500
aataataata agattgacca ttattattct gtaattgatt ttgttaattc tgctaggggt   22560
aactatgatt ttagtctagg aaaagatgaa gggtttattc aatttatgaa gaataaaaac   22620
aagttttata tgctagatga gaaagtttt attccttact ttaaagaata tttaaataat   22680
tagtaaaaaa gaaaggtggt aaaccacata tggcaaatat tgaagatgat taccaaaagc   22740
tttatcctct atatgcaatt gaacgtcctc atgtagaaat gagttacaat ccagatgcac   22800
taagaggaca agcttctgaa tcagaaaagg ttatcggcat gattggttct gctgataatg   22860
gtaaaccaaa cacattgtac aaggtgactt cactgttaca agcaaagcag atttttggtt   22920
ccggcgaact tgtagatgct ttagagttgg cttggtcaga tgatgctttg ggtggttcta   22980
tttatgcaat gagggttgaa gatgcaactc ctgcgagtct tgttgcaggt ggattaactt   23040
ttaattcaca agtttacgga gataattcta ataaaactca ggtagcgtta gaacgtaatc   23100
caattaataa ctcttatcga gttacagtcg attatgaacc agatagttat cgtcaagttt   23160
atgataactt aggtcagatt tttaacatca gttatacgcc aaatgatgct tcaaaggcta   23220
aagcgactta ctcagttgaa aaagctgatg atggtacagc taagaagttt attttggaca   23280
ttacagatgc taaggaaaag gttactacga ctacaacgtt aaagccagat gatacaacta   23340
cgactacaac gttggcgcct actacaacca cgactacaac tagcacgact aagaaaccaa   23400
```

```
ctacgactac aacgacttct actagtacga gtacaacaac aagtacaact acgaagaaag   23460
ttagcgctac tagtatcaag tttgatacta acgtagcaac tgttaaaacg ggtgacgatg   23520
ttcagcttag ttggaaggtt ctaccagagg gtgcagatga tactggaatt actttcaagt   23580
ctgatgcccc aacaattgcg actgtagatg ataaaggtaa agttactagt cttaaagatg   23640
gtacagccaa tatcacaatc tcattgggta gcctaacgga tgccgttaag ttgacgattg   23700
gctcagacca gacaactgat tttaatggaa aaggtcaaaa cttagatgtt gctaattttg   23760
ctgttgaaga tgacgacttg attaacattc accaagtatt tgatttaact tctagcgact   23820
acgggacggt atttgaacta atgaactctc ttagttttaat tcccggaatt actattgcct   23880
tttctaactc atcagacaat agtacaacga atactgctat cctagatgcc gcagaaggcg   23940
ttaacatcat taccgatatt aatgacgtag acaccgcaac tagtgtttgg gctgttatgg   24000
gtgatattgt taacagacta caatacgaca gttatgttag tgttgttgct aacttatcaa   24060
aggagacccc agatactttt ggactaactc cgatgattgg tggtagtaca ggtgtaaccc   24120
ctatttcatg ggccaagaag tttaagccat ttgcacaagt tcctgtttac tacatggttg   24180
ctttaacgca aagtggcgct gttcaagcag aacttaaagc ctttatgaat gaccagtatt   24240
catctggaca ttccatgaga gggtttgtag gtgcaggcta taacgaagca gatggacaac   24300
ttctatctcg aagacttgct cttaaagaag ctcgtttagc cttaattggt agttctggtt   24360
ataagaacat gaaagatgga cgaactcttc atctacccgg atatatgtta gccgcttatg   24420
ctgctggtgt tgcttctggg ctacaaattg gtggtgcctt aaccaacaag tatattgact   24480
tagtttcaat tgaccaagac tttaactctg ctcaattaga tagattaaat tctcagggtg   24540
ttatcattat tgaacctgta atgaatcgtg gtaacgccgc agggttcaga tttatccaag   24600
acgttacgac aaacaactca actaatgaac ctgttaagtc aagaattagt ttgggtgaac   24660
ttactgactt cttgtttgat gacttacgat ttgagcttga aaaacggttt gtaggtgcta   24720
atattcgaca aacttctaag gaccaaatta agaactttgt tgatagctac ctttacaaac   24780
aaaagttaga tactacagga ttagttgtag attatgaccc cgatgatatt caggttcgtt   24840
tggatgctga tattgcttgg attatgttta cagttaagcc tagtcaaaca ttggataaga   24900
ttcttgtgta tggtgcttac cagaacttta ctgattcaac ttcgacaaat aatggctcag   24960
atgcaacaaa tagtagtaat acttctattc ttaactcatc taacccagat attaatgccg   25020
gatatgaatt tagtaatggg gctacagata ccatcacaca cgacagttct aatggaattt   25080
ataactaagg agggatagct aatggcaaga gtcgcagacc agtcagttca aacaggtaat   25140
actatttatc taatgattga aaatacacct atcggtcggg cacaatccct gactgctgaa   25200
cgtagttttg gtaccgaagg tgtttatgaa attggttcta ttatgccgca ggaacatgtg   25260
tttctaagat atacgggaac cgtccaacta gaacgttacc gaatgaagaa acaatcattg   25320
gcaactctag ggttcgccgc acttggtgaa gaggttttag atattccagt tatcgatatt   25380
gtaaccctag acaatttaac taatgaagtt attattgcct atagaggatg ttctattgat   25440
agctataatg aaaactaccg ggctaacgct attacaggtg agtcttctag gttttattat   25500
ttaacatcta ctgctattca gggaactaaa taaaaaataa ataaaaggac acctcatata   25560
gttggggtgt ccttttttgg tgctaagatt tatttcttgt aaaccttctc aggtggtatg   25620
tggataaaaa tcttattacc acgatgatta tcgctaggaa ggattacata aggtttattt   25680
tcaagcttat agtcaatcac ttcggaaaaa tccatatttc ttggattaat cctaataact   25740
ttagttttat ttcctgagta ataaccaaca atataatagc ctatttgatt atcactattt   25800
```

```
gattctgtat caacaaatgc taatttaaac gttcgtccaa caaagttatt ttttgcataa   25860
ctgtatgaca tctctgataa tgccggtact ggtcttttca cctcctgata atttgtattg   25920
tatgctggat tggcattaga atagtctggt cctttatgac taaatctatt aacataaata   25980
gaaaatgtta gcacagaaag tgcaattata atattaatgc caacatattt catccaactt   26040
agacctttgt tattcattct atctacttcc ctccatattt agcttttaac gagttttta    26100 ttagtacagg tgtaattaca cctaattatt tataaccccc ttatatcgca ttatattgcg   26160
ttatttgatg cttataaaaa tattaatgtt tacttaatca cccctttaca aattttaat    26220 ttaatgatat gataccgtag taaatgaata tagctgataa accggagtgg gtggcgttac   26280
caccgggtga tagctcaaaa aagggtataa aaaccccgaa ggtgtaagaa gccttctccg   26340
ccactaaatc tcttaagttg gagcaaaaca tcatgtcacc cttaagcaag gtggccttga   26400
tttccgacta ccgaagggtg tctacggccc ggacctgaat taacaggtta taattggtag   26460
gagagggaag gactggctct atttagagtg gggctttata cctagatata tagcttagtg   26520
tttaacacag gggtgtttgt aattgctttg acccttaatt ataatctcaa agtagctata   26580
tctagttgtg ggacagtatg acgtaattat aaagcatgaa tctcagcttg ataagcatta   26640
tttgagagaa gactcatgag ttccatgggt cgaaaactcg cgtgataaac taaagcgaag   26700
cataaatcaa gtaactaaag ataattacat agataaataa attaaatata catattaact   26760
cttataggtt tagtattaga taagctactt agtataggag aattacaaca tgtactatta   26820 taattaaatat tgtatagata atcagattta taatatttt tatgacaatt actacatgtg   26880
tatatatatt catcataaaa gcataggaat gtattattag tattaccata tagataactt   26940
tcaggactat tggtaactaa tttatgttta ctaagagttg tttcaaacaa cttagagtta   27000
tctttatatt ctttacctga attatataag tataaatgta taccttcatg aaatataact   27060
ttattcaaaa tattgtaatc aataaaactt gatttatata tagattcaga tagttcaata   27120
gtattgttgt taagtatagt gcgtgcacct atcgtattgc ctaaattatt aacaacaata   27180 cttttttat attctatatt aaaattatct attaaaaatg tatttaaatt attctgtagt   27240
atattcaatt ctacactcaa tacgacacct ccccatatag taatataatt aagcacttag   27300
tttatattaa aaagggaaga aggcatacaa gaaaggtatt taacaaaaaa tactgaaatc   27360
gtgtaatata gagatataaa atatttttt aagaaagtag gtaattattt tgtcagaaaa   27420
tatgagttcg gaagaccaat taaaagactt tgaaagaaa tttttaaaaa ataaaggaag    27480
tagtcaacag gtagataagc caaaagctac agagagtaag gttaaaagtg agaattcacc   27540
agaggaatct gatatgtcta agattttagg catggtaact gaaatgaaag aaaaggtaga   27600
taaagttact agtgaaaata gtaagcttgc tgaggaaaat aaacggttaa agaggaacg    27660 tgatgataaa cgacaagcag ttaagactga taaagaaatt aaggctgtaa ctgatgtcat   27720
tcaaggttat cagcagaagt tccataaagt ttatgatttt cctgttacag atggtgaaga   27780
tattcattta gacattacaa tgaaagctcc tactgctggc tcacaagccg caattactaa   27840
ttttgttgtt gccgctacag atggtatgga gtggcctgct gatgcttcta agttcaagta   27900
tgaagctatg gagcactttt tggtattagg agaggaggtt cccgcttggc ttagtgattt   27960
agatacactt actagaactg atattccagt caagatttat agtgattact agcttggtg    28020 ggacaagttt taccaataca gacggcagta aatatcataa atctgtagta gatgttggtg   28080
gtataaaaaa cttagttaag tctaatccgg gaagaaatat gtggtctatc atgaaagaat   28140
```

```
ttaaagttct tccaaatgac ccattgttac aatcacttag tcaagaacag caagacttca   28200
ttctgttatc tatgtctagg gataatgatg aactgattgc taatgcaaga ggtgactata   28260
ttgatggtga ctttgaggat aaagactttg aagaaattgc cgaattagct gatgaagatg   28320
aagattggga aattatgcgt gaaggtcaag acccagataa aattcacgaa gctgttgtta   28380
gacttactgg tgatactgaa tttgaagacg ctatgcataa taagctcgaa gctaaacgtg   28440
aagagtctta tcataaagaa gaccgtaaac gtgaccttat taaaaatcag catgaattta   28500
ttaaagaaat taaagagtca tctaagaata gtgaaaatgg taagattgat atatccgaag   28560
caatggataa aattacagcta aattcaatta gagactctgg tttacaatag aagctattag   28620
gcttctattt acatattaaa attattgtag agaggaagtg taatacttgg ctaaagatat   28680
tgatgttaat ttaaaactta atgcaattaa taccgaagaa gtgcaaagaa aaattaaaga   28740
attaacggat agtcttgaca aataccaaca agcttccaat tctttcgata aaagttttaaa   28800 taaatctaat ggtaatgttg gtaatggtaa ttctgctcaa agtatgtttg attcagctaa   28860
aacatctgtt gatatatcta atgagctaaa gagtaccttg tccgatattc ttcaagcaca   28920
acacggtatg tctaatggaa attcacaagt gtctacccag cagatggatt ctttaaatag   28980
agtcgctagt cagataaccg gagtattttc aagttcacag agtgtgggac taaatccttt   29040
ttctagtcaa ggaagtcagt ttaataatcc taattatgct aaggctcagg attatttaca   29100
aagaggttct ttaactagac cttctaccccc aaatggtacg gcagaggaga gattaaatag   29160
tctttctagt cgtaatcagg atagacagca atataattct tttagagatg aaattaataa   29220
gttgacggct atgggtaata acactgagag aactgttaat accgcatcta gtcaccatac   29280
aatttcttat gaaagaaacc aagcattgtc tggtagattc gatgaagcgg gtcagcgtat   29340
tagttcctta tatcatgttg atggtgaggg aaatacttct ggtagtttgg cagaagctag   29400
ggaatcccta gttaatcgtc agaaccaaga atatgagagt cgtaattctt ctacacaaga   29460
tacatctgag tggaatcaac acgataaaga agctgaacaa attggtaagg taatccaaca   29520
atatgattca ttaattaata aaattcagca acatctaca acttttgata aagctaaaga   29580
tgacttaaat agtggcttat cctctggaaa tattagtgaa caggctaagc gtggtagttt   29640
tggtgatatt ttaagtaccc gtagctttgc tattgccgct aatacaatga atggaatttc   29700
aagtagcgtt ggtaactcta tgtcatctgg taataatgct agattacagt catctaatag   29760
tatagatgct attacactgg ctaatgggc taatggtgtt gataataact ctgataatca   29820
cttattaaat agattagcaa cttttaggagt tagaaatggt acgggttata gtgcaaccga   29880
tatgtcccaa tttgcatcta cttattcaca aaatagtgga aatactaatg tttatgctga   29940
ccagagtgtt gctaataata tgagtcagtt atctaggttc gaaaactttg gaacagggac   30000
aactaatcaa ctgtatagtt ctttaggtgc aatgggagcc ttaaatacag caggtcaatc   30060
aactaattta actaatagta ttgctagtga aatagctggt tcgaatatgc aaggtagggc   30120
aggacaacag ggtcaggctt tgtcaagtat ttatggaaac ttattagcat caggtcatac   30180
acttaataat tctcaggcag ttggcatagc aggttttcag ggtgctatgg cttccacggg   30240
taatcgtgcc ttcaaggtg caagtggagc aactgcttat aatcaactag ctaatggaat   30300
atcaagtaat atgagtaatc ctgctgttcg tatgtcattt ggtggcaata atccaagcta   30360
tgccggtatg gaaggtcaag ctagattaga tatggatatg aacgaagcag ggaacaccc   30420 agaaaaattt gcggtatga ttcagaattt aaagcgaact tatggagcga ataatagtac   30480
aataactgct gatacttga tgaaacaatt tggtatgtca gcagaagcgg ctagaggttt   30540
```

```
tgttaaagct tctgatgatg gaacgttaaa tagcaggagt tataatcgat tagcttctaa   30600
gtatagtgga caattaggta cgttgcagaa acaatattct agtcaaggtg atagtacact   30660
aactaatcaa caagctaatg aacaacgtgc taatatatct ggtagtgaag ctttagatgg   30720
tgttagaaat gcaagaaatg ccgcaggctc taatatgtca ggtattgcta ctttaggcgg   30780
taatgtcctt ggcggtgtcg ttactggtgt tgcttctagc atgggttctg tattaggtgc   30840
atccgtacta aaaggtggcg gaggtaagat actaaaaggc acaaagttag gttctctgtt   30900
cggattagga aaaggagcta aggatgttgc tagtgccgca gataaaacag agggtgttgt   30960
tgagggtgct agtggacttt ctgggttatt ggtaaaggt gtaacttctg ctaaaggttt    31020
aattggtaga ggagttacag caactaaggg tcttttatct aaaggtgctg gaaaacttgg   31080
tcttgaaggt ttgtctaaat ttggattaaa aggcgctgaa aaagttggtc ttaaaggtgc   31140
tgaaaaagta ggaagtaagt ttattcccgg tgttggatgg gctatggctg gtatcgatgc   31200
tgtaagaggt gtcggtgata ttgcgaaaga ccctgctaat gctcttaggc accctattaa   31260
gtctgtaggg agcattctag ggttaactag ggtaaatgct aatgaaaagt ctaacagcga   31320
tagtaaagga aaagataagg ctaataataa gtctgaacgg gtattagacc atgcagataa   31380
atggttggtt gattttaatc gaactttaga tagagcagat aggctaatta ctaatgctaa   31440
aggaattaaa ttgggaactg gttcaaagag ttcaaaggct aattctacag atgattccga   31500
tgatggtaaa ctatccggaa gtgcttctaa gaaagctaag caattagcaa gtatgattaa   31560
gaagaagtat cctaaagcta atagcaacgg tatagccgct gttcttggaa attggcaaca   31620
ggaatcagga tttgacccaa ctgctgtaaa ttcatctggt gcaactggat taggtcaatg   31680
gttaggtgga cgtgctgatg acttgaaagc ctatgctaag aaaaaaggca agtcatggaa   31740
agaccccggc ttacaagttg attttgcttt aaatggagat ggctcaaact ctaagatact   31800
aaagcaagta ttatctggta gcggttctgt tgatagttta acagcagatt actataataa   31860
atgggaacgt ccgggagctt ctgataagac gttgcaaaca cgtaaggata atgctaataa   31920
gttagcaaaa catgcaacag gtatgattgc tatgcaacca gaagctggtg ttattagtga   31980
agagtaccca gaagctgttc ttccattgga cccatccaga gcaaataatt ctcgttcaat   32040
acttcaaaat gctaatagga tattggggaa tacaattagt agtccaaata gtaatacagc   32100
aaataattct acatttagtc ctagttatag tgtatctatt ggtaatgttt ctggtagtga   32160
gcaagacgtt caaggattaa aggttcaatt gcaagaagta ttatctaagg ttgctagtca   32220
tgcacaacag cagagtaatc aacgtcaaat gaattttac tctaagaatt ttaaacgtat   32280
ttaattagtt ggattgagat aagggctatg ttcttgtttc aatccttctg ttgtataata   32340
gatatataga aggtgatttt attgggaaag tcaagtaata attttgaaaa tatgaataat   32400
ccctatgacc ccggaactaa gattaaggtt aacaataaaa gtgataaaaa caacaaaaag   32460
tcaactaaga agaaaagaa cacaagtaaa aagggactaa tatttaattc agtaactgat    32520
aaacaggata ctgctaatgg tgctggttct gtaggttctg ctaatatatc tggtaaccct   32580
aattggacta atccgtcaac atcagaggat gaaattgata gattaaatat tgtgttttcg   32640
gttgattttt ggactcagta tggattacaa cgggcaacct atactttagg tagggtcgat   32700
aatgatgact tacaggttcc agttgccaca ggaattaaag atgagctatt aggatttact   32760
acaaatgtag atatgaatca gaacacgcca caatttcaag tacagttaag tggtttaaga   32820
gattgggaag atgtttttact ccctaacgat tatttagaaa tatctgcaaa agtttacgaa   32880
```

```
gattccccaa ggtctaatga ttctacaacg ggtacagctc aatcacctgc atctgcaact    32940
ttaattacag gattaatttc taatattcat aaagtagcag attcacaaca aggatattca    33000
tatgtcatca cttgtcaggg aatgcaaaaa atattagata acattaatct aggtttaccc    33060
tctgacttgg aagctaatgg tggaattttg ctctatgata ttgggcaagc atcagaccct    33120
aacgttaaag gtagttcaga ttctgttgat ggttcaggtg gttggaatgg tagtattcct    33180
aaaggactta aaggtaatct gaaaaagatt gctccatatg ctgaaaagta tggagcaaag    33240
tacaaggtac ttccttctat gattattgcg caatctgttc aggaatcgag tttaggtact    33300
gcagttccta acgagtataa ttggtggggt ttaactggaa gtattggtca tggtacgaca    33360
aatattggtg gttatcctta tactaaattt gatagtttag acgaagctgt tgagtattat    33420
gcttcgtgta tgggtaatgc tagtcctggt aagtcttact gggcagttaa acgtattaga    33480
ggtatcagtg atgctaaaaa ggctattgcg gttcttggtg gggataatag ttatcacgaa    33540
gctagtgcta gttcatatac tagaggacta acaagtgcgt acaatagata taatttaaag    33600
agattcgaca aaaatattca ttttttaaggg ggtaaatata atatggcaac taatgatgtg    33660
gcacaaggag ttaaggccat gcaaaacgct cagaataagc aaaataaggg cgttaaagtt    33720
accgaaaatt ttgtaaggaa tatgatacct aaaattccgg gtaagactag taatagttct    33780
aagggaacag aaatactaac taaggctaag aagccagcca aaaaaaagtc tagtaaggac    33840
aatagtaagt caaagatac tgatgatagt accaatccaa tatctggtgc tggtatttat    33900
ttttacggta gaatgtcagc agatattatt agacaaattt tagatatgtt tattttttgca    33960 gttaaaccac ttagttctga taattctgta atgattctta ataaaacaaa tggtaaaaag    34020
agcgcttcca gtgcaagtga ttggaattct ttaggagata caaccggtgt tatcaatctg    34080
atgtataatt ataagaacga ctcaggtaag aaattaaaaa taacgggattt aattgaaaca    34140 aatattccac cggaggaaga acaagctcag tatttaaaag accagatgac tggtaatggt    34200
tcagcaggta agattaagat atttaacccg gatgaagcta tgattaataa ccccccagcag    34260 tttatggcct ataatggttc tgtagcatca ttaattaggg atttatccaa ttcaccattt    34320
aatgagattt tttggacaca tgaacaatct ggtaaagcta agcttaatta tcggcagacc    34380
ccttttgagg aagaggactg gaaaaattta gattatgttg ttgtggatag taaggaactt    34440
ttagattttt ctttttgatga aaatgataat gaacaatatt ctatttttcag tatatctagt    34500 acgagtatgc taaatgatat tagtattatg tctaaggtcc ctcctattac agatgaccag    34560
aatgaattaa tttctcgtta tggatataaa tatttaccat ctgtacaatc ggattatttc    34620
tacgctcaaa gtagtggtag tggattagat aaagatgatt taaacaaggt ttcaaatgac    34680
cagaacaatc aaacggatga tttgaacgct agtaagtttt acccatcata taatgccttt    34740
attatgtatt ttaaggtaga tagcaaagat ttagtagggg gtaaggataa taaaaagctt    34800
gcaggtttaa cttatactat atccccttct tatggtggag atgctttgta cgagattatt    34860
cagagtgatt tagctaacaa taaaaatgca agtcaaatag tcaaggattc aactgattat    34920
tataataagc atacagatgt tatggtaacg aatcctatat ctgatacggc taaggttact    34980
tctttaaagg ttgcctatgc agaagcaggg gatttaaata agtatttata tgctagttcg    35040
gttttaccgc cccaagaaaa tccatatcca acaagtatga agaatcaagt taatggagga    35100
ttaaagtatg cgttaagtaa aggattagct tatatctctc aacaccctaa atattcagct    35160
caggatattg ttagattatc tgaggggaaa attggcgctg gtcaagctat gagtattatt    35220
aatacttata ttaaaaataa aggaacgatt agctcagatg aatacaccaa tatattaaat    35280
```

```
accgtttctc atagtaaaca agtatcaggt gttaatacaa acacaactgt atcgggtgac    35340
ggccaagact ctatctcgcg gtacaatacg taccaaacaa aactgtttaa ttggtatgcg    35400
gataatacta agatgcttag tggaactatg gttattactg gtaagcttgg tgttgagtgt    35460
ggaaagaagt tatattggcg agatgaacgc cgtggatgta attatgaagc ttatattgaa    35520
tcagtttcac aatcttttag ctttatagac ggttggactg taaccattgg ctttaccaga    35580
ggattaaagg tatcagaaca gaatgatgaa aagcgctgga atatgtattg gggacacgga    35640
actcaattta aaggcggatt ttttggtgaa atggttctac aggatattat tacccaagca    35700
gagaaaagtg aagaggattc agatagtagc gataaggata gtgatgatga ttctggggat    35760
acctcgtcaa ctggaaattg ggttgaagct tgtcgtccaa gaccaggaaa tacttggggg    35820
tcacatgatg caggaacaaa ccaactattt ggtaacacaa gacccggatg gcctcatatt    35880
ttccatgatg gatatgatgc gggttctgct aaattttatc catctatata tgctatgcat    35940
tctggtgagg ttgtgtatgc taagccgtgg ggagaactcg gtagtgaaga tagttatatt    36000
gtaattaaaa gtggtgatat atatcacact taccaagaat tttcagcagg aaataatggt    36060
gtattagtat ctaagggtga ccatgttaag actggtaaga agatagcaac tagaacgact    36120
ggctctcatt gtcacgttgg tattagtaaa ggtgggtatg cagttaacgg gctaccatcc    36180
tattcaaagg gtagtggtaa caagagatgg tatgacccag ttgaatttat taagaagcat    36240
aagaagtagg tgatataata atggcagata aagaaatagt tgataacccc tatagagaac    36300
aatcaacatt aacaactaat cgtaatttag tggatgaagt tagtccaaat gttgcaagtt    36360
tatctgtatt tgtggctaag gttgtttcag tagattatga aaaaggaact attggctata    36420
gtgaaaatat atctaatcct aattatctat atcctacagg ttatgcaaaa ctacctgttt    36480
ttaatgctgg taagacagat gaagataagg tttatggtcg ttaccctagc attacaccgg    36540
gtcagagagt tttaattgct ggtggtaata atactaactt tactcctatg gttgtaacct    36600
cttactttga taaccaagac gatgttaagg agttatcacc tcagactaat actgatttta    36660
ctaataactt aagggatgtt tacccatcag gtcagacaag ttctgtatat gctaatggtg    36720
actatttaag aacttttaat ggtagctcat tcttttatgt ttggttggat tctaaagtag    36780
aagaagaggg aatatcccta tgggatgact atttatatga tatgaatggg aatcctgtta    36840
tttctggatt atatcaggtt gctaatgact ataaggatta tgacatggaa agtcaatcac    36900
aaaatgttgc ttttgttcat aactctaatt ctgatttaga tactcataaa acagtattta    36960
tgattaataa attaggtgaa ttattaattg atttcggtga taagattta acagatagaa    37020 atttattaag attgaccgca tctgaaacag gtggactcga tgtaatcaag tcaatggatt    37080
atgaccacga aaatttagat aattcagatt attatttaaa gtttggtatt actaaagatg    37140
atactattga ttttaaatac cacaatggtc caactagtac aggaatttca gttactaaag    37200
aaggtactta cgttgatggg gtattagttg cttcaagaaa caacgttgaa aatctatcaa    37260
cagatttaaa aacgttagaa gacaatttta atattttaaa tgataagatg gcatctttag    37320
gaacagattt ttttaataaa ttcgaagtg atattactca ggcgcaaaat gatattaatt    37380
tgttattctc taatacctct actatgagtg cagatatagc tagtaataaa tcagatatat    37440
ctgttatcag agggaatata acgggtattt taagttggca aagtgaagct aataattcat    37500
ttcatgatat taatacaaag ataagtacac taagttcaga aatgtcaaca aggctaacta    37560
atattgaaaa taggctacct agtggaacaa ttactacaca aagttatgta gattctgaaa    37620
```

```
ttaataaaat taaggttagt tacgttacta atgacactta tacagtatta gtcaacaggg   37680
tgtcatcttt agaaaatgaa aataaagtat taaatactag tttaacagag ttaaaaaata   37740
attcagtatc gaaaacggat tatgagagtt tagtagaacg agtagaagct ttagaaagta   37800
agtaaaaaat gtcctcacac gtgtggggac ttttcttata ttaaaaagaa aaaggggttg   37860
ttataatgat aggggttagt ggaaaagact caaatatgaa attgcaaaga gtcgccttta   37920
gacaatataa taatgatgga acagttaaga atacttatag atttaatatt aatccctcta   37980
attttcagga gaactttaat gctcggaata tatttatgca gacagaatcc agcattcaaa   38040
tgcaaggctt cggtcaaggt ttgcatacga taacaatttc tggtacgaca ggtgttagaa   38100
gtatgaaagg ttctagtatt tctcaaacat ctgggtttaa taagtatcat gaattatata   38160
atatgttaaa agagcaatta caaagtgtac atgacaatac cgataatgtt aatggtactg   38220
gtggcggagg aatccggtta gattttttag attatactaa cgaacattat tataagtgtg   38280
aactaagtcc agatggattc cagtttactc aaagtaataa taacccatta tcttatttct   38340
atagtataaa tttagtcgta gttggcaatg ctagtgcgcc tagttattca gaaacaagtt   38400
ggattgttct aggaaatata aaaccggccc tatctaaaaa agaattatcc aagtattcaa   38460
ttgtatctaa aagttctcag tatagtaagg atttatatgc tagtggaaat catagcaatt   38520
atgttagtgt cattggttca aaagttagaa cctctgcatt aagtaagatt gctaaggata   38580
ttgaaaataa tatgctatct aggggggcag atggtatgcg ctcacctatt ataaattata   38640
aagataatgg tccagcctat tcatttcaga aacctttatc aagttctaag atagctaatt   38700
tatataaaaa tgtttataca ggaataaata aaaaagttca cattgtagtt ggaaataaaa   38760
atgttatgga tattaacata tcatctgata attcctctgc atggaatgct tattgggatt   38820
tatatacaag aagtgctgga aaattaaaag caggtactaa aaatggtatc atagactatg   38880
gacaaggttc tgctaatgat gccaatagtg aattgcccga ctatgatagc aataaggcgc   38940
atgagaccct gtatggttca acagtagcaa acttagattt aacttattat ggaaataatg   39000
aaaaaatata taagcagtta tttggtaatg tttacaagg atttaatgct gatgagtatt   39060
ctaatgcggc agtggctttt aaagggggaca tccgttcaac tattcttaac tacggtcaga   39120
ttgacgctaa agatgcaagt acaactttgc caccctacca agtaaatcaa gttttttctg   39180
aattatatag tcagagagta gacaatttgg actatggtaa gtatcaaact atgagtgaat   39240
tatttactaa gatgcgcggt ggaactataa ataactactt tggagatgac tatagtgaac   39300
aagagtcatc tggtagttta gggttagata aggcttctaa tatttattct gtattatttg   39360
gacaaaattt gagtgagttt gattacagca aatatataaa tttagataat agttcagata   39420
ctatgaacga tactgatatt tttaattcag ttggttacag ccaaatatca actagtttta   39480
ctaatagtag ttatgggact ataaataatt atggtcagaa tcagcctagt gattataata   39540
ttgactctag ctataattta gatgcagtta agaaacaaat tgtaactagt ttaactgata   39600
caacttggga cacggcaact tatgggactg atagtaaaaa tattagtgga ttgtatcctt   39660
taaacacaag ttctaatgat gatacaaatt cagtagatac aagtgcacct gtagaagaat   39720
acgttaaccc taatgtatca gatagcgcgg tattatatgc ttacaatgaa atatcaaaca   39780
ttttaaaaat ataggtgggt gattgaatgg cagtaacttt accccttcca gctatttact   39840
actttcttaa tttaaaagta gattctaatc ataatttaat tattcctgat aatggatata   39900
atgattttaa tacaacggag ggaaaataca catttaatgt tagtggttct acaatatatg   39960
tattaaacaa tattattaag aatgctgatt acaattcatt ttacttgaat gagcagtcaa   40020
```

```
ttatctcgtt agtagctgat acagatttag ctaatacaca tacaggtata aatgaattgc   40080
ttagattagt tgttttagat tcttgggtgc ttaattatat tttattggaa gaccaaacag   40140
ttattcaata tataacagtt gatgacttag agaatactcg tatgaatata aaatttttat   40200
gtacattctt tggcgggtat cggaaatata gattcttgat tgaatattta cgttctttgg   40260
aaatatctat tggatatgca gagaataaga taaatttaat tttaaataat agtgatttac   40320
gatatgcaat agatgggggg tagtgattaa aattggctat ctatagagaa catgtagtag   40380
caaagggaga aaatattcag ctaatttcaa ctaaggagtt acaagatact tctaggtggc   40440
aagagatagt agaattaaat gacctaagat acccttatat tgttaagaca aattcagaaa   40500
agactcagga ttatcagcat ctagttactt atggagatgt aataaagcta cctgagatta   40560 ataatttta taatattgat ttaaatactt tagatgataa gggtaaggaa atcgtttatg   40620
atatgtctat gggtatggac ataagcctag ctgtgaacaa caaagcaggt ttagatgata   40680
atattgctta tttgtatcct agtcaggata aaacggactt agctacagct acgggtattg   40740
ataatttaaa ggaatcaatt cagagaagat tattaacgag aaaaggttct ttaatgtatc   40800
atccagacta tggaacaact atgttagata tggttggtga aaaactaaat cctactttga   40860
ttgatgattt aaaaatagaa atcgttagaa caataaaaac ggataaacgg gtagacaaat   40920
gtgaaatatt agaatatct gtaccggatg gaaaaacatt cttatgtgca gtatcaatta   40980
ctcctatagg tatgagcgaa gcatttaata tgtttattca aaatgcaaat ggtggaagag   41040
taagggtaga atagaagggg ggaaacagtt tggctagtca ttttagattt aaaaaagcta   41100
gtgaggttct gtcttcaatg acagattata ttttaactca cacaaataaa attaatgatt   41160
ttacagaagg ctcagttatt cagacgttgc tagaatcatt ttctactgaa atagaaatgt   41220
attattattt aaatgttgaa atattaagc tgggtatttg gaatagtata tacacctcct   41280
ttggattctc acggaagcct gaattaaagg catatggtac agttaatata gtatttaaca   41340
atgagactag tggcccaact gtaatttcta aaggaactaa gtttacaagc agtaatagtt   41400
tatatccaca agtctttgaa acgttggatg aatttaatat tgattcaggt actacagaaa   41460
caactataac ggtatattgt acccaagggg gagaaatatg taatgttcct gcgggtgtta   41520
ttgatactgt cggaaatttg gctaatatta gctctgtata caacgatgaa gcgtttcaga   41580
caggtagaga ggaagaaagc ctagaagacg ttagaagacg ttttagaggg tttatacaag   41640
ctatccaaag aggtactgtt caggccatcc agtttggggc aatgaacgtc cctaatgttg   41700
attctgctta tgtagtagat tctccgggaa ttgtcaatgt ttatgtgaat gatgctaatg   41760
gagatttacc agatgaactt agaatagcag ttcaaaatga aatgtattat tggtcatctg   41820
taggtattcc aattactatt ttgcctattc ataaaacaat ggttgattta gatattattg   41880
tagatgtccc taatccggct ttaaaaaatg atgctttgct taatgaaatt ggagttaagc   41940
tatcaagata tattaataag tttaaagcag gacaacatct ttatacaaac gacttagttc   42000
aaaaagttat ggatataagt gatgatggta taaaggatgc ccaagttaat gttaagatta   42060
atccagatgc ggctattagg ggtgacttag cagtcagtga tttaaattct attataatta   42120
atagtcattt atatccacac aagatatatg aaccctctga tagaactgtt gatgagaatt   42180
atattgtatc taacccagag gatttagata atggtcagta tgcaaattta ccagatggtg   42240
aggggggtaa tagtacaact agtacaacga cctcaacaac tttaaacaat gaaaataatt   42300
tagaatctaa tacttctgat gcaaattatt ctaataagaa tacaattgct aatttcgtac   42360
```

```
taacgactcc tgataataat ggtattgcag ataatcctta ttttgttaat ccactaacag    42420
tagccagtga taattcaagc aattcttttg attatttgat gtctgataag acaaccattg    42480
gacaagtaac tgatactacg ggaacttcta ttaattctta tagaactaag aatgtggatg    42540
gctctaaatt aagtattgca tatacatcag atgttaatgt gatgacttta gattacacac    42600
catatgattc agaaacatca agctatggtc ctgtagacac aaaagttgtt aatttaggtg    42660
atgatattat atttcatgac tatgaagtat ctgtatcttc tagtttaatt tatataagag    42720
atactattaa taacaaccgt acaagcttta gcaaaaaaac taatacgctc agtcatacca    42780
attctgataa ttatgtaaca acaattgttt ataatcctag tgataacact aagaaatata    42840
cggcaacaac tcaggtagat agtcaggtta aaacaattta tgtctacgat aatgaagctg    42900
tagttgcaag cagtaaaaact atcgttatta gcttatctgg taaccgtaca gagacttctt    42960
ttgatggtaa aggaaatact acaatgacta acacttatgg gccagatgga gttttaatta    43020
cttctgttga tggtaatggt cagagcttaa ttacaactac gacaactaca atgtaccctt    43080
atacgacaag tacaacaacg gaacctgcaa gcacaacgac aactcaaaca actactacta    43140
tttatccatt tgagaaacct gctcctgtta gtggtagtga tgcaaccgga gatgggtatt    43200
tacccgtatt tggagagtat ttaacgagtt ataatgaatt attaaaagca ggaaatatta    43260
gtattaactt tgaagaaggt gattaatgta tggcaagtat taaagacttt ttacaccccc    43320
tatggagaga ttctgtagat aaggattttc ctgatagcaa tgtcgaattt aataaaacga    43380
ttttagattc catcgatgaa aaactatcca tgatagaaga tgaaaccttaa aagtcaaaag    43440 aacagatgtt tattaaaaca gctaaagatg agtggctgga ctattggggt agttggtttg    43500
ggttaaagcg taagaataat caaacggatg atagctatcg gaatgctatg cttaatcatg    43560
ttaaacatcc cagaaatact aagcctgcat taagggaagc aattgctaat tttttaggaa    43620
ctagcatttc ttctgtacac atatatgaac cttggaaaga tatatttatt ttaaatgact    43680
ctcgactaaa tagtgataaa tatttccaga gtgattacta ccaatatgga attattgata    43740
ttgagattag tagaccattt aatgaagatg ttattgatgt aattaattgg tttagacctg    43800
ccggtgttat ttgggtgcta acctattccc ccggaaacga ttctaatgct gatatttggg    43860
aaatgtcacc tactaactta tccgtagcac aagaattatt aactattttt gattactctg    43920
gttggtatag tcgcttaaat gagacgctga ctttgggaac tacagataaa acatttggca    43980
gtttgccttt tattttaaat gattctagta caaattctaa tggactgctg atgggtaagg    44040
gattaaattt cggtgtaggc tactataact ctttgggtta tttgaagtct ttaatttcac    44100
ctactaattt agataatcct atgtcatttg aagataagat tataaataat ccttatgatg    44160
acctagcaaa actatcatta gatagcggta attccgttga ctttattgtt agtcgagata    44220
acagcttata taatttatta aagggaactc gtaagttttt gggttggtcc tttaaaaatg    44280
gggtatcttt agaatctgat aagctaaata ctcgttctat tgctaagatg acgcgtattg    44340
actcatcaat tgaatcgaaa cagtatatta aactaactgt agggagacc tatgtattat    44400 ccgtaagtgc taaatcagaa gctattagta atagagttaa tttattgtat gatttagata    44460
cggcacataa gaatttatta ttaacggacc aattaactaa gaactttaga acttatactg    44520
ttaagttcac gtatacgggt tctcctatca ctttaaactc cttacaccta tcagggggata    44580 taacttctag cggagacgtt tacgtgtcta gcattatgct tagaccagcc atagtatctt    44640
catcaaactg ggatttaacc cttcctgatt ggactgatag tgttagtgac tttggtagtt    44700
cgtttgatag aaatatgtca tatgtgtatg gttctttgaa cattagaaag ttttctcttcg    44760
```

```
acaatattca aagtgagggt actgttatta gtaagttagg agttaaggca acttctgacg    44820
atgttaataa atacattaat agttatctgg aaaataagaa gataactgct aagtatcatt    44880
cagacattac tgataatgtt catgcacaat tgttattcta caatttcaag ctaggaactt    44940
gggtaggata ccaagatgat aatctttctg accataaagt tgatattaat ataaatgcga    45000
atagtttgta cccttatatg aatgaatcag gttcgatgtt tattgcagtt agtttaacta    45060
ctttgaatac accttatacc tttaatttag actatattgg tattaatttg gataagaaat    45120
tggattataa aactgcttat aatatctatt ctgatgatga tttaggtgat gaacaggaat    45180
ttacctatta taatgaattg gatggtagta aagacacttc tgatatgtat acgagatacc    45240
agaaacgtta tccaattaga tatattagaa atattattgg taaagttagg tattataaat    45300
acagagagaa tgttttaaac ccagattttc ttttaaattc aaagtccgtt ttaaatagta    45360
attcagtgct gggtgatttt aattataata atattgttgg aggttcagac tctgataaat    45420
atactagtta taaggttatc cctagagaaa acgataatgg taataaattg ccggtttatt    45480
cattttctgt attaggtgct aaatctttag atagtttgca taagaattta ctaggaaatc    45540
ttttatctgg tggcatcttt tatgattatc taagtaataa ctggaatatt tctaatggag    45600
tagtagtctc aaaggataag ttagaaagtt cagacaagct aactagcagt cgtttatatt    45660
ctagttctac tgatggtgtt attagtatga ctactgatac aacgttctca gaggagaatt    45720
ataggtttac ttttgatgct agaaataatg aatcaaatgt tagaaattac gttgttaata    45780
tttatttaat aagtaataat tactccgtat tatctatgag taaaactttc cctataagag    45840
cggtaaaggg tagctacaag ctaacttttg atactaacaa agtatttcca gaccagatta    45900
aaatagaaat gtacccagaa gatagaaaag ggtttgattt aacactgggt aatactcgat    45960
tatctttaga tacacatgca accttagatg gaaaacctat agataaccta cctgatatta    46020
ttccttatag tgatgaccca gaagatagtt cagtaactta tgatgatatt cagatagata    46080
attcagatta tgctatgcgg tttgacacta tttatagtta tgattatgca gatataaattt    46140 ctggactaag tgaattatca aaatccatta gtaaggaaaa cttggcatct tcttatgaat    46200
ttaaggatgc cttagatagt ttaataactt atattggttc tatgggagtt tctaatttag    46260
gtgatactca taccttatta gttgacctag gtaaagttca tacagatgta gatagtatct    46320
tagttcacca tggttcaggt agtgatgact tagcagaata tgatagtatt gtgcaaacat    46380
ctttagatgg aattcattgg aagacatggt ataataattt tgataaggat ttaggggaac    46440
ttgatgaacg ttatcgtgaa cctactgata gtcctaagtc tataaatcta ttaccataca    46500
atgtaatttc ttcttctgtt gactatggta aatcttatga aaaagtcatg tcggatagat    46560
atggtatagg tatggaagaa tatactggtt tatcttatta cgtggatgaa ctacgttttc    46620
ctgcttatgg gttacttgat tatgtatttg gggattcatt gccggatgat gtagttaagt    46680
tatcaacagg tgatagtgtt gttaataata agtatgtaga tattaattat atgggtgctg    46740
taggtaatgg taaattattt gttccatctg acttggcaaa taatgcaact actacaacca    46800
cgacaactac gactacagtt aacccaaata cgaccactac tacgacaact gtagctcctg    46860
attacggaga tgacggaata gtatttaatg gaactactta tttaaattct gatagtattg    46920
ttctggatgg gagcaagaag tatccagtaa atcctaatag tacaaccacg acaactacaa    46980
ctacgagcac cacaacatca actactacaa ttaagcctat agatacaaaa tttgaatttc    47040
ttctttcaga tgataactct aagcttaatt ctaacaggtt attggttgat ggtagtttgt    47100
```

```
actatgttga acctgaaccg ggagaccccg ataatcataa taatggagat gtcccaattg   47160
ttccaacagc aattaaggac caagtaatta taggcgttga tttatttaaa ctggtaagag   47220
ataactatgg ttatgagcta aaagttttag gaattaatga tgatagcaat ttaagagaat   47280
tcttactaaa tactttatta ggaactagat tagttaataa ggtattatct attaatttga   47340
gtgctaagac aacaggtatt aatctgaccc tatctgcatg gagtaatttg aaagatggat   47400
attggactaa tacagaaaat ggtgttttag ataactatag ttcagagtta tcaatgacgt   47460
ttaataaatt agataactat ttaagcgctg atggaaaatt gtacttctta gtggctagtg   47520
ataattattc cggtaataaa tacacaatag ccataaatga attcaaggcc gtacagctga   47580
taactttcaa tggtattgat gactataatc atggaattta tccacattat aattatgcga   47640
tgcaggatag ttatattcat ggcagaggtg cagttaacga taaggtatta agtagtattc   47700
caattagcaa taaaactatt ggtagaaaag tacgtgttag ctttaatgtc tattccgagg   47760
gttctggtgg aatcttatac gtaggtaatg aatcattagg agttactact gagggcatag   47820
ttttagaaca aggtagtcag catgtatcat ttattatgaa cctaggaaat aataatcaga   47880
atattgatta cagtcaggaa cataaattat atgctgattt taaagaggag agctaccaaa   47940
atattcttag taattatgcc agcaaggttt ccttgtattc agatatgtta cgaacaacaa   48000
ataacgtaga tgatacagaa accgttacta atgggttgct gactaatgat agtgattcaa   48060
agttgaattc agataaggtt gttagcgatg gttctgatgc agacccaatt attacaacta   48120
cgactacaac gactactact tcaaccacaa ctattccacc aatcgttgtt gagaatgaat   48180
tagtatatcg taaattattt gaaaatggct tgaagtataa agacctatta atctataatc   48240
aagataagtc tacaagtagt tatgggcttg atattacatt atctaagtgt aattatcggg   48300
taatgataag tccacttaaa gtagaacttg gtgaaataga gactccttat accaaaccaa   48360
tagaaataaa ttaatggcag ggcaatggct ctgctatttt attttgcata ataaaaaata   48420
gtataatagt tgtaaagaga ctattaagct tatattaata accagaatac gatataaaac   48480
agaatatgga ggtggttttt tggctataga aactatttca tcacatgtta tggttgctaa   48540
aagctttaaa aatgacttac ctaatctttg gttatctatt ggtaaaacaa ctccttgggt   48600
ggatgaagat attccaccag cagaagatat gtttactact accttagatg aagttattgg   48660
atttaaaaaa ttcgatacag cacaattagt agttccggta tcatctttaa ataatattgt   48720
tccagataag actgtttctt ataaagcaga ggattgggca tttgttacag atgatgatgc   48780
aatgaaatta ggtgctaggt acgtttattt ggaagcaaca attggaccgg gggagttacc   48840
ttatgcagtt tatagacaga taggtatttta aaaggatta gctcctcagg atagattttt   48900
agataagaca gcattaacac ctaatcagat agaagatgct ggggtattgt tggggtatga   48960
caatagatta tttcaaagat actcagataa tgtaaaacta atcgaaaaga tagttttaaa   49020
attttaaggg ggtatagagt ttgacaacat ttaacgattc agcttcacca tataataatt   49080
tatatgatat taaaaaccgt tggtcaaagg ttgaatttgc accaagtaga cctttgtttc   49140
aatcagaatt aaatgaacta caatcaattt ctaatgacca gattgcgatg ttaggtaatt   49200
ctgtatttaa agaaggtgca gttattactg gtatgggact agttccacaa ggaactgtaa   49260
ccccaactga cccagacacg attgtaggta atcctaactt attgacctat gcaactatta   49320
gctcatataa ttctaggatt gacacttcat tctataagat tacgggtaga attggtgtta   49380
cttctactgc ttctttagca actagttatc ccggaattca gttatcagta tctggtgtat   49440
caggtggaac ggctacactt agctttagta ttaagcgtga ttcaggtact ttgtataagt   49500
```

```
tagctggtat ctttgataag tcattgacgg tatcagatta ttcaattgat ggtaatacga   49560
ttactactgg gtttgacgat gtaacgacta gtacattagt tacagtagat aataaacaga   49620
ttaacttgtc tgatggtaat agtcataagg ttacagtcac ttttgaagga ttaacttctg   49680
gaacttatcc tattacgtta gaagccaatc cgggatatag cgctttgaat gaagggcaag   49740
ttaacttcac tttagacaat atcaagattg aagaggggga cactgcaact gcttggaagt   49800
tagcagaagt agataaagac ttatctacag atactgaccg aactaagatt tatcgggtac   49860
tagaagggta cgtttatatc aacggtatgg tacgtaggtt cgaacaacag gatattaata   49920
ttactggtgt aggtaatgaa accattggta tcaacattaa cgaagatatt gttactagtg   49980
atgatgataa cagattgcta gattctactt cgggagcagt ttctcagtgg aagagaggtt   50040
cagatagact tcattatacg cttagtttga cttataacga ccctaatgca actaccctat   50100
ataagttatc taatgggtca ttaagcactg atacaacaga ttctacagct tcatctctta   50160
gtgatttatt ggctcgtaga actaatgacc aatctggttc ttacagggta tccggttttg   50220
atatgagttc taaggcagat actcaggatt cttctatggt agacattgtt attgatgctg   50280
gtaatgccta tgtattaggc tatcaggtta agaccggtgt tcctactgta ttaaaagtac   50340
ctaagtcagt cggtacagca gatgcaccag atgaagtatt catttactct gagtctcgac   50400
cagataatgg aaagctttct aatcaaccag ttaagtctgt taatcaggta tctggtaacg   50460
tacaagttac tgatgaacct attaatagag gagcaactat ctcggttgaa gatactttag   50520
ctaatcccgc ttatgagatt gataaggtat atgccaaggg tagtgaaagt tctataacaa   50580
cttatgtgca gggaactgac ttcacaatgg atggtcaagg aaagattaag tggggagcta   50640
cagagagtgc taaagcacct gcggcgggaa ctacttacta tgtttcctat aagtaccaag   50700
caatctttaa aaatggaaca gattatcaac tagatattgc aggtgatgaa gagcgtcaag   50760
ttacaatggt tacattctta ggaatgaacg gattaaaacc agttgaaggt tctcaggttc   50820
atgtttctta tacgtatttc cttgctcgaa ttgatgttgt gactgttgat aagactggta   50880
agtttggagt tgtaaaaggc cagccagata agctttctag tgcaatgcca cctttacaag   50940
ttgacccatt aacattacaa ttaggatata ttactgtatt ccctaatagt gataaagcga   51000
ttactcagtt atctcacaatc actagattac cattttctag tttacaggaa ctaagtaatc   51060
gggtaaggag cttggagtac aattcaagta tttctgcggc aagggattca gctacaagta   51120
atcaaaaccc gcttaattta caggggcag tttatgatga ctttacgggg gttgctaatg   51180
gtgatattgg caacaaggaa tttactgctt cttatttgtt tagtgatggt gcaattacag   51240
tccctacaaa agcatctact ggtattaagc cagatgtgtt agaagtagca tcaagtttgc   51300
ataagttttc gcatacagtt actacaccat ttacagaaac acctatggtt tctcaattat   51360
tagcaacagg tgtagttaat attaataagt accaagtatt taatgttatg ggtactttgg   51420
aaattacacc tgaaattgat acttggacgg aagataatac ttctactgtt tacgtagatg   51480
gtgccgctac aactctcagt tttggtcgtt ggtgggcata tggaacatgg actgatgcta   51540
atggtcatac tacaggtggt gaccattata cgggacaaga tgcttataca gagatgcaag   51600
gtattgtgac aagtgatgga aatgatttaa tcaattatag aaattggtct aatacttctg   51660
gaacacaaac aaaaaattta gggactcaaa cagttgattc tgctattgag tatattcgtc   51720
agcgtgaagt taccttttagt gctaagaact tattaccatt tacagataat atgaagatga   51780
cttttgatgg acaagcagta gatattacgc ctgctgatgg atatgcttct ggtactgata   51840
```

-continued

```
aaggtagtat taaaatagat ggggctggta cagctaaagg tagctttact attcctgagg    51900
gtattcgtac gggtgttcgt gaagttaagc tcgcaggtac aaatggtagt gctattacca    51960
cttatacagc acagggaacg atgcatacag ctacaacaac cattgaacgc cgacatgtaa    52020
cagttaattt ctatgaccce ttagcacaaa gcttcgcagt aactcaggat ggtattttaa    52080
cctccttaaa cttgtggttc aattcaaagc catctagtga tgatattgca aatatttctc    52140
atcgttcaga tgtagttgtt caattacgtg aaatgggaga ccaaggttat cctagtcgta    52200
caattgtttc tgagactacg ttaacgcccg accaaattaa tacttctaca gatgcatctg    52260
tagtaactaa tgttccttta gcagacccag tttctgttaa ggcaggtgaa tcttatgcgt    52320
tagttgttat ttcagattct gataaataca atatgtatgt atctactact gggcaatcac    52380
gtattggtgg aacagaagcc gctgtaggcc aagcttatgt agagggtact ctatttacca    52440
gtgccggttc tcaaacatgg actgctgacc aaaatagtga ccttaagttt gaagttaata    52500
tgggtaagtt ctctgataca ggtactgttg attttgatac tatctatccg ggaaaagaag    52560
tctacaccga tggtttaggt aatccaattc tggataaaga cggtaaagaa attacaatga    52620
ctattgacca acttgtttta ttggcagata gcttgactcc tcagaatacg ggtattgatt    52680
ggcagattaa gattgttact actgaccaac cagacaacga aacggttaat gatgttgatt    52740
ggcaaccact taacgttgct tctgaaattg aattaattaa ggcggctcgt gagattaagt    52800
ttagagcaat ctttaaggct tctagtacct tgtcaccaat tcttgctttg gatagtttat    52860
ctctagcggt attcttgacg gagacatcag gaacttatat ctctaagaat tatgatatgt    52920
ccgcaacacc ctttaatcac attcggttgc aatatgatgg ttatacccce ggaagttcta    52980 ctattaagcc ttattatagt acagatgcag gtaaaacttg gaaagagttt accaacgcta    53040
gaactaagac ggttagttta gatagacact tcactaggta ttactatgat ttacagcttt    53100
atgatttagc tggtggtgac cataccgttg cttctaattt taaggttaag ttagacatga    53160
gtgcacaaag ctcattccag cgtcctcaaa ttaaggcaat gaatgcttct gttactaaac    53220
aggacggata tgattcaggt actgatgatt accaaaaacc ttaatgataa gaatgataag    53280
caggattaat ttcctgctta ttgtacataa tagagttaaa ttaacattga aaggtggttt    53340
tattaagtgg aagataaaga ttttttaaat actttggaaa attggaataa taaagttcta    53400
aatgaacacg acttaattgc agactctagg gagttaatta atcaattaaa tacagctttc    53460
ccttttttag catctaggtc tctagttgtt aataatgact tagtaagcag tacaggggat    53520
tggaacgact tacaaggaaa tacggtatac gcatataagt ccttaaatgg taaaaatgca    53580
ccagatagtc agaaattagg gacaaattat gggattgtct tgactttaca aactcaggat    53640
aggacgctaa ctaatcaatt agtcattcct acgggtagca ctgaactatc tttagcttat    53700
agaagtaaca tggggacttt agtaggaagt acatggtctt atttaactcc tagtgaatta    53760
tattctaatt tacttaagag cgataatgta tttactggtg ttaataagta tatgacaccg    53820
ccacaagata aagatggaaa ttcctttatt actgcacaaa atgttagtca gttagaccca    53880
acaattgttc atggtaaaga cttaacaggg gtagcaaatt tgttatctgt taagaactct    53940
atttcaggtt atttaactag tgaaggaaca ttacagttaa atggtttgtt atatagtgaa    54000
aagactagtg actatattaa ggttgataat caagacccct ataatttaaa tatttatttg    54060
actgttccta atggtaatgc tagttgggta gcattatcct tatttgataa agataagaag    54120
ttcattggta ggattgttcc tacagcagag aaccaagatg gggatacttt tgttaatgca    54180
acgtattggt tattaccaaa aggtgataca agtaaagttc cgacttataa ttttactgat    54240
```

```
gaaactcaat atgtgagaat tagttggaga aattataatg atgcaaaggt tatgttaact    54300
cgtgggtact atccacaaga ttatgtacct aatttagatg atttagcaga tgacaatact    54360
ttagtgcata aatcagatgt tttaggtggt aggaactatt taactaatac ggataatcca    54420
actacgagta accctatcca gttatttgga gaagtagccg acattgatgg taatgttgat    54480
tactctactg ggagagttaa attaactacg gcaacctcag gagaaacgta ctatcgcttc    54540
aatggggcta atagaagaat gccattacaa gcagggcaaa catataccct tagttataat    54600
atgtctggta ctgctggtat atacttggct actcgtatta tttatgcaga ggatactgtt    54660
ccaacgtggg gtgatttact actttcttac cacacatgta caactaaatc tatgaattat    54720
aaggatacct ttaccgttcc agatactgcc ttgtcactga ttgtttctgt tcagatatat    54780
gcggatacta acaaaaatag cgacaatact ggcacaaatt atgttgaatt ttcaaatatt    54840
atgctggaaa agggtgaagt gcaacatgac tgggtacctt caccaaatga ttttccctct    54900
gctgtagacc ctagtgtagc acaaggtaaa gtattaacgg ccaacgatga tatactggcc    54960
ctagacacag gaacttacgg ggtaagagta acagcaccta agaattatcc cacatctaca    55020
ccatatggaa tcgtagtggt caaacagatt agtgaacaga gcaagatggt agaagtatta    55080
gatacttcta acaaacactt agttaatatt tatagcggta gccctatcac atggtctggg    55140
tgggaagttc ctaactcaga tacaatggct actaaatctg atgttcaggc agcagttaat    55200
acagcaacta ctgacatgat gaaaactact gattgggtat atcattcaag tgcagatgac    55260
gctgaaactg cttcgggtaa tgataattta ttccattatt cagatgatta agaacggag    55320
gtaattttat tgagcatata taaaagaac ccttctggtc aggaagaaga aattagttct    55380
atctatcgta aaaatcctaa taccggtgaa gttacagaaa ttacttccat ttataagggc    55440
ggaaagctaa tttatacagt aaacaagcct ttatgggaat ctggtacgtt taattatatt    55500
cttgaaaaac cccaacttag ttcagataat accctgatta gtcataattt taatacagat    55560
aaaaacgttc ctgcgggttt agctagtggc ataaatacaa tttatacagg ccaaaacgat    55620
aaaacattgg gcggaacatc acaaaaattc tttccgagca cttataactt tgtaggtaat    55680
cgttatgtaa ctaaagacaa taaatatata tatgctatta gttttacggg ttctaatatt    55740
agtttgtata agatgtcaac tgtagataat tcagttaaga attctagttt atttatatca    55800
aataatattt ttaatgttta taatactgga tggacacaat ttccaacggc agattctcct    55860
tctggttttta aaacagttaa aacgcctatg ttattatatt ttgtacttac aacaaaaggt    55920
aattctgtag ctagaatggc taatcctgat ggttttgtag agagtggcga tttttcttaaa    55980
gcaaacggtt ctctaaggcc aacattgggt aatcctaata taatccctgt agacaagttt    56040
aagttagcta tagacagtag tgattatgga cagttaagtg gagttcatgg ggggattatc    56100
ggcattattg gcaagagtaa tattattgat gatagtgcta atagttctaa ttatgggaat    56160
gctatttact taactaatgg tgctaaaaca ctagttagta atttagataa caatacaact    56220
aatgcagtag caaacattaa agttacttta gatgtaaaca tgggttctga tagttatagt    56280
gggttgaatc ctatccttaa tccgggaaat gacgttccta tttatataga tgctagtaat    56340
ttaactccct tgggatatta tgagttaccg ggagattctt caaattctat tgaagaacat    56400
tattcctttg caatgccagt gagcttagat aaaaatttcg tggaatatga taaaattaat    56460
aataacattg ctattgttga tattgtacat tatgttagca atggtaattc atccagctct    56520
tctggtgctg atttatgggc tataggtgtg gttactagtg ataagtcttt cctaaaaaaa    56580
```

-continued

```
gaatttggta aagttaatgc aattgcagaa gattatagta attacgataa agaactagta    56640
gtacctacag atggtactag tattaatagt cagacagcat cttttgggaa tactagtata    56700
tcttctaagt attatgttcc taaaaatggt tctatttatg catccataaa agatgtatca    56760
acagatacaa accaagttaa aaaatttaga cttaatggta aagattctaa ttattgggat    56820
tgtactgttg atgggtatac tggggcacaa gtattaggag aagatggtga tttatctgct    56880
gatggaagat ttgttacaag tcctaatata tatatcccta ataaatctat tagagttaaa    56940
tatgtaggat atggagcaat ttctggattt tctaattaca atgttttttg cttttatgat    57000
aaaaatggta acttagttaa ttatcagaaa gtatatggct taggactata ttctgtagta    57060
gatattccac aaggagcttc tatacttaga atttctgtta tgatacgagg ggatatgcca    57120
gcatcttcaa ttcctaagac agtaataact tttgataaca atgttattta tcagatacc     57180 aaaggttatt ctgttaaaga tatggttaaa tacaagcata atttatatat gacagtaacg    57240
aatgatgatt ctggctgggg caagaattta acttcaccaa cagcaggttc taaaattttg    57300
tcctctggtg tggataactc agggaattta tattcattta gaactgatgg ctcaggagca    57360 aataatttt attactggaa tacttttaca agtaaagacg gttcacagat gttggtagct    57420 tcaaccaac actacccggg gggtaataat ttaagtttaa atccatggga taatcaatta    57480
atatgggata gttttaatgc taagatgtta tttgtaggta ataccggacc aatatacagt    57540
ataacttctc taactcatc aggaagtctt ggaggggtaa ctactgctag ctctacgaat     57600
gttaattata ataattatac taatggatac tatccgggat tttgtgttga taactctggt    57660
tcagttatta tgccaaattc ttattataat aaaacaggta ctagtaccat tctaggaact    57720
ttaactaaat attcagtatc tggtacaacg tatacaccag agtggagtgc tacaccaacg    57780
cacttaactg ctactcaggg aattattgac agcaaaatag ataaatctta tattatttgg    57840
gacggtaatg ctaagatagc caaaattgat gctgatggaa atattaaatt tcaagggaat    57900
tatgctttta ctaacgacca aggaaataac actatgcaaa atagaaatca accaactcaa    57960
tttactatct tacctaatgg taatatttta ggtgttagag ttaattatac tggattagct    58020
aatggggtag gaagtgtttc tcaacctacg acttttatttg tatctgttat tgataaagat    58080
aacggaaatg ttttatctgc tagtagtatt attttaacag gagatttaag cggtgctact    58140
aatcgtgttt tattagctaa tgctggatat gtagctgtgg caggaactgc atatagttct    58200
gttaaaatag ttgttaataa ggaagataat agtttaaatt tgaccttttg gaataacaca    58260
ataagctcag gctctgctgg aacaacatct gatgttaggc ccggtattga tagtttatca    58320
gcaagtgata ctgcaatata tgcaggtacg gattcaggac ttgtatttag atataattta    58380
gaggatgaat tttcctataa atgggtatcg catagcatga cggatgttac ctcaaatgtt    58440
ttagtaacgg cgcaggaaaa ttatatttat gtgacaggtg gaaatactac tagccatatg    58500
tctgttatta agatgttgcc taatgggaat ctatatgaat cttatgtaaa agctatgaag    58560
gtttaaattt atattaatag gagtaagagt tgttgacata aattaagtta ataactaaaa    58620
agaaaggaag ttttatagat gtttattttat atcacatttg atgcggatgg ttggattacc    58680
gactatacca aggaaaatag agacgggtat actcgtgctt atgtactcga ttcttggtat    58740 tctgatttt tgagtaattc agacaagttt agatatgatt caacgcgtca agttatcgaa    58800
agtcctaaca acctacctaa gaaatctatt aaagaaattc aggattcttt taataatact    58860
ttaactcagg ttgatacttt aaataaaact ttaggggaaa cacaaaagtc tttggaacaa    58920
ttgcaaacaa ataatgagac tagtgatgca gcgaatagtc aagttacaat gagtttaatt    58980
```

```
tctggacaat tatctctatc tgatagtatg aatgacatta agcagatgtt gacaacatta   59040
acagctaccg aaaagaaac tgctaccgat acagatacga caaataaata aggggagtt     59100 ttataatgga tgaattgcat agagcaatgg taaatacagt tatggtggca tataagtata   59160
agattttaga taatgcttat gtagcaagta aggttaatca tggtttgtat gaagaagatt   59220
ttaaggaaat tacaggtctt gattataatg aatacatggg gattaccacc acaaccactt   59280
caacgactac ggaaaaacca actacaactt caacgacaac aacgagtagc accacggaga   59340
agccaaccac aacatcaaca acgagtacca gcactacttc tacgacttct actacaacga   59400
agccaactac gacaacgact acgagtacaa gtaccagtaa gccaactact acaactacaa   59460
ctagtacaac tacagaagat aattctagtg acactgatta tggcgatagt aattcagaat   59520
catctaaata ataaatatta taagagaaa ttatatttct ctttatctac atagaatctt    59580
aaaagaaagt aggttttaa atggcaacta atttagagtc acaaatgcaa aattataata    59640
gcgaaaactt agatgataac tctaaagtct atgatacaaa agacttgtta aaccagttga   59700
ctaatatatt tcctaattta tataaggaa cactgacagt atccagtcaa cgagtgagtt    59760
taaatacaga ctgggaaact ttaaaggtaa atcagattta tcgtgttgaa gacatttcag   59820
gggttaattc accagataag aataaactgg atggtaatac agcgggaact ttatttgttt   59880
atggagataa aaatttagga actaatttta aaatatttgt gtctggctca atgattgtct   59940
atagacaaca atctgatagt cagtattatt atttaggcaa ggattatgta actaatactg   60000
atttggatac agcaataaaa accttacagg ataaacttac tcagttattg aatgctaaag   60060
cagatgacga tagtgtagtt catttagacg atttacttgg cggtgctaat ttagttctaa   60120
atagtaagtt tgataacaat atggataatt ggcggacttt tggtacttct acaggggctt   60180
ctattgattt tagagtaggg gataaagact gggataatcg tgctaataat ctggttcaca   60240
ttactaaacc taatacagca ggtcaatatg gggttgcaca agataatgtt tcagtagcac   60300
caaacacaga gtatgtattg tctgcgtata gaacaggatt agggagaatt tatttacaaa   60360
atggtaatgg aactactgac ccttaccaac agacgattac caagagggt gcaggttttg    60420 taacccatag atttacaacg ggtaatacaa gaaccacaaa tatttatatt ggctttggtg   60480
aaagagacac aggtcaatta ttcgtatctc tagtaaagct agaaaagggt gtaacttata   60540
gtgattggtc acctgcacca gaagatatta ttgctagtaa taaacggtt gagttagcta    60600 atggtattga tatagatact gtagttaaaa gtggtatata tggatataca agtaataatc   60660
catcaggagc taagcatggt ccagatggac atgatagttg gttttactagaagtaaatg     60720 acttgatggg tgatagcgta aatggtgtac aaaaatacta tgacactaac gatggaactg   60780
gatttattag aatgtggaaa caggataatg gaaatagatt attcacgcca tggacaccta   60840
atgttgatat tggtatagaa tcagatggag ctgattaaa caatagttta caggtgggga    60900 cttttctttag tgctactaaa gtaactaatg ggcccggatt ttataaccaa ggttatgggg   60960
atgttatggt tacgtggacg gttactaaag tttctaatgg tactacccaa gtatataatc   61020
agaatgcata taatcgcaat ggggagtgtg ctacacgtaa ttttgtttcc ggtgcaggat   61080
ggggtagttg gaaaatatta tcaacagacc caagcaagcc tatggatttt ccgggtggaa   61140
taacttctgg gggtgtcgat gtcgcaaccg cggctgattt aaaaagcgtt gcagacaaag   61200
cttggtatca attagacaac aagtatatta cgacaactac tgcaaaggtt cttcctgtga   61260
gcactgtatt atatagagtc gatgatgcta ataaaggct ttatttacaa ggttctattt    61320
```

```
tgctaaattc taatacagtt gagggtgtaa atgtcgactt tagtagtgtt gttaaaacaa   61380
ttttatctag tcaagcacta tctttagggt atgcgagtgg gtggcagaac tggacagatt   61440
tgaaagttca gcttattacc cctgcggcaa taaggattcc tgcttctttt agtggattag   61500
cggttatagg tgtgaatact actccttcat attcagctac tgatatagct tatgtaactt   61560
atgacgaact agtataaaaa aataaatatt cgaaaggaac gattaaatga tagctactag   61620
gaatattatt ttaataagtt ttgatagcac ctagtaatac tctgttaatt attggttgta   61680
attatataga aagtattaaa gagggtggat attaatgaca catcgaatta aatactcctt   61740 atttggaca ggtatcgaga ctatgtcaat tggtatcctg tttcttactc ggcaggattt   61800
actattagaa cataatcagt atgctcccta tctgcaatta gcccagtcag taccaataag   61860
cttactatat attattgttg gttttgttgg ttcactaata gttagtgcag atataaataa   61920
ttataaatgg gttatgttta ttataacaat gtatcaagtg tgctggaata tattatcgtt   61980
agcttttgtt tggcacacct ttatgggtt tggctcacca atagatgtca tttttacatt   62040
ttcaattatt atgagaaatt atacagatgc ttgggcatat agtgctcagt cacaaagaga   62100
aaaggaggac aaagaaaatc taacacttt tctaaacgat aatcaacgtc aacaggaaaa   62160
aataagagag aaagaaaaag agttagaaaa aggaagtagg gatgggaagt gaaagattgg   62220
ataagttata gtgttgcact aatatcagcc ctatctacga ttatattggg tttatattcc   62280
agagtaagca ctagaagaaa aaatacagat agttcagact ttaagcgaga gaacctgtat   62340
gctggggagc ttaaaggaac tttagcacaa attaccagt taacagcaga taagctagac   62400
ttagttaatc aaataattga acttagacag actataggaa atatgaagtt ggacctcgaa   62460
gataaggata atcaaataaa tatacttaag gggagactag ctgaactagg acatccagtt   62520
gatactttag gaagtataag tgattataaa aataaaaatt aaacatgata taattaataa   62580
tagatatata aattagaaag gaagttttat ttatgaatat tgacgcatgg acagaaggat   62640
tgaaattaat taataaccca gtgggatga ttgctattat tgttgtaacg ttagcactta   62700
cgcaagttat taaacaatta cgaatttcta atagatggat gcctttagtc gcggttggtg   62760
ttggtttagt ttgtggttta attattggtg gattaacaac gacaggtgca ttgtttggcg   62820
ctgttgatgg tatttttggct ggttgtgccg cttcgggggt atttaatgta ttaactctat   62880
ttacgagagg agaataacat atgggagcaa agattatttg tgatgtagct gtttggcaac   62940
cttctaattt aacttatttt aaaaaattga agtctaaggg cgtatatggt attattatta   63000
agctaacaga gggaagcaac ccgggaagtg catatggtaa tccaagtgct aaggcacaat   63060
ttaataatgc tcgtgcggca ggactaaaag ttgttggttt ttatcattat gctcgattct   63120
ggggagatag tgatgccgca aatgaagctg attggttcat taagtataag gaaaaggttt   63180
taggaattac tggtaaggat tatgtaatgg tgtgtgatgc cgaagataat agcctaaata   63240
atagtcgggc aggattaact tctaatatta attcatttat taaccgacta aagtctaagg   63300
gttataagcg agtagatacc tactcaggac gttcctttat ccaaactaga acctacccctt   63360 ctaagctagt tactaagaat ttatggattg cttcttatgg tagtgcttct gctggaatga   63420
aatgtggcac ttgcaatat actgataact ttaagggtct aggtgtagat gcttcgttag   63480
actacagtgg attttattct aaggtaaccc cagaagttac aacaaataag aaaccaactt   63540
acttttcatg gaagccttac atggtaactg ctaagactaa aattggcatt tacattgata   63600
aggacctaac gaagttgaaa cgtaagtacc ctgctggaac tgactttaaa gtaagcgagt   63660
taactaagtc atcaaagaga acacctagat ttaagacaac tagtggtttc tatatctctg   63720
```

```
ctaataaaga ttatgttaat aatagctatt acgtagatga tacaattaag gaaattgtta    63780
ctttgaagac tatttggatt tacaaagaag caactcgtaa acatcgagta gctaaattca    63840
gtaaaggaac tgactttgtt attaaggata ttcaagacat cggacatggc ttaacatcct    63900
ttaagactca aagtggttat tggattacaa ccaataagaa atttgttaaa aaagttcatt    63960
gatactatca ccctcaatcc tcctataaat taggggggatt ttttgtatgt tttaaattta    64020
ttaattttgt gatatacttg atgttagaga ttatacataa agaaacgggg gcatttaaat    64080
gattagtgca tcatgtgatt taagcctatc cattaatgat ggacttaaaa aattcttatt    64140
agattgcttg gattatactg agaacattaa aggcagtttt attgcaaagt ttagtggtaa    64200
agatatggaa attgctagtg gttatgaccg gagaacaatt agaagaaata tttataattt    64260
aaaaaatagt caactagtta aatctattca aacgcgtagg ggtcgctctg gtggctatat    64320
tattgagttt aatgatgatt taattcattt taatgtagtt agtaacgttc atacagagaa    64380
ggccccagat gagcctttaa agacgtttaa gcctactcga aaagagaaga aagaatttaa    64440
aggcgaacga gatagaaaat atgattccct gcttaaaact agtaagaata aatatgatgt    64500
attgatggat tatgatggta ctggaaatac ctattatggt tacctattaa gcaaagtata    64560
tgatgcttat gtacaattgt tttctttaga aacatcttta cgttctgaat ataatttttga    64620 tattaaatat tcagagaatt acacacaatt tggtaatggt aaaattattg gctctgctaa    64680
cctaacaact tttactaaac tatacgtatt ctgcaaagaa aataatatta tcctgtttta    64740
ctatatctca gctatttttg aacaagaacg ttttctaact aatcattttta caagagaatt    64800 taaagttcct tatgttaata ccttgttagg gagaaaagat aacttcttat cacaaagaga    64860
gtatgataag aaatatttct ttacagatat taagagtcca cacgagacta ttaggtttgt    64920
tgataaccct gttgtgggta gtattaataa cttattcatg tttcttatct ataagaagtg    64980
ggatattaag gctgtttcgg aatcctatca agaagattta gatagctata cagaagaagt    65040
tattagatta ggctacatgt ctaaagataa ttgtgagttt gaaggaaact atgatgaaat    65100
ctatgaaaag gtaactcgtt cgggtactgg actattagaa gaaattaata aaaagagttc    65160
agatgatgga ttcaatagaa cggttggacg tttgtacgca acttcaatta agggtattcg    65220
attcccttat cgctctggaa ttctatatga tgctaatgtc tctaaatctt atgctagttt    65280
atttaatggt gttaagcaga gtgatattaa gaaatcttta gctaataagg atgacttagt    65340
agttgatgac ttgtattcaa gtgtagttgg atttagtgcc cgtgaaagtc atgtagccac    65400
gggagatatt attaattttg atgatattag agaagagctt atgttgcggt ggcctgcttt    65460
attaaactgg gactctgctg ttgaggttgg aagtttaatt ggagaccaac ttggattatc    65520
taattattta atgacaactg atgaatttaa tgataaacta gaaaaagagg gtcaatcatt    65580 attacctta dgatggttatg gtaaatttaa tttaccttttg ctagttaaag gatttagtaa    65640
aaaatcagca gacttgcgta gtagtgaaaa tagacctgca ttaaagcgat atagccaaga    65700
ggtggaaatt taaaaatgga atcagaagct ttaattcaaa agcaattact atacagagca    65760
ttgagttctc cctacttctc tgttgagatt attggtagaa ataactcagt tcttttttcaa    65820 ggaaatgaaa attatcagat ttatggaaga attttagtta attattataa cgttagtaaa    65880
gaacctatta ctgaggaaac ttttaaacta aaactaacta aagtttgaa ccagttaaat    65940 tctgatggtg atttaggctc cgatgattat actgaatatt ataatgaagt taacgacatc    66000
ttcaattcaa aagtagatac ctcagataca atgacagaag aggttgggaa ctatgttcgt    66060
```

```
aagaagttag gtgaagccgc tattttagag agtgctcggc gttcatcaga tgaagaagat   66120
tttgatttag ttaaagaagt tggcgaacga attgaagaca ttaattcttt agatatttct   66180
ggacaaggaa ataaagttat ttctgtttat gaagattatg aggaaaagaa tgaaatttat   66240
aaagagttag ctagaaataa aatttctatg ggaatcccct ctatggacct tgcaactggt   66300
ggtggcttag ctaagggtga agttggatta attgcggccc gttctggttt tggtaaaaca   66360
actacattaa cttcttttgc taatagttat acgtttaatc atcataatgt aatgtacttt   66420
tcattggaag aaatgaattc tcgtatgttg ttacgttttg accggttagc tttaaataag   66480
cctgctaatt ttattttgga taaagatagt aatttaacag atgagtataa gaagaaatcc   66540
aaggagttct attctactgc actggataag ggaattatta gtaatctttta tttataccga   66600 acgtcacctc ataccattac tattgaccaa attagacaaa ttattttacg agtagaacgt   66660
cagaacaata ttaaattaga tgttgtcttt attgattatc cagacttact gctagacaat   66720
aattcaacag gtaatgaatc ccaagatgga ggtcgtattt tccaagatat tcgtaaaatg   66780
gcccaagata catctacccct aatatggaca gcaactcaat tgaatcgagg ttctggtgac   66840
caagaaacaa tgactttaga taatgttgaa ggttcttatc gtaagaagaa tacggttgaa   66900
tttgctggga cagtaaatcg tacaaaagat gaaaagaaa atgggttctt acgtatttat   66960
atcgataagt tacggaaccc tgatgccttt gatggagata tgctatactt taagtatgat   67020
aaggattcaa tgaacgtt agaagagaaa gataatgatt atgttcagca tctatcttta   67080
ttaaagcaaa ctgaaagttc tacaaaagag tctcgtaaag acaagtttga ggatgaagct   67140
gggaagcgta gtaagaaggc tcaaatgatt aatacgacat tttcagattt accctagaaa   67200
ggtatatgat tattaatggc taagttatat gtaatttcag attttcatgc agatttatat   67260
acacagtatg cccatcctgt agatgataat aggtatcaaa atacaagatt caagcaccaa   67320
atggaggttc ttaatgatat tttaagaaag tcctatacta atgatgctag tattgtattt   67380 aatgagacc tgtttaactc tagggtagac attaatcaga ttgtttatac cggagttgtt   67440
tcgactatta caaattggct acctaaattt aaagataaag gtttaaccat gtatttttta   67500
gctggtaatc atgaccaatt tgataatacc cgaaccccag cttcatcaat tgatgtatttt   67560 aatgagattg cagggtttaa agatactgcg gtttctattg atacaccaga acagtttaac   67620
cttgatgaat ataattatg ttttgttcct tatagtgaag atattgattt tcttaaagat   67680
aaaattaata attcattta tattgataaa gataagaaaa attggttatt tgttcactct   67740
ggtgtagagg gtgcagttca ggggaagtgg aatcatcgtt taggcggggc gtttaaccta   67800
tcagatttgc gatacaagga gtttgatgag gttgtcttag gacattacca caaacgtcag   67860
aaactggctg acaacgtgtt ttacgtagga aatacgatac ctttaaatca taacgatgat   67920
ggtcaggaaa aaggctatta tatttagat acagaaaatc ccccaaggtt tgttaaagta   67980
gaatccccgc tatttgaaac tatcgattta tcagatacgg atttaagtag tgaggaaatt   68040
aatgaattaa tcaagaataa ttatgtacga gtaattacta gtaacaaaga agacttggat   68100
aaattacaag aagagtctag taagaatggg gataatgtaa gtattgctta aagcctgag   68160 ttaaaagata gaactagatt agatattaag gatgactctg gtgtatttga tattgttaaa   68220
gcttatagta agagtaaagg atattcagac ggtgtaacta aaatagcgct aaatgtaatc   68280
caagacgtag ttgaagaggg taatgaataa attggaaaga agattacag ttccactata   68340 taagagtta ttagattcaa gtgcagaggg tgtatttgta tacactaagg ataattgtcc   68400
taaatgtaag atgacaaaac ggattatgaa tactaagggt attgaattta ccgaattatg   68460
```

```
ggtagacatc aataaagatg acgatatttt ggctagttta agaatggcag ggtataattc    68520
ttttcctgta gtagttgtta aatctaaaga agataaagtt aaatcttggt gtgatttcag    68580
gccaaacaac attaacagca ttaattctaa agatgagtag ttaataacta ctcttttttt    68640
tgtggttgca ataactaatt acatgtgcta taatgattat aataggaagc ggggtataat    68700
acattgaagc ttttatcagt aggttttaaa aattttttat cctttggcga tacttataca    68760
gaagttaact taactaacag aggacttgtt ttactagagg gaattaatga agactccgaa    68820
tcatttgcca gtaatggctc tggaaagtca agcttaatct ctgctattgt ctatgggctg    68880
tatgggaaac tacctgatgg aacttctggg gatgaggttg ttaatgataa aacccagaag    68940
aatacgcagg taattttaaa gtttgaacag ggaaataata agcttgttat caagcgttac    69000
cgcaaagata aaaatataaa gaataaagtt attctattta ttaatgatgc agatgctaca    69060
aagtcatcag taaagaaaac gaatgaatat atccaagaaa ttattaaagt agatatgaac    69120
acttatttac aatctgttgt ttttggatta ggaaatatca aaacctttac acaggcaaca    69180
gataaagaga aaaagaagt tcttgaagat attgctaaca tctcaattta taagaaagct    69240
caattagttg ctaaagataa aagcaaagaa attgagtccc aaaaaacaga tgttgagaat    69300
aaattagtaa ctgctaataa ttacattgaa gcttatcaga agtctgttga taattatcaa    69360
gaagggacta ataagctatt agataattta aaagtaatta agagtcgtgt agacaattat    69420
gaaaatcctg ataagttatt aaatgaaatt aaggatagta aggacgcttt aagtaaaaag    69480
gtaaaattat tagaccaagc attagatgac ctaaacaagt caaattactt agaatctgat    69540
gaatataaag ataataaata tatttataat agtatgtcta gtaaaattgg ttctgtaact    69600
tctgaaatta atagaattga taaggatgca gaagaattaa agagtcgttt gattcagatt    69660
actaaccaac cgggtaacga attatattgt acttattgtg gtagtaagtt agacgatgtt    69720
catcgtagta aagagctaaa agtcattaag gataatcttg tcactttaat tagtagcaaa    69780
acaacttata gtaaagagtt gcaagagtta gaagctaaaa aattagatag tgagaaagtt    69840
attgaggatt tagagaacaa gaataaaaat ttttctgagt ctaatagaaa attatcatct    69900
gctagaaata aattaaccga agatatttct agtttaaata ataaagaaaa tgatttaatt    69960
agtaccaaaa atcagtatga tagagatata gaggagttgg ggcatctaaa agaagaacta    70020
gctattaatt ccgtagatga attaaaaaaa caaattaagg atgaaaaaga aaaggtcaag    70080
aaacttaatt tgttaaacgc agagttagaa gataaaagtt ctaattataa aaaagtaatt    70140
gatatgtact cagacaaagg tgttaagtca catgttcttg atttagtact cccttatata    70200
aatcaacggg caaattatta tctgagtatt cttacagata atacaatcaa cattatgcta    70260
tcaaccacta cgactagtca aaaaggtaat gtatctgaaa agctttccgt agaagttaat    70320
aacattaatg gtagcacaga atacaagaga aattctacag gagaaagaaa acgaattgat    70380
ttatcaattt ccttagctct acaggattac gttatgtccc gtagtggaac caaaactaat    70440
tttattgcgt atgatgaagt ttttgatgga ctagatagtg ttggtattga tagactaatg    70500
aatcttttga agaacgagt aaaggaagtc cctagtattt tgttgtcag ccataacaaa    70560
gacttaaaag aactatttga aacctcaata actattaaga agaaacgagg aatttcaaat    70620
attgaataaa aaggtatcgg gtagcttgcc ggaaaacaag tgtggagaaa atgaattaaa    70680
gacttttgca tataaaacaa gtaagggtaa tacttatgtt agggcttctt gctttaacta    70740
taagggaaat ggtgaggaat acaatttacc agtagaaaca ttaattgcat ggtatccttt    70800
```

```
gtatttctat tatgattggg cttatgatta tttgtatgaa aaagttcatt taaactacta    70860
taagggaatt aatcaggtag atagagaatt tattgataat aatgatatta ttacttttga    70920
agattgctta acttttgatg gtaattataa ttttaagact gaaaagaata tcattctaag    70980
agacaatatc attttaatta aagaactaaa taagcaaggt tttgttacct tcgataagtc    71040
tggttattct gtcgaagatg ttgctcgtaa tcaaattaag gtagccaata ttttagatgc    71100
cgtttggact acttgtgaaa agcgtaagta tgagagcaaa aatagtacag aagcttatga    71160
ctctagttat aacgaggaac aaaatagtcg tgaaattcta tcatatatga caaaggatga    71220
agagtaccta tttcaactta tgggtgcggc tactaagatg aatactatta tgagtaaagt    71280
tgttcatgcc aaagtttacg tatcaagtag taaataattc gaaggtgctt aagtaatggt    71340
taagtataat gcaaagaata ttatgtatag actgacagga aataatccag tagaaatttt    71400
atttatcggg gacaaaactg aatacagata tacttgccct atatgtggtt ctgaacataa    71460
taagttttat atggatgcta acacaggtgt atggagttgt tttaaccacg gcggaagtgg    71520
taatctaatt aacttagtta aggaagtatt ggattgtacg acactaaaag ctaaagagtt    71580
cctaatagac agtgaaatga ctgtagagga acaagttcct gaattagcag aagctgataa    71640
tatgtttgat aaagtagcta tcttattagc aaaaaattca gagccagtaa agtcaaatac    71700
aattaataag attatgccta agttgccaac taacactaaa cgactattag ataatttaaa    71760
ctcatacgat gctgttccat tttttagata tttaaaaaaa cgagatgttt ccttacaaga    71820
tattaaagat gcagatatta gatatgtgat taatggagat tttaagactg cttctgataa    71880
agatatgacc atttataact caattatttt tataacacac attaacaaac aaccagttta    71940
ttggaattca aggtcaatag aagccaaccc ttatctaaag tcttttaatg catcaggaaa    72000
agatacagaa tatactcgta gggatgtcgt atttggatta gataaagtat ataataaaga    72060
tattgttgtt tgtgagggtg tatttaacgc tttaatggtt aatgactcta aacatagagg    72120
tgttgcaacc tttggtaagc aggtaacaga tattcaagtt aaagatatta tagaaaaact    72180
tgggtctgaa aataaactta ttttatattt agataatgac gccaagcaag aggaactaaa    72240
attagcagat aaatgtattg agtttggttg tgagccaagt cagctattta tcgttaatag    72300
tccttatgga gatagtgatg ctaatgatat tggtaggaaa aaggcgttaa atttagttaa    72360
taaagctgta aattacaact tagactttag attaaaatat atatttaatt aaataaaaaa    72420
tactatagga aagatggtta ttatatatga tttatgtcaa tgcaccgatt ggggtcggaa    72480
agacccagtt aactgagatt ttatcagagg atttaggaac aaaggcattt tatgaaaagg    72540
tagacgactt aaaaatgcta cacaagttct atgccgtggg ttcagatagt cggtatgctc    72600 tcgccttttcc tttacaagtt gcttttttaa attatcggta tcagcaatta cgtgaaggat    72660
tacatttagc tgaaacggag ggtatgaaaa ataccattta tgattccagt ttattatcag    72720
atggtttaat ggcttataat ttgtttaaac gtggagagtt tccagaagaa gagtttagat    72780
tatatcaaga gctatcacaa acatgcagg ctaatgtgtc aggacatcct tttagcggat    72840
ttcctgatgt agttatttac ttggactgca atttcgaact catgttagaa catattgagg    72900
gtcgcggacg ggatatggaa gttattgata atgataagaa aaattattac catagtgttt    72960
gggaaactta taatgattgg tataattctt atgcagggtc tccggtaatt actattgata    73020 tgaataaaata tgattatgtt aataatttag atgaccgtaa gaatgttcta aactatattg    73080
aatcagaatt aggcaattta gggttgttat ctgctaaaga attggaaaag ttaaccttga    73140
agcatgatac agaatatagt aaggtggcac aagttaatgg atagagaaac ctcagaacat    73200
```

```
caatccttgt tatcctttat tgattatttt aggctaaagc aagttttaga tagtaagggc    73260
actttaccga caatggatat taccttacat gacaaagata aattgacata ttcagaagct    73320
tatgatacgc ttaatttaat tagtaaggat ttaagaaaat atacagacag atatagttca    73380
ttgtctattg atacaattgg aattttatgt actttgttgt cagataaagg tattctaaac    73440
aataaagata ttgaagcaat taaaaaaatt attgtcagtg gttggcaaga aaattaaaga    73500
aagtaaggta attagattat ggcaaaagat tttaatagtg caaagaataa ggaagatatg    73560
caattagcat ttttgtatca tgtaggttca cctttaatga atgaagacca gattactaag    73620
gctaagcaag ttttaaatcg tgaagctaag gttggtgact tactaactgc attagatatt    73680
ccgctgaata gtctacaaaa gcaatattct ttgattgcta agcaattgga tgtcactcaa    73740
tggattattt cgcataagtt ccatgttacc gaagaagagt ggtctaaggc cgaagaagaa    73800
gttgttaagg aaaatgaaat tcaaaagcaa gaagttgcta aggagtttac taagaagcta    73860
aagcaaatta ctaaggaaaa tcaggcgggt attagtgatg atgttaaaaa gaatcctaat    73920
aaggttgtta aggctgattt tggaactaaa aagtaggggg actcattgtg agtgaatcta    73980
gtatttatgt aggttatgaa gacaagttac ctaagactat tgagtatcta aatgcaatta    74040
agggtatttc agttaagaaa ttagcagaaa attatttgct agagtctgat ggggtagtag    74100
atgataaagg caaccccctt gattctatta caggtgtaaa tccagatgag ttagctttag    74160
atgaagttgt tactcaattt aaaaatgcat acaatctatc agaagaccaa aggtatattc    74220
aagcaactct agcaccggga aattccttaa agagtcaagt attagttaat aagctgtata    74280
ctgctacagg tgaagattta gggattacct ttgataataa gctggttagg gataactttg    74340
atttagacaa ttattggtat gaagctctta gcaatggttt ctataatgtt actaaagttt    74400
ctggaaaaca tggggttatt gttttaatta ttttgcctaa tctctcggct attttaacag    74460
attccgaagt agatgatgct attcaatgta tccattcaga agaagggtac aaaaaagcca    74520
aggaagtctt cacaccgatg tttattaata agctaaaaca tgatgcagaa gtctatcagg    74580
attttgataa acgtatgcga attgttgtgc ttgataaaga tgcagatgtt aatagctatt    74640
tagttaataa aatttatttt tctcgtaaag ttagctatgt aactaatgtt ctttcatcta    74700
atggaatgct tagctctggt agtctcggta ttggggcta ctagtatgaa tggaaaaggt    74760
agaaatgcta agggaagcaa ttatgaaaga gagttagcca agaagctgtc taattggaca    74820
ggggaaaatt ttatgcgaac tcttcaatct ggtgctggtg ggactagagc ggttgatgaa    74880
attagaatga ctggcgactt gtttgcacct ttaggaagta acagttcttt ttcttatgaa    74940
gctaagaatc atgcttctac tagattaaat catgtattta ataataatgg agatattcca    75000
gaattttgga acaggcaac tactgactgt cggagagtta gaaaatatgg tttatcccca    75060
atgttattat ttcatgtaac tagagaagca gactacgtac tgttacccta tacagattgg    75120
ttatttgcaa atttagcagt tatgaagcac ttaccttgtc aatctcaggt tacttattat    75180
acggaagaac gaacaaactc tttatatgtt tatagaacga ttttaacaac gttagacgcc    75240
ctatgtacat tagatgcaca agaggtgttt aaacactata aagggttaga ctgggataag    75300
ggtaatccaa ttgagactca tacagacgaa gaattagaaa acgcccagca ggaattaaat    75360
ttatggttaa gcgaagaaaa atcgtcactt tagctacgag atgaatttac tttattaaaa    75420
acaagggaag aaaactcgtt actttagtga cgagtagttc acggttaagt aaggatggag    75480
gatagaaatg aagaagtggt tagatgaaga tggtgtagcc aactttaagt accaaaactc    75540
```

```
actggtaaaa gtaacttcta ctgattttta tggggagtat ttagcacatt ttaattttaa    75600
tagtcccgta ggtaattcag agtttgttat cagtttagaa tataaggatg gattcgtgac    75660
tatccctagt ttaaatgact ccgcctataa cattgatgta cctgtaaaag agcttactaa    75720
gttcttacaa gttattaatg actatatcac ttgcctagag gatgactcta aggaattaga    75780
cctatcaaaa ctatagtatt taattaagca gaatgttata attctgcttt ttttgtgttg    75840
aaaacttatt ctatttggtg tatgataagt agtaacaaga aaggtaggaa cttatctatg    75900
acaaagattt atttggcaac accatggttt aataaggaac agaaggaacg tgtagaacgc    75960
gctaaaagcc tattagctag taatcaaacc gtagatattg tacatttccc ttttgattat    76020
cagtacaaga attcgacaat tgagaataag gatggaatct ttggtagctt agaatggcaa    76080
gtagcaacgt atcagaacga tttatcagct atgggaactg ctgattgtgg tgtatttta    76140
tatgatttag ataatgttga tgatggaact gcatttgaga ttggctatat gcgttctatg    76200
ggtaagcctg ccatcgtagt tactttctca cataaagaag atgtaaaggt taacttaatg    76260
attgctagag gggctaccac ttttatcgat ggtgatactg atttagaaca actatcctcc    76320
tatgacttta atcacttccc atcaaaccca gtaagcacac acgaggtctt ttaagaaagg    76380
agtctaatgt attatgaatt atgcttttgt actaattaaa gcaggaaatg atgttccatt    76440
aggcgtattt aaaaggcatt ctgatgctat tactagtaag ggagagttag aagacaaata    76500
taaaggtaat tttgaagtta tttgttatgc agttcagtca gatattgtaa gtgacccta    76560
tacattcatg aaagcaatcg aggattacta atgggaaaag tattatttta aattagaata    76620
tactataagt taaaggcggt agttataatg agtaaattat tagaaaaaaa caaattagaa    76680
gtagaacgat tagagccaga tggttataca caggaagcgg caaaagatgc tttagaagct    76740
atgaaagtta ttactaagca aggtcacagc ggaacttcat taggtatcct aaaatactac    76800
ttagaccgga tgattgaggg gaagcctta acacccctta caggggaaga ttctgaatgg    76860
gaagaacttg acgaaggcat atatccagat aatcctgaaa ttacagcctg ctatcaaaat    76920
aaacgatatt ctagtgtatt taaggaagtt tacaagagtg gctctgtagc ttgctatgat    76980
attgatgcct atgggtatag tgaagatggt gaggggtctt atgtgggtaa tagtccaaaa    77040
tattatgtag aatttcctta tgcccggt gaacatatgg ttgttgattt tcctacaggg    77100
tttgattatt gggaaaagta tgattatatt cttcatagtc actctaatga atatgaaagt    77160
attgctagaa atgtattttt aaataaccca gaagattgga atatctattg ttcaaaccac    77220
tatggtaaga ctaatgggga ttagcatata tatatcattt aaattaaagg taggtaaata    77280
attaatggat gattgggtag caggtttttt aaccggacta ttagtagtta tttattacc    77340
aactttgttt ggtactatta ctatcggagt catgaacaac ggaactggcc ttgcaaagtt    77400
cttcatgact tgtataattt tgattttgat tatactaatc tggattataa ataaagaata    77460
gggaaataaa taatttgctg gttactggtt gtatgctttt tagaaaagat actgcttaaa    77520
taaatataga gaagtgggaa ctaataatgg gaaaagtatt ttattactat ggaacaatga    77580
agtcatctaa aacagctaat ttgctcatgg tatatcataa ttacgtagaa aaaggaatta    77640
agcctatcct agtaaaaccc tcaacagata ctaggagtgg taacttgcaa gtgtccagtc    77700
gggtaggact atcagaggta gcagatttta aagttcctta tgatggcaat tcccataatt    77760
gggtgtatga gattatggag tctgctatta aggataatcg tcctattctg ctagatgaat    77820
gtcaattttt cagcaaagat tttgttaaag aattatgttc atgggcacat gattttaaca    77880
agcctgttgt agtaatggcc tatggattat tactaaactt tggtggggaa ttgtttgaag    77940
```

```
gctcaaaggc ttggattgaa aattgtgata gtttgcgaga ggttaagact atttgtaagt   78000
attgtggtcg taaggctact cataatgttc tatttattaa caataagcct acctttgata   78060
cttcaagtgg agataccttt attggagata ccgagtatga agttgtttgt tctgaacatt   78120
gggaagaatt acattcagac acccgaaagc aatcaattat taattttaaa gaagactttg   78180
ttaaacgata ctacggtcta taagcatatt aagtgtttat caaaatgaaa gcattttga   78240 agataatgtg catatattta ccaatcgctt tagcttatat tattctatac acgttaacat   78300
atccagtaat aatcttatct gaatatatta gctataagtt agattcatgg aaaggtggta   78360
aaaaagatga cagatagaca aaaaaattat ttacagaaat tgctgagaga agattactct   78420
gtgttaagtg tttcaagtaa agatgctgtt gctgaatacc ttaaattaaa aggtaagtca   78480
atggatgaac tagacaatac agatgcctct atttaattg aattgttagc ttcggcaaat   78540
aagtatacta aaattttagg tatcttaaaa gaaaaaaatt cttataatta aatgtttgta   78600
tttaagctca tgtatatggg cttttttatt tttgaataca caaagtgta taataaaagt   78660 aaaaaggttg gaatatgtat gagagaaata acctcagtga atatagacaa tacatataga   78720
agtgcaaact taaatgtatt gattaaggat agtaacaagt ataaagttgt taatgttaat   78780
agaatgaaag agtctaaaaa aattaattca aactatattt atcgtgtaac ttataatcgt   78840
agaattaatg ataatttagt ttatgattta attgaacata attgtcgatt agattatcat   78900
acaaaaacag ttgtacccctt tcctacatta ttaaatatgc ataacaacaa gaactcagaa   78960
gctatttacg attatcatgg taaatgggaa cagcgtgaga tagagaatat gaatcaagct   79020
tcaatgcttt gtcgaacggc tgtggaagtt aaaattaagg ccggaattac caacccgtat   79080
gctttacttt ataatttatg ggatactcgc tatttagtcg atagagttat ctttaacttt   79140
gaattaatga gcaaaaaaga atatacaatg ctcccggaaa ctgttaaaaa gtattatgaa   79200
ttcaatgaag atttgcagaa gtatcaagca acaccggagg gaaaagtatc ctactataca   79260
aaggttcatg aaattttagc tagatggcaa ttacagttat ggattatgtg tgaagatgaa   79320
gttgatgcta acgaaaccta tacacaaggt atcgcattat cagacgtgat taatacttac   79380
tacagtgtcc ctaaacgtgc acaacaaatg ggggtgtagt gaatgttaat taataaccat   79440
gaattagcta aactaattaa aaaggattat gcaaaaaata caacgattaa agatattcta   79500
tatattttgg aatcagaaca agaagttatt ttaggggctt tacgtgaagg acatactgta   79560
aagattggaa aattatataa gatatatcct aagcacctag aaagtcgtac tcactacgat   79620
ggcattcatc ataaacgcat taatttacca gatagaaccg taattaaaga aatgcaatta   79680
tctgacatta aaaagttgta taattaatag tctatagaag taagggtgt cctttacttc   79740 ttttagtttg tatgataaaa tttaatcata aatatttaaa aggggttaaa gcatgaaatt   79800
aatggttgtg ttagatttca ttagacttaa ttatgttaat gatgatggag aattcgtttt   79860
cttgaatact cgtgcaggta agcgattaac taagattata acatctaaga agtttggggtt   79920 agctcttgat agttcggatg ttgacatttc tttcgcttat cctagagttc caccccttaac   79980 ggttaaagga aaaccgaaaa atattacaca gacaatggga aaaccttatt ttgaaaaact   80040
acaggagcat attgtagagt ataagccaga tatgattatt agttttggaa atacggctgt   80100
tcaagggttg ttaggtaaaa aaggtattga taaactcaga gggattcctg ttcataagaa   80160
ttttagcaat aaaaataatg aggagtttga gacttgggtt gttcctatgt atggtttaga   80220
atcagtagat gtagaaccta gccgctgggg aacaatgtca aaggatgttg acttagttaa   80280
```

```
gaaaattatt catgaaggta ttgaatccat atcttccggg gtaggtaaat atgaattagt    80340
aacagatatt aacagagtaa aagatatttt ttctaacatt ttggttaaaa agaaatactc    80400
tattgtagct gtcgattttg aaacaaacac cctccacggt caataccata atgtgcctaa    80460
tagaaataat ccagaagagt tagtttcagc taaacctatc attttatcta tctcttggga    80520
agagggtcag ggggtttcta tcccagtaga ccatcaattg gcttcttgga ctcctgagca    80580
attggctata attcatgaat tgattaagca attatttatg tcagaacagt ggaaagtatt    80640
gcacaacggt atttttgata ttactttttt gaaggaaaca attgggctta agtattctaa    80700
gaattgtgta gatactctat taatgtatta tattggtgtt actgaggaga ctgacgtaac    80760
taaaacgtta aagggtcttg catatcaata tactaatatg ggtggttatg agtccccact    80820
agatgactat aaacgtaatt ttttgtcaga gcggcataat gcttggattg ctaagatgga    80880
aaaacgcaag gaagaaactg gggagaaata ccgtaaaact gattatgtgc cattagttaa    80940
tgagattgat ggtggggatt tcaattatga atggattcct ttagaaatta tttaccctta    81000
tgctgcggcg gatacggatg cctgcttaag aatttataat aagttaaaga aaatcattaa    81060
agataacgct aagtggacta atcttattta taactattat ccaaagctac aggatgctct    81120
ctcagaagct atgaagaatg gtgtcaaaat tgataaggat tatgcaaaca gaattaaacc    81180
aatttatgag gatgaactta ataaaatatt agaggagatt cgtaaaatac cagaggtcaa    81240
agaatttgaa agcagacgtt taaagattat tagtgatggt gttgttgcta agaagacacc    81300
taaaaaggat agaacagatg gacaagataa agcaatcaaa gaagctaata agttaagagg    81360
tgtcggcagt gatggaagac ctaagtatat gtttaatccg ggttcttcta atgataagaa    81420
atatgtttta tattttatta tgggtatgac tttgccagat agttctgagt tttatacaga    81480
tactgctaaa aacaacggaa aaattggaga taaagcaact tgggagtctt ataaaacgga    81540
taaaaaagcg gctatacctt atttaaaagc caactatgat agtaaattgc ctgaactttt    81600
agagagatat tctagtctag ctaccgtctt aaaagatttc attgtaaagc ttcctaagat    81660
attagatacg catagtttag cacatactag atttattatg acagggactg taacaagtag    81720
gttagcttct agcgggggatt ataacgtgca acaacttcct aggagaacag cagaccccgg    81780
aaactttaaa taccattatc ccgttaaagg tatggtaaca agtagattta atcatggggt    81840 tatttttaaac attgactttg caactttgga aatatatgtt gccgctatgg tatctcaaga    81900
taaagggatg gaacagattc ttttagatgg aaaagattat cacagtgcga ctgcacgtaa    81960
tatttttaat attcctgatg ataaagaagt tttaaaagat gtacgtagtc aagcaaaggc    82020
ggcctcattc ggtaaaaatt aaatgctgac tatctaagta attagatatg caaaaactct    82080
gttaaacggg caaagtaaaa taataactac aataatgaat aacgaatata ctggtaagaa    82140
aggctaagtc caagtagtta tggatagagc tgaccgccgt actaaatgtg tgattagact    82200
tgtatgctct ctatttgtta taattaagta agatgtatca aatggagggg tataataatg    82260
aaaataagta tagaacagcg aaaaacaatt ccatattatc ataatcttta taatcgttta    82320
gcctgcataa ttagtcatat tcgggatagg tgtactaatg taaactgctc tgaatatcat    82380
aattatggtg gccgtggggt tatatttgac cctaagtggt caactacaga agggttctta    82440
gatgatgttg accatataga tggctggaat gaggaaaaat ttattaacca tgaaatacaa    82500
cttgacaagg atataaagta taagggaaat aaactctact caaaggatac ttgcaaatgg    82560
gtatcgcatg gagaaaatat gcatactctg ccatccgttc agagaagttt tggtgcctat    82620
aatttatata ctagggaatt agtaaagttg agttgtgtta aagatttttc tgaaatgtat    82680
```

```
aatctaaatt tatccgtatg ctatgctgtc cttaaaggtc gtaagcataa aagcggagat    82740
tggattatgt ggtacctaga tgataaatgc ccggaggtaa cttattttg tgcaagtaat     82800 gggaaagtaa cgtacaaaga tataaataaa tccagactt ctaagaagct taatgtaatt     82860
aagtctacgg ttgttagagg gtttaaaaag aaaaatccgg gttataagga atggaaattt    82920
ttcgttgaga ctatagattt aaacacacta aaggtctaac gactaagctt ctaggtagct    82980
attcaaatgg gaatagtgag aactagataa gaaaacctta ttaatttaag gaagtaaagc    83040
agagaatcct acaccaaaca gtaggattaa gatatagtct aaacccttt aaatactagg     83100 aaactagggg tactaattgg ttattatgg ggaaggtccc gcaggattag caagtagtga     83160
aaaaatacct ttagatgaag ctactagagt tattgacgga ctaatgagtt cttatcctag    83220
actagagagt acaattaagt attatcagga tatggcaaga tataagggg atgtagagac     83280 aatatcaggc tataggagac gtttaggcac cgttaagtct aaagacaaag gtaaggcatc    83340
cagagcgctt agacagtctt ttaacgcagt tattcagggt tctggtgctt attgtactaa    83400
cagtgccctg attaagttac atgagtattt tttaaagctt aatctaaagt ctttaattgt    83460
ggctacagta catgattcgg ttgttattga tactcatcct gatgaggtta ataaagtagc    83520
aacaatttgt cagtatgtct ttagtcattt agatattcca gaagttgtta ataatgatat    83580
tggtgattta agagttccag atgaattaaa attacctaac aataaattcc gttttccttt    83640
acatggggaa gttgaaattg gagaaaatta taataacgat gttgagtatg acccggatga    83700
acttgctaag tttaaacatc ctgatatgta ttgtcgatat aactatgcta aagttcaaat    83760
aaatgaatat ttaagcaatg gcaagttgac acaaaaagaa tttgatgcta aacttaagaa    83820
gttagaaagc acaaaggaaa ttttcatgca ggcgtgagga gtgaatagat aatgtccgtg    83880
gatattagta atatcaagac tattggaacc attaagtatc aagattatgc aggaaatatt    83940
aaggaaattg atgtggagaa gtctttggct ttttcctccg aggatattcc gtatgagaca    84000
caagctatta agtattatat ggttggacag ttaatgaatc agcttaatcg agaggtggaa    84060
gatgttaaat tacagcaacg tagaattcaa tcgcaattat acttaaagta tgttgcggac    84120
gctaaattaa ttgctttgaa taatggcaag aaacctactg aggggctaat taatgcggca    84180
attaattcag atgatacctt tattgacatt tgtagctctc ttaatgaatt acaggcgaat    84240
gctgagctta tgaaaacctt gtatcgtgca tttgaacaac gtaaggattt aatgcaatct    84300
ttatctgctc aaaagagagt agaatataat attggaagta attcttaaaa tgtctttact    84360
tactccgtat aatgtgttat acttgtataa aataaagaaa gaggtaattt tccgtggact    84420
ttgaaaaaat gttaaagcaa caactaaagg aaacttcaaa tactgaaaca ctgactcgta    84480
agaatgatat ggtagaactt aagaaaaata aagatgcaca tgttcggatt gtacctttag    84540
gcccagataa gtggtttgct aaccaatatc gtcaagtgtt tgtaactttg caccgaaaag    84600
ataatacaga cttagtaca tttttattct tttcagcaga tgatgataaa gaagataaac     84660
tattaaattt agttaaagct attgttgaat taacagtaa gatgagtgct aagtataaga     84720
aggcaaatga taaaattttt ccggatgcag ttaagttaaa taatggtaag tataacgcac    84780
gaattcaaca gcgttatgaa atggtagcta ttaacttact gggtaaggac tttgaccaag    84840
aaactgctaa cggtcgtcca gtattccgaa acttatcagt gagtcgttca gtatacaata    84900
gtttattgac ggcaatggca acttatagca tgggtcgggg aaagaagttt ccaacgcctt    84960
taggtcttgt tgataaggat tactcattcc caattgagat ttcatttgac caaagtgctg    85020
```

```
ttaactatga tgttagtgtt cgtgctgata tgttaattga agagtcatta ccagacgatt    85080
acttagatgt agacgaagac ggtaattatc tatatattga tgacccttac aagttcactc    85140
aacctactaa ggatgcagac agtgattttt atgaacgtgc ttacaaagaa cttaaagaac    85200
gttttgaaac agaatctaaa gcatatgtta aggctatgag tgaaggcaat ccttatgtat    85260
cggatggttt taatggtaat gttaatgctg aaaaggatga tgaaattagc attaaggatg    85320
aagaccttcc attctcagac accacgaaag aaccaaagga accaaccgat agtgtagatg    85380
aagacccatt cgaaaagaaa gatactagtt ctgatgatac agtttcagat actaagcaag    85440
aagatgctga cggttctgtt tcaactaaag atattgaaaa catgacacct gaacagcttc    85500
ttaaatcttt agacttataa aaataatag atattatggc tctggtctac tttgggccag     85560
agctatttta atgctgattt tgtaaattaa gaggggggaca aaatatagtg aatcaaaca    85620 atgatttaat tgctagttta gttaaggaag atagtcgttt tgagacgttt gctgatacgg    85680
atgtcgctga aactaaagat tggttgccaa cccttgtgcc tgcaattgac aatgttatgt    85740 taggggggaat cccgttaacg ggtagaatta ctgaggtatt tggtgagcca agtgttggta    85800
agtctactat ggtaggtaat ctaatttgggg ttgctcaacg tatgggaatt atcccaattt    85860
attttgatat tgaaggaaca acttcacgga ctcgattaga agatttagga gtagataccg    85920
cacatattct aacttaaaag cctgaaaaga aacgtgatgg cacaattacc cctgttacca    85980
ttgaagatgt ttttaaatat atgattagca ctttagctaa gattcataaa gctcgaccta    86040
atcagattgt attatttatt tgggatacgg tcgctatgac tatgagtaat tttgtagcta    86100
accaagatgt tggagaccaa tcagttggta atcaggctcg tgcacttact gagggtgttc    86160
gtaagcttaa tgctaacttg attgctaaca acgggtgtgt aattgcctta aatcaaatgc    86220
gggctgatat tggtggcaat cctatgtatg ctaaagctaa aacagttggt ggcaagggtt    86280
gggaacatga acttagttta cgcttatata tgactcgtaa tggaaaggtt acgcctaatt    86340
ctagcgacac gacagaaatt ggtcatggat ttaagttagc ttttaagaag tctaaagttg    86400
gcgaaaatga tggtgcagtt gctaatgggt atttacttca agagtccggg gttgatattt    86460 actataaatac ctttatgggt gctaaagaag caggacttat taaagcaggt ggtgcatacc    86520
aaaagtatgt tgttttatcc ggagacaata aaggtgagat tattagtaaa acaaccaagg    86580
attggcctga ttatttgcgt tctgatgaag gttatcctgt atttaaggaa atgtggcagt    86640
atctattaaa gaaagaattt cctgaatgtt atcctgcttt atttaatagt aatgctaaaa    86700
ttactgttga agaatttcca ttcactgagg gtatgcagga atactatatt cttaagcaag    86760
aaagtcttgt tcataagaat atgaattacc gtatgtggaa aaaggataat gaaaatgtag    86820
tcaagaaagt tctaaaggat tttactaagg aagctaaaac taagaaagct tctgtatccg    86880
atgataaggg agataagaat taggtatggc acgcagagac tatcacacaa gagaaatgcg    86940
ggaatacgtt atgagcactt taggtaacca tagaccacca cggaacacac cagaaattcc    87000
aattggaatt caagatgtac ggaatagatt tcaacgttcc ttagaacgag gagaccgagt    87060
tattgtatct aagcatatct ataatgaccc tcagagtagt gttgtagtta ctttggataa    87120
gtgttacaac cgattcgttt taggacacac gactaatcgc ttaaatggtg agcatatccc    87180
ttatacaatt aattacttta tgctatttga taaaaactca aagtatgtta ttaaaattga    87240
gggtgagtct gaacgaggat atgttgagac taattagtca tataaattaa tagctattta    87300
aataaaaaag aactttttagt gtataataaa ggtaataata catgtgaaag ttctttttt    87360 gtttggggga aaataaatgg ctaaaaatat tatcggatat aattctaaag acagcaacac    87420
```

```
ttttaattca attggaaact actacggaga taatttgaat tctgttggtt ttgttaaaga   87480
cccagaaaaa ttactatatc agtatgataa cttaattagg aaagagggac gaaaatacgc   87540
gtataaattt tcacgtaaag aagacagaga agacttgttt tcttatgtta aagacgcgtt   87600
catctcttta gttaatgagt atgaccctta ctctggtgtt gactttccgg ttatattaa    87660 gaaaatgtta gattatagag ttaaatattc ttatgtaaaa atgcgacaag gtaaagatac   87720
aagaactgta ctgctaaaac aagacgaaac tgacgtatca gaggtgcttg attttattga   87780
atcctcaaaa gggagaagct tttccaatcg tcaaggtgtc gtgcaatacg aatctaatct   87840
tgacgaaatt gatattagct tattagagat atatgaacag ttagaccaac aaaagccttt   87900
agatgaacta gatattttaa ttcttagata tttagaaaca ggagactcaa ctcttaataa   87960
cttaattaag tatgttaaaa atagaggtag ctatactgca aaggatattc ggtatcatca   88020
tacagagtta aaatatcgta ttgctaagtt atatgggaat gattatatta ataactagat   88080
attaacgaac ggacaaaaat ataggaaaaa taaggaggt cacgatatga gtgacaagtt    88140
agatttaaaa acagtaacaa tggatgattt aaatggtggt tacattactt ttagtcgatt   88200
aagcggttct ggtgatgttt tctataatcg gagtagaggg taccatcatg catttaagat   88260
tgaagacaat aaggcatatg attacaccat ggatgataaa ggtaagctgg ttcaagacac   88320
taagcctatt gtatctttag aagatattaa ggttccagac cctaaagacc caactaagca   88380
ggtaacagtt ccgggtgtac gatatattgc taagagatat aaccaagacc cttatgttct   88440
tcacgatgaa gttcaagagt ctaagattat tggagaccgg ccagcagtag cgtttctaag   88500
tgccttaaag ctatatattc aaagcttaca attctttgct tatgatagtt atgttgcatc   88560
tgaaacagga ctattaggag atttttataa gactggtgac ccagttactc ctactacaac   88620
cacgacaact actacaagta caactaagaa accaacgaca accactacga caacgacaac   88680
tactagcacg actactaaga gtcagacgga ttctgcacaa actgattcag gtaaaacggc   88740
ttaggagggt gattgatagt gacgtatagt aagacagttt ggcattctgg ggacgttatt   88800
gcaaccaact taatgaataa tattgaggaa ggaatttata gttctttgga aacgcgtgtt   88860
gattattggg gtgccgtagg cgataataaa actgatgaca cacaagctat tcagaaggct   88920
ttagattatg ttaaagataa tggtggagga actgtttggg taccttccgg aacgtattta   88980
atcactgcgt caattaagat ttatcctaat gttagtttga aaggcgcggg tatggagaca   89040
accatattcc accaaacgtc ccaagaagca catgttgctg gaacggatat tagcaacgta   89100
acgattaaag atattagttt taacggtaat ggtagtgata ccggaaccgg tggacttatt   89160
tttggaagag aaaataatac aacaacagaa tctttaacta ttgagaatgt tgctattaat   89220
aaggcagggt atggtattaa tgtatcaatt ccaattacga gtagttttac taacgtccgg   89280
gtagttgatg ttgggggtga ctgttttagt ttatatggtg gtggaactag tacaacccta   89340
actaattgtt atgcgctatc ttgtagaaaa gtaggattta atctgagcca attacaatat   89400 tccacccta tatcttgtgt agctgagtat tgtggaattg gattcttact aacttctagt    89460
tgcaataata tttccttaat tgattgtgga tgtgaagaaa accttccacg ttctgaaaat   89520
aatctgcttg gtgatgatta tgttattgat agtgggggtgg gcaatcgatt aatttcttgt   89580
tattcaagaa atgataatca tgccgccgta agcattactg gtggatatgg agtagttgtt   89640
acggggttaa gacacgtagg ttcctctact attggaatct ctactacttc tgatgtaaaa   89700
ggagcaacta ttgtcggtaa cagtgttatg agcccaatta acattgctag tggttcaatt   89760
```

```
ctgaatacag ggactacagc agatattccc aatgcaggta tgtatgatgg aatggtttac   89820
tatgatacag accgaggaat cccactgtac tataaagata aaaagtggtt agatgctaca   89880
gggaaggtag ttgttgatac gactacaact actacgacca ctacaagtag caccacagct   89940
aaaagtgaat aattactaaa agaggtcctt aaagggactt cttttttaata catatatata  90000 gggtataata gaaagaagga attatattga agttcattat ggcacaaccc gctttaaaga   90060
aatttgagta ccaagtggga acagcagtta ataatttaga gatgttgggt gtatctccga   90120
atgatataat cttattattt acagaacatg atactcgaat tccaagagag atggaacaaa   90180
aatttggagt tagaaccttt gtttacccag acgatagaga acaggcggcg cttagctata   90240
tcccatcaat tcgcccatat ctgtggtgga agttcttaga atctaatcct gatatgcaaa   90300
aggaagaatt tatgtatcag gacgctgatg tagtttatcg taaaatacct aacctaaaca   90360
ctttgactaa actatctgca aatcactggt atggctcaga tacagaaagc tataccgggc   90420
cagattattt gaattctaag ggaactgatt ttgttgctag actagcaaag ttcctaggca   90480
ttactagtca agatatatgg aactttagag gtcatgctgt gggtgcacaa tggattatta   90540
aaagtcctac gatagattat tggaaagatg tttattacgc aagctttaat ctatatgcgt   90600
gggtacagaa aatagaacac gaatatgatt atgtgcttat taagaatggt ggaactcagc   90660
aatattggtt tcaaatttgg gtatcagaaa tgattgcaga agcttattta tgtgctaagt   90720
acggtattac aacggaaaag aacccagagc ttaatttctc atggtcttcc gatacaattg   90780
atagatatgc ccaaaacaac ttactacatg atgctggaat tacggaagat gttgctaaag   90840
aaaagcattt attcttcaaa ggggaaagaa agtatgatat tgtttcacct tttgatgaag   90900
atttaagcta cgttaatcca aactactgtt cttatatgta cgcttactgg attaatcaag   90960
caaaacctag atttagacaa taaagacctg agggtctttt ttatttttct attgtaaagc   91020
tataactttt gtcatatatat tagtacataa acaagaaga ggtaagtaag catgaatact    91080
aatgggtatc agactaagga atttactaag ctaaatgaag ctgtagggtg gtttaagaat   91140
aaagggtata cttggtacac gaataccccta gaagacccag aaaaggctgt taagggcctt   91200
ttagagagtt taaaattaaa cgataaaaat aaaaagaata aaagtgaaaa cttggatatt   91260
attgttggaa catacaaaga aaccaattta atttattaca aatattagtt aaatagggg    91320 catatcaata tgacaaataa ctcaaataaa aagataaatg tattcgtaag tcaatcccta   91380
gatgctcaac tagcatgggg ggtgtttgat actaacactc attatgatat ttatttacac   91440
atgggcattc cttatggaga tgttatcaaa caaatagcta aaaatacggg tgattatgaa   91500
atggttatta aatcgggta ctctttaaaa gataagcatg agtatctagc aatgaaagaa    91560
gccctgagtg accagacgat tccaattact tggttaacta ctgaatctaa taagagtat    91620 aaacgggatt tagaaagcac tagtgtatat aagaaggtgc tagataatag taattcctgt   91680
ttacgaatta tggtaaattg gttaggatta aatgagaatc atcagtatat tttaaatacg   91740
tttgattatt accataatcc cttattcaaa tataacactg aatactctaa gttagcttat   91800
attcataaat tatctaacta tagattgaaa cctgaatact ggttagatgc aaattcaaga   91860
gttaaggatg aattacttag tgatgagtta aaacagtggt ggatatatta tctgaatgat   91920
ttagtagatt atactaataa ggttaaaaac actagtagca aaacactaga atgttttaat   91980
tctaaatact cggctgagga agaactatat cctatttta aaagtgagga taagccctta    92040
atttatgtta gagcattaaa aaccggaatc tacatgaaag tcatctcaaa agagttgaa    92100 gcacataata tcatgcatca atatcaacaa tctgtctact ttgataattc aaatgacact   92160
```

```
tctagggaat atgcaagtag cgggttcaaa cgtgcatcta tttatgatat gctgttagat    92220
tccttaaaac aataaattag attagagttc agtccttgct aagtataact tccctcaaaa    92280
atgtggtata attattaagt aaatgattat attattagaa agaagggaa gtttttattt    92340 atgtttaatg gcttttggac aacaattatt gcaacagagg ttgtttattt tatcacaatt    92400
atgggtgagt atatctcagt gtcaacagcg tttaaaatga atcaacgatt agctaaagct    92460
agtgacagaa tcccactatc agatgaaatt tttaataagg aacgcttagg ctatctgtta    92520
gagtggttat ttggtgctat tgttatttta ggtatgggat atttcttatc tatgaataat    92580
gtaatcgggt ggacaattta tattttaggt atgcttgttg ggttctttgt tagaaatatt    92640
ctgtactcaa caatcgctaa taagtattac caaagaaag ttaccaagta tcaagaatct    92700
attatgaata atcaagcttt tccacataaa tcggagtttg aaaatacaga atacggtagt    92760
agtcagcaga agaattttta ggtggtgaat tagttggata ataatttata ttcaggtgaa    92820
aatgattctg tttccgttac ccaaattaga agaggggtta tgatgtcacc ggtagattct    92880
aaaaagcctt tatggattgt agaggaaata ttgaattatc aagaagtctc tatggttgcc    92940
tgctataata ttcaaaaggc atctttgaaa cgttataaac aaactaataa cgctaatatt    93000
ttagttaaat ctggtaaata ctatcgggta aataaagacc ctttcaacaa tttaggtgaa    93060
tctgagttag ctaagattgt tagagcagag tataataaga atagtaaaga caaacaggca    93120
cgagtatata ttccggataa acctattttt attgctcctt taattgtaga tactgatact    93180
tttaatggaa ctttgggggt tgggtttttt gagcgggagc cagttaaacc aactattatt    93240
ggtaataaac aggtatatga acgtggtcgg gcaactggtg tattcttatc tacagataga    93300
atttcatggt tagaaacaaa agttgataaa gctaagctta ttgattcctt aaaacctcaa    93360
attgctagta tgctagacgt tatttacccc gatagcaatg taggggggtag ttccattgag    93420 cagtaaggat gttgataaaa attttttaga gaaaagaatt aagcaagctt tactagacca    93480
acagtatttg tttaagtcct tgggagaatt aggaaactat cgacttattt tgaaaagac    93540 cgcttttcaa ggaaaactta gagcagatgc tttattattt actgagaaaa agggaattat    93600
aggtattgaa attaagaacg aacatgataa cttaaagaga ctgcctaggc aattaagtta    93660
ttactgtcga atatgtaatt atgtttatgt attttgtcac gattctcatt tagagggtgt    93720
agaagaagtt atacgtaagg gtggttataa aagctatgta gggattatat cttactctgt    93780
ttatatggat gaagttactc ccggtattta taaacaagct aaaaaatccc ctaagtttga    93840
cttacattat gccctgactt tgctatggaa gagcgaaata cgcaatatcc tatcaactta    93900
tgttagacat caatctgagt tagtatcaaa aaaattggat ttgagtcata tgagactatc    93960
ttggaaaagt tttcaagttg ttgctggggg caacgctatg gcttctagga gattaagtta    94020
tcgtcaaata atggctaact atattagtac gtttggcgaa cgtaatggaa ctcttttatt    94080
atgccaaaga tatatttatg cagatatgga ccctcaacat tatttaaaat tatatcattt    94140
tggtgataat ttagaagtac cggaggttgt gggatatgaa gctaacggc ttaggaagaa    94200 acagtaaatc ctttactgag cataaattct cttattacaa ttttgggttt attactaaaa    94260
taaataacgc gactgaaaag gatattgagc ttagtgagca ttatggcgta gagttagtta    94320
gcagttttca taaagtaatg attcctttaa ttttcttaga aaagggaaaa gaaagctcat    94380
cagttacctc aacagataca gaatactatg tacacattgg taagatgata ttcggtaaac    94440
taactatttc tattcaacgc tacttgcaag gtaataaagt tgtttatatt tacaagtaca    94500
```

```
aagatagata taagcgacct aagagcggct cacatttagg taaacgagtg gttaatcgaa    94560
acagagaaaa taatcgaaga agtattaagg aatttaaaga aaataatat taatagaatt    94620 ggagattttt atatatgatt ggaattggta tttcagacgc agaattagaa cgctatgtta    94680
agagtatggt taatacacca gattttgagg ggtatttcaa taagcttaag tctggtggag    94740
aacgtgcttt ggctgaacga attacttcag caccgcagtt tcttagacta actaaaaaag    94800
gtgctagagg attcatttta gctttaacag aggatttaaa aacagttacc gttagcttat    94860
ataacccaga cactcaacag gttaagtatt ctttagctag ttatccacta aaagatgtat    94920
ataacacctt agaaagctct gataaagctt ctaaggaaga taaatccgat attaaggtga    94980
atacactaga ggacactaaa accactgaga acgcatctaa gacccctaga aagaagcgtc    95040
agtatactaa gcgtaaaacg acttccacta gcccacaaac aaagaaatca tcaactgcaa    95100
cagcaaattc gaataaatag ttagaaaaag tgctttaggg cacttttttt ttattgattt    95160
aatttaattc atatgctata gttagtatat agaaagaggg ataaaaaatg aactataacc    95220
acattaaaga gatgtcagac tcaaaggtac ttgctatcta tttaacaggt agccatttga    95280
ataacacgta tacagatgat tctgattatg actatttagt tattactcat cccaagcttg    95340
aagatgttat ttctaataac aagataaaaa gtcctcatat tcgagtagac ggagatgacg    95400
ttacttatat tgacctgctt aaatttactc ggatgattat taaatgtgtc ccgaataccg    95460
tagaattatt ctataaatat cctgtgtatt atagtagcca gtattctgct atgggtaatt    95520
ggttatttga taatcgggaa tctatcccct atatcaatcc aatgggattt ttaaaaagct    95580
gtcagggact attaaagagt agtttgagta aaatcaatgg tattagtgat gaggatgtta    95640
aacaggcagt gtatgcttat aaatcctatt catatttatc ctcacaagca atattaggta    95700
aatttgttat tgatttacga gagatttatg aatcatttaa aaactcttta attggttccg    95760
atagtagaaa ttcagaagct agagattatt taaatgcttc catggatgag cttgttaata    95820
gtgatgcggt agtctctttt aaaagtaaac gagatacaaa attaaaggat actctttata    95880
gcaaggtaag agacacactt gattttatc aggaggagtg gtactaatgg atattagtag    95940
tcagctaaca gaaagtccgg gcttaattgc tcttattgat aatcccacag aaggggattt    96000
gttaaaagta atctattctg aaaatatttt agatagtatt attagagatt taccagataa    96060
atgtattatt ccagaagtag caactattgc tctttgtcta tcaaaggagt ggagtaaaga    96120
tagtctaact atttggtttg ataagttttt cccacatgta ttaccagaag accaattaaa    96180
ggtcttaaag tcaatttata aatacttgcc cagtatgggt ggttgggtgg ataaaaatat    96240
tgatttattt atagatttat ttagtcatat tgataaccct agtgaggaac ttattgatta    96300
ttacctaact atatgtatta gaaatggata tttggggatt ggggatgaca acttccctga    96360
cccggatatt cctcgctatc atattattga ttcagcacta acaagtaatc ttgtagggag    96420
acttagtgat agccaacaaa agaaaatcat aaatctactc acgaatcgtc cctatgtcaa    96480
tatagattta agaccccaca ttccctatag aagtggttct ttaaaatcat tctataaaga    96540
ttgggataaa ttcattacca ataaagcaat ttatgaagaa ggaaaaaatc agattgacct    96600
gattgtaaaa gaaatgcagg actatcggga aaaggaaacc aaaatcaaga atagccctaa    96660
agtaactcac tggtggcaaa agcttctttg gaagtaggat aggggagtaa taataatggg    96720
cgttattagt cagctatcag aaattcggga taatcaagat taggagattt tactgtggat    96780
aaagaagagt ttgataaaat catggatgag ctagggatac ctaaagggaa tattaaaaca    96840
atttatgctt gtcctttctg taattcagac gagtatttaa tgtcctctga tgggactct    96900
```

```
atggcctatt ttcccgaaag ttatgagaat aatattttag ttaagtttaa tactattaag    96960
cgtaaagaca cacgagactt atactcaata acagcaggat ttaaaattaa gtattgccca    97020
atgtgtggca gaaagctggt ataaattatg aaaaactgtc cttttttgcaa tattaataat   97080 tcaagtgggt tacctgaaaa gtccttattt ttagaacatt atgactataa gcaaatttac    97140
gcaattggtt caagcgtcca aaaggactgg gatggaaacc ctactttaac tatttggact    97200
tccttaccac gtttaggggt tcaagatgaa tttgaaatta aatattgccc tatgtgtggt    97260
agaaagttat aattagataa aatagaaagg gtgagtcaaa tatgtatacg ggtgttgaaa    97320
atgatttaga taagcttgtt actgcgggtc ttgttagtga atggcattgg gaagcagata    97380
agttaatagt atttgttgat gataacatgt gggaagaatt taaagaggtt actgacggat    97440
tatttgattt agatgatacc ggccttaaag catacattaa gaatgattat atttgcctag    97500
aattaagccc agaagacgac ttcattttat aagaggacgt aagcatggat aaaaatatgt    97560
cagattcaat tgttaggtac aataagccta aagttaataa gggtaaagct attagggcta    97620
aagcccaaca aaatataaaa gcattattac aatacaaatt aagtaagcct aaaaaccaag    97680
ggtatgctgt attaaacaca actgaaaatta tggctatcac taccccttg atgtgttact    97740 actcagactt agatggtaag gtacgcagtg atgaagatat tattaaagat attttaggca    97800
ctactgatga tttgatgact gctccgattc acgttattcc taattatgga agctatcaac    97860
gtattgaaaa agagcttgtg ttgtcaaaag acattagcgt taaaatgtta ttctattctt    97920 acattaaaaac aacagataca aaacttattt atccaggaga acgggagct gttgggtctt    97980 ctatacacaa aataattgca tataaggtta cctcagatat aaagactaat gagttagtat    98040
ttagaaaagc tttggcgttt atagacaaag atatttatca agggtttaga cgctataatc    98100
agagaggata taagcatgga aactaaaatt aaaacattgt cccacttaa tcgggttatt    98160 aaagaaaact atttagttca aagcaactac acatttaaag ttagtcatga aacttatagt    98220
gaagttgtaa cagtaccatt aaagaataag ttagaagttt atcaatggga taagagtgaa    98280
cctcagaata aaaatgacca tcgtccaatt gatttacatt tggctgtagc agataatgac    98340
ttttcctatc aagcatcgta tttagaacta caacaatttg atgattattt ggatagttta    98400
caagtagtag atgagtctgt attattagat ggcgcaaagg attttcatat taagttggt    98460 gtagaaacta ctcgaacaac ttataagatt aaagatacta atttaattaa gttcacttat    98520
gaagatgcta acggaggtat tattagactc ctattcgcaa gttctcctag tgaccaattc    98580
ttactagact tcacgcaata taattaaat atgagtaatc tatatgcaat tcttgaccta    98640
atggctaatg gactgtttgg ctacttccaa ggatttaatt tcagattaaa ggataattca    98700
agccttgaaa aaagttattc agtgatgcta aattctaggg agactctacg tagattagtg    98760
tttaaacccc aaaaggataa ctttattatg ctaacgactg accgaactac tttgtcaatt    98820
cgtatggcag atattgaaaa tattgctttt actttaccgt ctttagaaac tggattagat    98880
tcagtatatc tagggctaga agtcaaagga aaaggttata tctatttatg gttaggttac    98940
taattcaaac tcagtcaaga caattttttat atcacatttt agtgtagtat tttatacaaa    99000
tattctttat aatccataaa tatactgaat atatcttatt ttattcatat aaattataga    99060
ttaaaaaacc acatttattg gctatagttg ttgtcatatc aacaatcaac aaaattaatt    99120
caacattatt ctgctttttg aatattgaat aggtgatatt cattatatta ctaactgtag    99180
acgtaaaact acgataatt actaatctta cagggataag tgtataatga aattaaagag    99240
```

```
tatacaagta ttcaatatta aaaggagagt gcaaatgttg tatggcaaaa ggaaataatg    99300
ttacactaaa aatgttgtat aagaataagc tggtttatac taaaactatc gctatgattg    99360
atagtgggaa gacttttgat tttattctaa agtatttaga agaagaggaa ttacctattt    99420
cacggggaag tctagctaac cttaaagcta aattaaagga gtctagggag actggtgtgc    99480
cgcttgctga tttaattgac cgtagaaaga agagtagtat tacccaagta agtcctagaa    99540
atatcgaggg ttacaggggt gactctaatg aagttcagca agtagttaaa gtagctaaac    99600
agaattggtg gtctactgac caagttttag atagtattat tactaaaggt gtagatagct    99660
tacagtatat ggatgttatt gatttaccta tgcttctaaa ggctgtggaa atgaaagata    99720
ggaaccatgc atctgatagc cacgggttaa gcttagaagc catgaaacag tatcagctaa    99780
ttatgcaagc tcaagcagaa gccttagcta agttcttat gagttatgtg ccagaagata    99840
aacaggcaga agcttggaaa gaattggata agcaacaagc agaaattcta aaagatgtta    99900
aattaagtcc agaaggtaag aaattaatct tatctctaca aaaggaaggt attaatattg    99960
actaaaaata ttaagaaat tatttcaggt tataaatcta acttacaaca tgcaactgtt   100020
acgcgagaac aaactatgac ctacacaatg acagcaaaag taggttctga aaaaagcatg   100080
ctttttttca actttaattc tcagatgtta actgttaaat caggtaagct aacttatgcc   100140
gttatgttac ccgcagatac attttctaaa gtagatttaa ctgatgggga tgctttaaat   100200
gcagtattag ataatctgac gttcttatta gattcttctt acgattatga catgcacatc   100260
tttgactacc acaaatgctt gtctgatgtg tcttcaattg ttacagataa ggaggatacg   100320
cttaaaggta agttactatc aacccttca agtaaagagt tatctagcaa gaaagagtat   100380
ctaaatactt tggttacttt cgcagaaaag aaccattata cgtatggata taaattcgtt   100440
gattgtggtt taagttatag tgacgatgta attatttggt cacaagcttt ggttatgcta   100500
cagtcattct tacgtgaacg gagactactt gatggattag ctaaccttgg gtaaagtata   100560
atagagggtg accaccctac tagtagcaaa acgctggaac actattagca aaatgccaga   100620
acgaagtata ttaaaaataa gattatttta ctagtagcaa aacgccagag cactagtagc   100680
aaaacgctgg aacaaatatt taaaaatact gtagagacta ttaataacta atccctacag   100740
tatttttgta tagttattaa aaaatattct ggaccttga cagggacctt atctcgtgta   100800
tactagaatt atcaaataaa gagaagggaa gcacaaaaat gaaactattt aaatatgatt   100860
tatcagctaa aggtaagagc aataccaaga acgatactaa tagcttcacg tatatgcaac   100920
ttcgcgactg ggtatatgat gttttagata taggggagtt taaacctcaa ccaattactc   100980
tagcccacct aactaagact aaaggcagta gtcccgatgt gtatacgagt aactttgaca   101040
tttataaagt agggttaggc ttatataact actatagtaa gggaacgagc attcaattat   101100
acggtgatac ggataaaaat attttattga gattaggcct tgacaagtac ctgtatatag   101160
attattatac aggtgaggtg ttggaagaaa tcagtagaag tgaagtagag aaaaaagttc   101220
ctgtacaaaa atggaattta gaaagtgaga tgtacaaaca ggcagttaaa atgtttacta   101280
gcaatttaaa taataagaaa ggggttggaa gccatggcaa ttcatgaacg acccgataat   101340
aaacctaaag accggcaggg ggctaatgat aagcgaaata gaaatatcgt tattaaaaga   101400
attattttat ggatggtggt tattgggata gtaattaagt tttggaattt cttcgtttat   101460
gtagggacaa caagtatttt actattcttt acaggtgtag gaatcacttg gttcttatgg   101520
tatctagcat acacacaatt ttatgataat cgtaggaggt aaaaacaaat ggaatacgaa   101580
atcgcaaaca gttatgattt agcaaagaca ttaaaagagt gccgaatcaa tcagggaatc   101640
```

```
actcaaacgg aaatggcact aaaatcagat tttagacaac cacaactatc atcaattgaa   101700
aagggcgacc ggcaactctt agtggatacg ctacttaaat atctggataa catcaatggt   101760
catctttata tcaagatttg atagttaaca tttaatatta gaaagaggtt attaaaatga   101820
ttaaagaaaa atattctagt gaaattattg actataccgc aagtctacta aaagactggt   101880
taaaagtcta ttcaagtgct gatgacttta tggaaaatga actactatct tccggttact   101940
taatcagtca aactgatggg gtggacgtac tgtataccga tggtgatgaa aataaaacgg   102000
tatcagagca actgctagac tatctaactt ataatgtacc aagtgaagaa ctgacaggcg   102060
atggactact cgatatggta gatgattttt tcgctaacgc tgtaattgcc tatattttag   102120
aagatgatga aattgtggta tataatctaa ataagtgtt gacaagttat tctatacttg   102180
atatactaag tatgtaataa agatatggaa agggagtttt aaagatggca gaaacagaat   102240
tgattttaaa gggtgttgac ctagacaggg gttctgaatt atttgacgta attcataagg   102300
cagacggtga cacgctgtat aaaaaatcca gcctacattt agtcatcaaa aagagcacag   102360
ttaaaaatta tacagatgat aaaatcatta ttcacaactt ttataacatc ttttataata   102420
atccagataa tggaattatc gttgattttc gggtaaacaa tgggagcaaa gattctgttt   102480
ggtataatcc tcaaattatg ctagacgcta tgcagtatac cggtagctat caaaacgtaa   102540
gacagtttaa cactaatctg attcatatgg gacatgcaca gaaagagctt aaccaagtta   102600
tggacttgct agactcttta gggtttaagc tagtcatgga taagtatatg tgggacgcaa   102660
tgaattaata taaattcgaa atttagtatt gacaaggtat tcttttaatg ttatacttga   102720
ttcatagata agggaaggaa gttttaaaaa tgacagcaag cgaaaagtta caaaaattaa   102780
tggataatga tgaacttacc gaaagccaac aagatagcct tatggattat aatgtttatc   102840
aagttgataa cgcacgggac ttatttaagg aaatgcttaa cgaaaatact agcccttta   102900 gtagagaggt tactaatggc ttatctgatg cagatattat tacaacccct tacaacttat   102960
taaagtattc tagtgttgac tatgttgttt gtgacggtta taatggaact gttgagctat   103020
tagatgatga tactttagaa gatattcttg atgtagaata gttaaaatag ttgttgacaa   103080
gatattcaaa tgatggtata cttaactcat aaataagaaa aggaagtttt aaaaatgaca   103140
acaaatacaa aggtagcttt aaatgaattg acggaaaatg atactgcaag actatttgaa   103200
aattctaaag tttgggaaaa ggttactagt gaatttagca atgacgtttc tgtgatgtta   103260 aatgattta tttcagaact aaaggggtta ggtaattata gtattaataa tagcagcgac   103320
caatataatt gtttgtatgt agacaaccct tattacttct taagcagttt aaaacgtgct   103380
tgcggttact atgctgttgt attgtctgat gaacaactta ataaagctag tgaattggtt   103440
tcggaatatg aaaatagtgt aaataacgac caacaggaaa agctaacgga agatatgttt   103500
aacttatcca atgagtatgc agaaatgtta ttagattcca tggtggcgga atacgatgct   103560
atctataata aagatgagtt aaaagaatac atgcaagatg agttaccaga aatgtacccg   103620
gacggtgctt actataatcg tgaagataat tcaattcact acatgattaa agactaataa   103680 aagggtgta taaactatga aactatctgc taaagatgtt gaagccatta tcaaagattc   103740
taattataag aaccaacaag aaattgaaga agttacgac tgtggttcac tagatatata   103800
cttaaatgaa tcatcagcta aaaagatat tggtgggaat cgtgaatact cccaattaga   103860
aaagactttg cttcctagta aaaaggttgt tatctattac gattaatatc aaatttgttg   103920
ttgacaagtt attcaatcaa tgttatactt aactcatagt aaagagagga agttattaaa   103980
```

```
atgtatcaag ttaaagtgtt tgttggtact catacattag agcaggatat taattcatgg   104040
ttagagaaaa atatggcaat tgaattaatg gatattaaat ataatattga tagcgatgga   104100
actaatgact atgctttgat tatttacaag aagtaataag ggggttgcta aaatgttaga   104160
gaataaagtt aaaaacgaag acttgctaaa aattgctaat agtttaaaag atgaaatggg   104220
tgcggataag ctattaagtg ccttaatgaa tgaaatgcgt ccggaagagt tgcaaactta   104280
tttagcaatc attagtgact attattatat gggtatgctg gaagattaat tttaaaaagg   104340
agatatatta aaatggcatc atatttaaaa gtaaagacg ttttaaccgt tgccttacaa   104400
gatgataata gctcaatttt cggtggtact gcttttccta atgaaactgt agcggatttt   104460
atgcaatgtg tagagtatac cgatatgggt gacggtgata ttctaacccct aatagcccg   104520 ttaccagtct aaacagagc tttaattcaa tcaggtattt tacctttgag tgatgagtta   104580
taaaatattt gacatttgac atttgacatt tgacatttgg catttgataa atcttatata   104640
taaaaggggt aagcttatgc gaattgaaga ccatagggaa gctaaagcac agaaagacgt   104700
ataccaagtt ggaaatatta ttaaaaatgg tgtagattat ttcctagttt gtaggtatcg   104760
tattgctaag gggttctgtc tagttaattt aagaaatgat aaattgttta attccacccc   104820
ctataagact ttagacatgt tagctttcgg ctatattaat ccagatgatg aactagtaaa   104880
gggtaaaatt gacttatctt atctaattcc cgaaaaccct atttcaaata aagacttgta   104940
tcaagtcgga aatatcattg aatacgtaaa tacagatgag tttgatggtc aaggttacta   105000
tctagtatgt agtaccctat tagataaaca gtatgcttta gttaatgttc gaacatctac   105060
tattatcggt acttataatt ctttgcaaga atgattatt cgtattgcaa tgcctacgaa   105120
ctcattagta cgaggtaagc tagttctgga agattaaata ataactacta gtctatagat   105180
tacttaagta tagagcttat tatatagctt gggtagtcta ttttttgttg tgctaagcat   105240
tagtagtata tatagatagg tatctaattc gtatatacag aatcatacag ataagctagt   105300 tttttgattaa aagtaaaagt atttagtcta aagtatacta agggagcata agagcataag   105360
gttataagag taggctttga gtataaagag atataaggct ggactactta actataatag   105420
ggtaggttga actaagtaat caaatatata aatagatatt gatagatact agacttatta   105480
ggtagattat attaattcaa tagactatga tataagaagt aggaacataa atcctaatac   105540
ttagcttagt acctataaga gatacttagc ttaataatta actacttgac tacttgggta   105600
ctcaacttaa cctagtaggg agataaaaaa gtaagatata agagtaagat acctaactta   105660
ataattaact acttgattac ttgggtactc aacttaacct aatacttaaa ataagaaata   105720
gaaaacaaag aagaacaaaa taaaacaagt acctagggta cccccttgcta gtgtggtaaa   105780 aaaaccacta ttagcaagtt ggtcacttag ttactcaact aactaaccta atacagataa   105840
atgtatttag gtatattcct taataacctt gacataaagg catttgtata ctatactata   105900
cagtatagag gtaaaattag gttagttaca tgactaacta acctatatta ttttaaagta   105960
tttcagaaag taccttgaca tagtatgtat actacggtat aattatctat gtaaggtaat   106020
aaataagtat tgactaacaa aggggaact ataaacatga gtatgaaaaa taatcgaaca   106080
ttactggtag gcagtgaact agctaatact cccaagatta gcttatcaag cctagttaat   106140
gagttagatg tagctattaa atatatgaag cctagcgtac aagagttagt ggactattgg   106200
gtgtctaaag gaacaaagt tatcttat tcgtgtaggga cgactagcta caagctacag   106260
gtattagact atgtggctga actatcaaga ctagagtata aagataatga aaaacaagc   106320 actactttac ttagtagtat gacaactggt aatcatggat ttattactta tgaatcagag   106380
```

```
ctaattacca tcgttttaaa cgagattatg gatatttggt aaaattatag atataccaat    106440
taggttttag gtaccttagt ttaattttt tacgtaagat tcatatatag gagacaatgc    106500 tttttaaaa acaaatgccc ttatatcagc attcttgatt ttagggtgca aaagtaaggt    106560
taatgtatac caatttattt ttatctgctt atggttgact taagcagggt aaccggctat    106620
aataaaatag atataaactt atataaatac ttaaagggc tgtaaaaagt aattaaacgt    106680
acttaattta gcttataagg gagtttaaat gcaatctaaa gtatttatac ctaaatgaat    106740
taaaacggct tagaacggat tatatgagct tataaagtaa tactaaatta gttgttgact    106800
tactaaggtt acttatgata tactaattaa gagtaacgat aacaaagcac catagtatca    106860
aagcagaata aagatatta agtagttagc tatatagtgt agttagctac tttttattta    106920
tttaaaataa tgcttgactt agtattcaaa ttagtatata ctaagcagtg taataaaggt    106980
tagcaagtta aggactaaag aactaataag tatcaaataa agttaaatta gttcttgact    107040
aactattcaa atgatgatat actaagtatg taataaagaa aggacgtaac taatatgaaa    107100
actacaaaac agtatttaac caaccacagc tatttaaatt gtaaacaaat taccactgct    107160
attaaccgtg cgactacagg attaatcaat aaggctagtc gtggggact atatgaaaac    107220 tttggtcaag tagaggttcg tagcattaaa gataagttta ttgatatttc cgactattcg    107280
gaaaatatga ataacaaccg tgatgagtta ttaatgttta gtcactggtg cagtaattac    107340
caaggataaa tttaaaataa gtattgacaa agtattcaaa tgatgatata cttaattcat    107400
ggtaaaggaa agggagtttt atagatgttt aaagtagtga ccagttttaaa tgagggcgtg    107460 aaagataccg tacaaagttt cattactttg gataatattc ctattatgga gcttcccgaa    107520
gtttataagc cggacaacaa agaagattat actttgctat ggaaaaatgg ggtaattgat    107580
tttatgctgg aacagggtga aaatgaaata tataagcacg gtatatcca ccctatcatt    107640 atccctgttg agggtaacta caaattaatg caggaatatc ataaagaaat gcttgacaga    107700
ctattcaact gatgatatac ttagtatgta ataaagaaag ggaaaggaag ttttaaagat    107760
gattaagaaa aactatttag aaattgatac tgatgtacgg ggcaatgagg tctatactaa    107820
aaagactaat gaaagcttac caatgtactt aggaacaatg aagttaatca atggtatctg    107880
gaatctagta agcgctgatg aaagcggaaa tgttgtagcg gttgaatatg aaactactgc    107940
actgggcact ctgaacgctt taatgatga acttaagtct attagcattg aaaatgtaca    108000 aaattaaat gattttaaca ctgctaatat tggtaacatt cttgcctttg tagaataaga    108060
ctatataaaa aagggagtat gattaattat gaaaaattta gataaagatg aactgatgga    108120
aattgccgaa aagttagaag ctgaaatggg tcaacatgat ttattactag caatcctatt    108180
agcaacgcct agtgacgagc tacaattaac tttagaatat attaaccgct gttatgaagt    108240
cggagtaaaa ggtatctaag tattaaaatt agttcttgac taactattca aagatgata    108300 taataatcac agtaagaaa gggagttta taaatgttaa ataaaacaaa ggaatcacaa    108360
ggattatttc cagatgagtt cgaccgtatt cggttatggt ctaaagacca caatgaaagt    108420
gcatatggaa aagatgaaaa tggggaacta actattttca gctaccggga taatgatggt    108480
ggcctagatg ttaagcagta cctcaatgac tctgaatggc gattaaatac ttactcaaag    108540
tcgggtactc ttctaactac agattacgga aaagacttac cagaataaaa aagttattga    108600
cttagtattc aaatgatgat atactaatca tagttaagaa aggaagttct ataaatgact    108660
acaagtaaat ctacagatac aaactttatt gttcaactag ctacggattc agatacttat    108720
```

```
attcagtatg attatctaac tgaaagtaat ccatttagct tagttaactt aaatggtgct  108780
actatgttta ctgcaaccag ttgggataag gttcgcggta atatgcctaa atactctgaa  108840
aacaatccaa tgtttatcaa agattaatta aattagttct tgacttacta ttcaatcaat  108900
gatatactta ttatagttaa gaaaggaagt tactaaaatg acaagtaaat ttacagaaga  108960
acaacgagaa aaggctatgt acttttaat gaataatgac ggtttgaata ttatgcaact  109020
taaagaattt atggccgttt atgaaccgta tgagattgcc aagatggttg attgggcaga  109080
tttaaaacta gattgtgatt atattagaat aaccgattat tattcagaaa cacaagaagc  109140
taacacagca tatgatctca tttctgatga agaaattgaa gaagccctag agcaattgca  109200
gtaaggggat agttataaat cttaaattag ttcttgactc actattcaaa taatgatata  109260
cttatcacag taaagaaagg gagttttaca gatgactgat aaatttacag aagaagaaat  109320
tgataaggca attgaattta tggtagataa tggcgatttg gatattatgc cacttgaaga  109380
gtttatgact agtttcgaac catatgaaat tgctaaaatg gtcaagttag ctggtctaaa  109440
tttagactat aattatattc gggtaaatac ttactatgaa gatacacaag aagcagacac  109500
atcggacgaa ctaatttctg ataaagagat tgaagaagct ttaaatgagt tacaatagag  109560
ggggtattct tatgactaaa ttagatacag aaaaactaat aaatgaaact aacgatgatg  109620
aaattgcttg tatgctttat aatattgaaa cgtataagga tattaatgac tatactcact  109680
atactaacaa tgatgaaaat gacttaaaag aattgcaaga agatggctgg gtgttggata  109740
ttacaccggg aacatataac ggggcattag ataaaacgga ctatagcgag ttaaccactg  109800
caaacattta tagtgtttta cttgaagatg tttacgaaga gggtttccaa gagttgcttg  109860
aagacgtgta tgaagaacct aacgcaaggg aagcccggca ggttcgctta ttaacggaat  109920
tttataacgt gtttaccatt gggcaacact tatatatcga ttatgattag tagaatataa  109980
gcaaatgggt ctagctatat agctaagcct tttttatttg tttaaaataa gggttgactc  110040
aatattcaat caatgttata cttagtatgt aataaagata aaggaggtta agaaagcaga  110100
atacggattc aaggttacat agtcgaagcc taaactagat atatttagag tagaataaaa  110160
tacttttata aaaaggtgca gacttcccta atcatatctg gtacggtttg accatttacc  110220
ggtgttcctt acttatctat aatcctatta tacaattctt tatatagtct gtcaatagct  110280
aatggtaaat taatttaatt agtcttaaaa atagcttcta acgtgttta agcatattag  110340 gtataattaa tccagataca gcttaaaacg tcttacataa gcttacagac accttagaat  110400
ggattctgtg gggtatttac ctattaagaa taatatttat taaattagct attgacttag  110460
cttaatctta gctgtatagt aataagcata gatgatactt ggtacacaat aacaattggt  110520
agtcttatga taacggacta cctatacata ttagaaatta taaataagg gttgacttag  110580 tattcaactg atgttatact tgattcataa ataagaaaag gaagtcttta taatgactaa  110640
attaaatagt cgtgtagtcc gcttaacaac tggtatggta tttaacttaa aggaagaatc  110700
aattagtctt accggctgtg cttatgcagg gtgcaaagta accattaaag atattgaact  110760
gttttcagat agtttccttg gatttgctgg tcaaatgaat cagttagcag acacttactt  110820
aaatgattct gacttagcta gtgccatctg gaataatata ctggagttac ttatcaatgt  110880
agaatacggt ggtttagagg gagtcagctt ttcctaataa tatttaaata gttcttgaca  110940
aagtattcaa tagatgttat aattgattca tagataaggg aaaggaagtt actataatga  111000
ctgatacaga aacgttaaca actgcaattg aatatgtaaa gaccatgaaa cactatgaaa  111060
cccgcttaca gtttcttttg ggaaaggcta ttgatggggg tactttacag tatacttgta  111120
```

```
ctattgataa ttgcgaatac tatgctaagt ttgtatgtga aactattaag tcaagcaagg   111180
taaaccctga tgggaatatc gaacatttat gccacacgtc agttaatatg attacagaaa   111240
ctaattttat gaaaaccggt ttgcagattg tttcaattaa gtctatatag aaaggaagtt   111300
cttaataatg acaccaaaca aatttacagt actacagcaa gcggatgcac aggaatggtt   111360
agagaaccat agttttgtat atattactac accagaagaa ttaatcaaat cacagacacc   111420
tagcgaatta gctaagatta tcaagcaatc tgatttatct ttactatgtg aatatattcg   111480
ggtcggatat tactattata attataaaga agccgacact gtagctgaat tgattactga   111540
tgaagaaata gaagaagctc ttattgaatt aaataaggaa taacggttga cttattataa   111600
ttagtattat ataataggtt tatagataag aaaggggctt tacatatgag tattaattta   111660
ggtactttaa ttgtatttct attagctggt tggggactga ttgacttagt taataaagcc   111720
ataggtctta actggaaacg cgtgttctct gaatggtttg aagactaatt aaaataagtg   111780
ttgactaact attcaactga tgttatactt agtatgtaat aaagaaaggg atgttcttac   111840
ttatgaaatt agattttgtc catattgata agaaagtctg gggtatctgg ggtagtcgta   111900
acggtatcaa atataactat ctaggatata tgagattcga taatacttct aagttatggt   111960
actttatgaa agatgattta gaaagcaaca gacaagactt acagcatacc ttaaaagata   112020
gcgttaaaag cattaagcta attcttaaat agttcttgac taactattca atagatgtta   112080
tacttatcac agttaaggaa aggaagtttt acacatgact aaattagatg aacgagtagc   112140
acaagcaatt gatggtgaag catttgaaca acgggcaagc gtttatattg aagaaattga   112200
caactacgca acggcttact atacggttca ggttgtatat ccacaagaat agctgatga   112260 tttaggtatc actgatgagc ttaaccagtt agctaaaaaa tatcccgatg atgatacagc   112320
gttatctgat aatgtgtggt acgtggtaag cgattattta actagtcatc cctataatga   112380
gccactatta ggaatcgaat aatatacaat tatctattga caaactattc aaataatgat   112440
atactaatca cagttaagaa agggagtttt aaaaatgact ttagttaatt cgttagtacc   112500
acgggaactt gtaagtatta ctcagcatgg tagctggtat caagttgctt ttatgaatga   112560
aaatgtactt aatacaatta cggcacaagg gattaagaaa actaagcagg caattagata   112620
ctttaatatc gttcatacta aggggacacc gatggtgtta ggtaaagatt tgtatctatc   112680
tacttttatg gactagggag taagctatgc ttaaattaga taatatgatt aagttttata   112740
tacctaaaat ggatagtaac tttcagataa ctaacttata taccgaggtt ggctgtaggt   112800
ttgactcagc acgtcagatt agtatatatg atagctatac tctgcataga agtgaaacaa   112860
ctacttatat agaagaggta aaggttattc agctatctgt taatcagatt acaatgggtg   112920
tattacaaga tatgcaacag cttgttgact atatgtttat ctgggataac catcagtcag   112980
ttagtgttga ggtaaacggg gtgctatatg tactagagaa taccgaagac ttttacgagt   113040
tacaagctga tgtgtttcaa ctcatataaa ggtgcttaca tttaattatg taggtatctt   113100
ttttatatag gggatgtgtt tagctatata atgcttgtaa ggctgtatga gcaattataa   113160
gcgtttctaa tctacttaca tgcgattgtg cttaacgtgt ctgtattgac gtgataggta   113220
gctacattta gctgtatgct attgtatagg ttgatgtaga gtaatatact ttgatgtgga   113280
tagcttagtt atactagtcg cttgcttagc ttattcttac atgatactga tattgataca   113340
catctgtaaa cattacagct tatctaattt aatctgaaat acttttcact ttgattagtg   113400
ttgtctacca ccacagttaa gcttatgttt tatttatatg tacacccccta ccccggtta   113460
```

```
atttaccata tagtgcactt taaggtaccc ctattctctc tacctgaggt tccaactaaa  113520
aatatcctga aatttaagtt ttgaatacgg ctaagttgaa cgtgtatata agcgtatgag  113580
tatttcgggt attcctctgg gtaactatgt ctaactatat ctaactacat caaagtatga  113640
ctaacctgag taagtatata agcgtatgag tatttcgggt attcctctgg gtaactatgt  113700
ctaactatat ctaactacat gtcattcgtg ctcctataac ttattatatt aaccaccccc  113760
cccttattta ttttagttta cagtaattag gcatatatga actaccccta ataattccta  113820
aaaaatatat atgtatataa aaaagcatct ataagcttta gatgctctac tgatattaaa  113880
tgtattgtat tattatttac ttgcagatac atacggggct ttttgataac catactcccg  113940
tgtatattct tcatttaatc tataatctaa actcttagag ttatcccagt cgttataagc  114000
ttctaaaatg tcatcttcat ttttaacagt gttatttaga atatcaattg cagattgcgg  114060
agtatctgca caacctagaa tctctaagtc accataatca tctaaatttc gaagtacata  114120
agctacaaac atgatattta cctcctaaat atattattac atagtaaata caacactaat  114180
taatactagc aaactaacag ctaacatacc tttaagaatt ctattgtact ttcgcttttc  114240
tttaatcaaa ctaaccattc ttaacataag taccactcgc tcattatttt catttgaaat  114300 aactaaaatag tatttattac gtttattagg gactgactgt aacttatcct cttcccaaat  114360
agcgtttgct tcatcaagtt catgtataag gtacgtatca actaaaatct taacaacatc  114420
atccttagca ttgttgtcaa cttcatcttt atcgtcaatc ttatcaacat cattgtaagt  114480
tgtggttttt gtgcgagtgt actcagtaaa catattttaa ccaccctaac ctttctttaa  114540
ttgtgatacg taatctttta ccctttttgt gggtttatta atgtagttaa ttgcatcggg  114600
attctgttta actgccgcta accgaatctc ttctgatgaa ttaggataat atacaatatt  114660
gtacccatga tgtttaaccg ctttaagcat atttttcttct ttaatagctc cccggttgat  114720
tcggtcagaa atatgatagt gctcgtcaag cgcttttaca agttcctcac ttttaggaaa  114780
aattaattct ctaactacct ttaggtcact aacggctata ttagagtcat aaccagacct  114840
agctactgta ccccacccctt caacttttgc gacacgaatt ctgcgaaagt catagtaact  114900
aaagcaatct gctaattttg tacaaaagtg catacccgga gttttaacac tgatgttagt  114960
atcttcatga tagcttttgc caacacagta tagtttatca ttgcggtacc aatcatctcc  115020
aaatacttta tacccttaa tactatcttt ttcactaatg gtttccatac tttaacctct  115080
gatttcagtc cttatttta ttagttgtta aggaagatat acttacctga ccttccttaa  115140
tactattaat tatactttct cgtaacttat caaaattttc atctttagtt aaataccaag  115200
gggctttaaa agttaccgtt aaatccaccg tataatcatc ataattatac ttattttccg  115260 cagaaaata ttccttctcc aaatcagaat aaccaataat tagctcttta cccgaatata  115320
ctttattcat taaatagcta ctgtccctaa tagaagcaaa taaagtaaag ccatttacac  115380
ataagttaga aagaatacta atatattcgt cttccaattc cggaatacat tttgattcac  115440
aaaatggcct ataatcttct actccgaata gatgattgac tgcagtatat tcagaagata  115500
aataaccact ataataaaag acatagaaat tgtttgaggt tagtctgcct tccttgatta  115560
aggactggca cactaagtat aaagtacagg taaaattcac cccatcaacc ggtaaatctt  115620
tatcatttgc aacatacata atatattgtg ctacttggtc catagatact ttattcatac  115680
ttactattcc cctctaatta aggtcttttcc atatttaaag ttttaccatg ttccgctacc  115740
tttgcttgaa actccccatc aggtaaggtt ttaatatact tgattagttc cttatattct  115800
ttacgtgtga acttatattc aggtaatact aaatctactt tatcaatcat atcaatatca  115860
```

```
aacggaatgt aagattctgc tttataacag ataactttag aatcgaagcc tttaccacca  115920
ttatcagcaa taataacatt gtattctttt tctcttaaac gttcatcaat cggagtcata  115980
acaaattcat taactaacat ccatagtttg ttactatatg gcaaccggta aaaatcatct  116040
gtatacacca taaaccaata aggtttattc atagacatat tcagtacccg tttattccca  116100
tactttaaga tactattttt acctccgagc atactatcgc tttcctcaaa ggaatattta  116160
ctgcttaact ttttaacttc atcttctagt ttgctatata acattattaa ttacctcttc  116220
cctataagtc taagtccatt cttactagta gaatttaccc ctcatagata ggggctttaa  116280
acttactacg ctcagctaac tctgcaagga gtttaccatt cgttaaagtc ttaatataca  116340
cgattaagtc tttatactca tcgtctgtaa atataaagtc acttaatacc aagtcttctc  116400
cgcaaacttc ttgtaagtaa aaataaaggc cggaagaatt tgactgatga ccccaaacaa  116460
taaaagcatc ctcttcttca gtaactggac taaagataat gttatattta ttagtctcct  116520
gacgttcttc aataggtgtt gcggctagaa gtgccacata cttccaaata tcttcactat  116580
gtggataatc cttaaacttt acagaagctc ttaaatcgta taacctttga gtatcaacgc  116640
aaactaataa accatcccag tgtttagagg tatcatcatc gtcataagta acaataaatg  116700
agtcttcaac tatccgcgca ttatattttt tatcacagtt cttaattgct ttaataacct  116760
cggtatactt cataataaaa catcccttca cttatataat accattacaa atcatatcta  116820
gcaagatata tttaatcaat atcttctaaa tcatcaataa tacctttctt aatatttaat  116880
acggtctgat gtaactcctt ggcactagct tctgggcgtc ccttagtttc ctctgcaatg  116940
ttatataagt agtcttcgat taaatcacgg ataagcaaac ctgcgtcatg caagttatct  117000
aatgcttctt catcttcatc tgtactacca taaaaatcaa cttcaccaac taattattta  117060
accagttctg aaaggctaaa cataattact ttaccccttt ttattattat tgaatgagtt  117120
ctctcggcca tagaataata cccggaccct caaactcttc taacttctct tcaataccaa  117180
agcttccatc aatatcctca acatcgtcag catacctaca aatttcccaa gcctgagaag  117240
atgttagctc ttcacattta gtgtctggct ctgcatcaat gtctgaaata ttttcataat  117300
aatactttac agcttctttt ttatcctttg cggcaattaa tgcatagaag tctgaaccaa  117360
tatctgggga aaatctaaag tatcgttgaa cgattttagc tgtcatcttt ttcattatcc  117420
ttattcttct ttcttttcat tttcttgcaa aaattcaatt aactgttgtc tttcatcagg  117480
ggctaatgta ttatacaatc ccagcacctt atgaaacttc ttatatatat ttttagtatg  117540
cttagaatca ttaatttcat cgcccatatc agagcgtgtt gttaaaaggt aattataccc  117600
attctgatac aatttaatcg ttgcttgacc atttatatca gaattaacag aaagtggctc  117660
aaacacgctc tcagactcat ctaagtatac aactacgata ttgtttggtg attcatactt  117720
tacagatact ttagtttgat aagttgggac atcatcttca aaagcatata aaaccaaata  117780
ccatttatag tcataatttt caatattagt aatatcaatc atctgtttaa tacctctagt  117840
atctctttaa cttataagtt actccaacaa ccttaaactt agattcctct ttatttatct  117900
tgtttaaata attacacatt aattgtgcat catagtaggt aataaaatcc ttacaataaa  117960
atgattcaac tactactctc cctaaagcac acttaacaat attgaacatc taaaatcact  118020
accttattga tgggcttgtt taactacata atctaaatca gtatagctaa ttactaattt  118080
acttgtttct gatttaaacc tagttgattt taatttaatg tcgattaaat ttgctcccat  118140
actattttgc tctaacgtaa aattaataag cttgtgatgt agcttccaca ttagttcctt  118200
```

```
tagtcccaat tgatgagttg tatcatagat attgttaaca gtagcggtgt tgtttagaat  118260
atctaactca atccctagaa cacaaggaaa cttattaacc agctccaaat aagaaacttt  118320
ataactatca ttcaaataat tgactaaagt ttctaagtta actacagagt caaatgataa  118380
ttctttactg cccatttat taccttcctt acgttgttta gtgaaattat taatttcttt  118440
atctgacctt aaagtcttcc tctcaaatga ataaccagct ttagttaaaa cctcttcaat  118500
atctttgtca gaaagttag ctactttatt ttcttcatcg ggaacacaat acatgtcttt  118560
agaaaaatta gccatatgat tatttctcct ttaccttagc atctttgcct atttcatctt  118620
ctccaaataa aacttctttt tcatatagtt ctactaaagg agaaagccta ttagataatt  118680
cttgaaggtc atcccattcg gattgttcat atagttcttt tgtgaacaga gaaccactaa  118740
aacatttttc ataaacacta tctgaacatt tcatactaaa tacccccttta tctagtaacc  118800 attgtccact ttttttcttt aaccaatttt attgatacta ttcattaata tagtcccttta  118860 ttcatatatt tatctagcat aaaatatcct ttcggataat ttcctaccat gcagtttact  118920
ataagctcat aagggactat tcgactattg taaaagtatt taaaatcttt atttactaaa  118980
cgtaaaggac tatctaattt aatataccct ttttaaata tctctttatt actttgatag  119040
tccatatacc taaaatgccg aataatccac caataaaatg agtaattatc ttctatatca  119100
atatccttca ttattattat tattatcccc ctgcattact catagcattc cacttatccc  119160
acatttcagt attttagta atctcatcca attccgggat tctggactca tttatggtat  119220
tactaatact acaatagtgg tacttttcaa ataattctgc ttgaatttta ttaatttctt  119280
cttccatcat ttccgggtcc atagcattag taaactctaa ataattgct tggtgattag  119340 ctttcatatt gtttcctcct ttaataccctt aactatagca catatttaac aaaaagcaat  119400
aaaaaaagag gtaatatccc tcttttatt acatatttag attattaaat ttagacacat  119460
ttccgtaagg cttatgacta accattttag aagttagctt aaccttatct ccaactttag  119520
ataggctgga attaggaaag tcactggtac taattgtgta aatgttgtta ctacctttta  119580
acgaaattaa tacattagag ttacttccat ttgtaataac agccatacgg ttgataactc  119640
cggtagtagt ttctgtcttc acaccattag tgttacctgc accagcatta ccagatacta  119700
aagcatttct aaagctatct aaagcttgtg tagcattgct accactagca ttaattgtct  119760
gattagatgc atctaaatag taatagccac ggaaagcctt agtcttatct aggatggaca  119820
ttacccatac aggtcgtcca ttaatgttat aaataatagg catacttgct ttccattgtt  119880
gggctttata gttctggtta gcattttcta ctgcaccatc actatccata attccctgag  119940
ttttatagaa tgtaagttta ccgtttcgag cattaatcat agaatatcct aaagcactat  120000
ctccaccacc atcacgagta aaatccgtga agtagccaat cgttttatct ttattaaaga  120060
taggtgttac agagctatta gttgaaacca ttacaccgtt attagaaaaa ttccaaaacc  120120
cattcttata cttaccataa gcataattaa tagattcagc tacatccgaa gtaatcccct  120180
catctaccca ttttggcaat ttatcagaag aatacatctt gaatctcct gtatttgcat  120240 tcataacaac cgtgtgtaaa tctttatagt taatccgatg acttagcggc attgacttat  120300
acattgtctc tactaggtaa gggtcgcct tatcgttaat ttctaattgt ggaatactac  120360
tatctgcttt taaccaagta gggtaactct gataaagctt acgagaagct ttcttactaa  120420
accacccact attggcataa gtaatactct tatttacaaa cttaggctga gcatttacat  120480
cagttgcatc aataataaaa tatcccggaa tatgcttagc tttatttgaa gcaaagaatc  120540
catcatattc taatgatgct acatacactg gctttcccg ataatattga gcttcaatat  120600
```

```
cacctaaagt ataatactgg ggattaggta catcactcat agatttattc atacgattac   120660
gagcagtagc atacgtaata gaaaccggtg tttccctcg cttaaaagtg ggggcttcac    120720
tgctattaga cttaatagca gtaatactgc tataaactgg tttaacactc atgtgtgaat   120780
gcaaattacc aacaacgcta gtcaagaaaa caatagctag agttaaccaa agtaatacag   120840
gtagtaattt acttcttttt ttccaactat tacccgcgtt ttttaacaca acaacaccaa   120900
taggaattgt gtaaactaca ttaaggaaca atagacttaa caaatttctc gatggcaacc   120960
caacatagct aaggccataa gcgaatagga aaacaacccc gtataaaata attgaagtaa   121020
gtcctttaat tggctcatta ttaattgaaa gaagaatata aacaatggtg aaaaatagtg   121080
ctaaagctgt tgataaaaac gtaatggtta acataaaaaa tctccttatt taaaaattag   121140
tttgaatttc tggtccatct gtatacatac tatcatctat ttttagtaaa tcaaatataa   121200
atgaataata aggtgtgcta ctaaacatgc cagcaacaaa taacatttta ttagtgtcct   121260
cagaaatata catactcaat cttatcttat aatctgtata atctttctca taaaacttcc   121320
ctctatactc attttttacta aataaatagt cgggcaatac atttgtatta gtatcaaaat   121380
ctctactatc ctctttgtca ggaacatgta tattatatag ctcaccgtca tccaccgcaa   121440
atgaatctac agtataatca cgagtggaac gaacaatggt ctcattatcc ctcaatattc   121500
gagatagtcc taaaatgcac ttagaaacta aatttataca ctcaatagta ttcttcttac   121560
taaattctga aagtctaaag taataggtta ttccagaaga atatatcata tataatatt   121620 ctttataatt attctcatac aacgtacctt ttaaaatatc cttaaagtgt ttacaagctt   121680
taaaatgaat aaaactatta ataatgattc tcttttttata cttaattcta taaaaagaaa   121740
gtatcttttc ttctacatca tacacattat taaaagtttt aatgtagttt ttagtagcca   121800
tcaaattctt ttcattatta atgtatattt tatttaaaaa atcattgact atatagttgc   121860
atgttttgta atctgaatac cttaacatat tttattatcc cctaaactag ctctcaggta   121920
aagcaagctc ttttcctagc ttagcaattc ttactagtga atctccatat ggcatggaat   121980
ctaatttgta aagtaattta ttgaaatcgc tatcagtgaa cttatatctt tcttgactta   122040
aatctgagat aggtactgaa ttatctacga aaaagttacc gttatcatct tttctatagg   122100
caactacaca tatattatgc cctgtgtcta agctttgacc aataactaca ttccatttat   122160
tcttaataat attttccttg acttgatacc ctagcaacct tgcttccgcg aatttatcac   122220
cattgtcttt aatccaatta aaaacatcgg gatacatttc atcaagtcca ttcattctct   122280
gcacagagcg gataacgtca tatccttgct gtttgcaatc cttaatatat tctgaaatat   122340
tttcagggat aacaggtagc aatttgtagt tcttggcaaa gtcctcacta tcaatcaatt   122400
ccgggttatt attaggcgat gtcttaatcc aatcccaac cttaactcta acgtatcctg    122460
attcatcttc atctgatgcc aaaaacacac cagaaacttc ctcagggcca tctggggttt   122520
ggataacttt cactactgct tcagataatc taaactgctt agtcatttca ggacttccat    122580
catattttgt aactgttact ggattattct caatagcttt catttgtgat tacccccttaa   122640 ttagtcggta ttagtatcct gtaaactctc ctcaaattca attaatcggt ccatatattc    122700 tctaccctt tttaaatctt caatcccatt tttattattc tcgcgaaccg tatacttcat    122760
aatattcatc ttcatagcac cccgaaattc ctcatgagtt agaatatctt gtaaatgcca    122820
taataaatca tgttctccat ttttataatg gtctggttca atagcgttat gcccatagct   122880
atctgactta tcacttgaag gcttaccggt tgtaatatca acattaaatg caagatactc   122940
```

```
atcctgtaca cgagcaatta atctatattt tccacttaat cccggctcta aaatacctag   123000
tatatcatcc ttatatataa catgagaatc ctttgtagag gatacccctaa ttacatcaat  123060
attaattaaa taattaataa tattaggtag tccaagaaca tgtttaagag tgatttttt    123120
atccttagcc cattccatag aaagtgttgt tagataagta atattagaat ccgcatcacc   123180
atattgcagt acataaggaa ttaaggattc ccctgttctc tcaatatatg cattattaaa   123240
atcagacggc ttcgtatctc taatactcat aattttataa ctcctttaat taatatcttt   123300
taaatcttct aaaattattt ctttatctga tagtgaacta ttatcataag tatacttaat   123360
gtcatctaat acagattcta attcattatc taattttcgc ttatcttttt gttgcttatt   123420
atatttaata ttccaatcct tatccggact atacttacta taataaactt gcattaccat   123480
atctgcccaa gaatcatgac ccaaattgtc tgttaaaggg aaatttcctt ttctttctag   123540
cttagtatct tctaaataaa tacgtgtagc tgttactttt ttaacctcgc atactccaat   123600
acgttcatag ccattataaa cactgtcgta atcaaatttg tataatttgt ctcctacttt   123660
aatatcttta gctttcatcc tcagtaaccc cctataggta attcaataat atccatttta   123720
tttaggttaa gcacttgtct ataaggcaag ctattaaccg ttttccaaaa taatactgtc   123780
ccttgaccta ccatttctga tacatataat atatgtgact taccatattt atcatagtat   123840
tgccattgtt ggtacatact acagaactca ttccccggtt ctaaaggcca acgatattca   123900
atattatcaa atacactacg aatataagat aagggcctat catcttcttg cttaccaaat   123960
tcgctcaatt cagaatcgcc attagggtgt gctagtaagc cttcaattaa tacttgtgga   124020
tttaattcca gcttattaaa aattcgtttg ttgcgaattt gagggtatac aagcatatta   124080
aatattgact tctgcattct taataaaatat tcatcactaa aatcatgaat tcgattatca   124140
atttcttctg atgtatgcct atatctagcc aattctttca ccactctcta catgtattat   124200
aaacctaatc agattgcatt tcaagttgat acccatttaa ccctgcatta gcaaccaatt   124260
cctgatattt tcgataacga gcataatcaa atttataagt tcccggtgtg agtgccatcc   124320
agtcgcgcat ctgctctggc cgcctctccg agcacagcat gtcaccaatt gatatatgct   124380
tttgtttaca ctcctcaatc cagtcggcaa catatttagg aatcactggt agctgacggt   124440
atctttcatt aaagtctttc tccttaatta aaatgtgttc ttcggcggta cttgatacaa   124500
tccaatcacc aactgtaagc tttataaacc cgcctgtagt tgcaagcaac aaaccactat   124560
ctgtttcgtc atcaacaccc atattaggta ctacgtagtc tgtgcttaac agtctatcaa   124620
ccatccaatt gctaccatca aattgttcag cttcgaatag ttgagtttta tactcttaa    124680
tcatgctgta ccccccaatag tcttttttagt cttcgccaac gcggcttgct ttggttaatt  124740
ggcttgcaaa ataacgtatt aatatgctgt gtcccattca aggccagcca aagttgaaat   124800
ttccatttat ccatgctgtt cctccaatag tccttgcctt ttactaatta ccgtccaatt   124860
ccagttagac acctctttat atttaccaca tttatcacac ataatccgaa caaattcttc   124920
atcccaatcc tcgtctatgt ctgatatgtc cactccacag tgagggactt taaattctcc   124980
aaccttaacg aaatgatgtc ggcaaaataa tttcatttc attccccccaa tagttctgag   125040
ttttccttaa tatttccaac aattttgcaa tctctgataa catcacatag gtctaggcaa   125100
agggattcgc caacaacttt aaactttccc ttttaaaaa taaccttgca taccaaatta   125160
ggagataaac taacaaagtc accctcataa atttccttgc cttcgaagtc tttcatacag   125220
cttgataaat ttgctgaacc ttttcgata gagcaccacc actctgtatt tatatattca   125280
tcagtaatct caattaaatt gccaacaatt gcgtcaacat cattattagg gttgccttta   125340
```

```
acaagattac cgtaaacaaa gtgcccttta tgcggaatat ctacatagcc atcatactca   125400
atatcatcta aattttaat gtatgctcta tacatttatt ttgtctcctt attatgttat    125460
aactaatatt taattacttt cagtctatta gttccaagta caacaaaccc ctcacgttga   125520
gcataatcaa ttacacaagt aatttcaacc aataattctc tgcctaaata ctttccatta  125580
tcatactctc gtaagtcaat aaggtcgcct acttgaaagt tcttgtcatt tttacgaatt  125640
tcaaattcct tatcgccccg catttgtagt cccatgtatt ctggcgcaat ttttagctca   125700
tgtaatgtca taatagttac ctccgattat acagcagatt taacattatc taaaacacct  125760
gtaacgttat tatctttctc ttctgaaagt gataaacaat tattaattaa ttgtgattcc   125820
ttttctgaat gatacttagc gggattctta atggttgtta ctcgaatatc tttaatattc   125880
atattttccc aatcttttgt aactgcccca ccaatatttt tagcgtacgc aatattacgt   125940
ttgatacacc aagcatataa aattttgt tgttcatcag ttaaattatt atcgaaagtt     126000
ccataagctt gtaccaatac attatctggt gaaacttcca aagtaaccca cgaatttcga   126060
ggtgccattc gtgaacgtaa aaatagaata ttagttttc cttcgctaac agaatttaca    126120
taagaaccga cacaattact attattattt ccttcttcaa caatctcttt actacttaca   126180
gcatcaatta agaaataatc ccccaataga gcatcaaact tttcatgatt atgttcccaa   126240
taattaacta ctttgttact agtatctata ttgtctaaaa cagataagtt ctgcataaca   126300
acatcatgtg ttgtctttaa ataacgagga taacggggaa cctttcata atctttagtc    126360 atttgatagt agtctctcaa aatttgtaaa gattctcgaa tagttggaag tccttgctgg   126420
tggtaacaac tagcatatag atagcggaat aaattcttat acgtaacccc cggcgtctcc   126480
aaaacctctc ctagataaga actccattta atgttactct ggtacccact aattaattca   126540
ccgatgtttt cattaatcca gcggtctgca tcatgatacc ctcgttcctt atcaacctga   126600
tgtacggaat catcaaagct ttcaacaagc ttatttaatt cttaatatt catactatca    126660 agacttaaaa tatcatccaa aacgtttcca cttgcttttt taacaatata ttcatagatg   126720 gtttattag ctggtttgat ggcttctcga atactatttc cgtaggtttc agttctatct    126780
acaatattct taacagcact ggcactgata ttattcccac gataattata tagttctta    126840 aaaatcttct caaaagtagg atgtttagcg ataccacgca taatcccacg accgatattt   126900
ctatcttcca ttgagtatgc accatatgct agtcccatgt tgtaaaacat cttaatatta   126960
atgtcatcaa aatatcctga aaaagcttta ccataattaa acaatttatt taaagttgtt   127020
gcatttgctt ttaaacgttt tccagaaact ccttctacaa agaactctcg attgatgagg   127080
tcaataacaa acccatagta gatattactt gtctttccat cccaactctt ttgcttatag   127140
cgtgcaaaac ctgaaaatag tccacggtcc ttagaccaaa acttcaaact atatccatct   127200
gattcaccga ggaagttatc aatagctctt tttttatcct taatagttac tctattcata   127260 tataatcac tactttctag ttgatatact catcttagca tacaggatag aaataatcaa    127320
tgtaaaaaat aaaaaaaaag tccctataac cggacttttt tcatactttt ttatgctgta   127380
attacgtgtg cagacatatc tcgtgtatca atatatagat ataatactcg tttattcgaa   127440
gagttaaatt gcgtaagctg gtctaaatca acagcataga taaaactacc tacagggttt   127500
agtttaagct cataataatc aatatcagtt tttaaagtta atttagtata ttccggatta   127560
gcagttaccg catctacata gaataatcca tctaatgtaa tcttttttgtc taaactaaat  127620 ttaataggg cctgttttga aattttatat ttaaagtcta attcctttaa atactttact    127680
```

```
agtttattag acatgttatt atccccaata aggtatgata gccgttgaaa aatttcgtca    127740
ctttcttctt tactgaaact attttcaggg ttttctgaat cattaggttc ttcaaaaaac    127800
tcccggaatt tctttcgcaa atcatcgtct ttaatattat gtttatctag gatatttgta    127860
atagctagat atacatcttc ttgtacatca tcatctaaat agataacaaa atttgcattt    127920
tttgttacct gaatttcatt gctgttaatg tacacgtctt catcaagaag tttatctcta    127980
atttcttgaa aaacatctgg gaataaatca tttaattcta aaatttcatt attcatattt    128040
tttctcctaa gttttattgg ttaaacacaa caacgccgac attagaatga ttatgactat    128100
caacctcaat atcttgataa attgacaatt tcatatttag cttcttggct aactcccta     128160 agaagttctt atcttgatta agcagtttgc ttactgctag ataattttcc aagtccttat    128220
tgcaagctaa ccaattactt cctaaatact tatctcgtaa tttataagct acggattctg    128280
aaacattttc attatccatg agtaagaatt ttaattcctt gttacctagc aattgattat    128340
gatagtttaa taatgaaaat ttgctcaact tatctgagat tgtcattgtt attacctgct    128400
ttcttagtat atttaaatac tagcatacaa ataatcatat gtaaataaaa aattcccaat    128460
taagggaatt taatgaaata tattaaacat ccgtatcagt attgaagcta atctttttat    128520
cagagggtgt gtctgaacca ctgtcagatt taccctatc ggaatatcca gaatctgact     128580
tagatacatc agattcagaa cttgtagtct ctgctacatc cttagttaaa tcaccatcta    128640
ctgttggtgt ctctgcaaac aattcatcca aatagtcaac aggaacatca ctaatattaa    128700
ggttgatagc attaatagct tcctcaacag taccaaaagt tactacagac tttgtatata    128760
gcttgtttga taagtcttct aacttcataa attctgggaa taccaaattt cccttttgcat   128820 aattaaataa attaaatact tcatctgagg tatccttatt catggcaagg acacgagtaa    128880
ttcctcggaa aacttgccct tttcctgttg ggtcaacccc attaattact aaaatatctc    128940
ctgcatcaaa tgttacttta ctatttgctg tcattgaaaa ttacctccaa tttaatatac    129000
ctatattata ctacttaatc taataagtta caaggtccct atcagggaat atatcttat    129060 ttggattctc tgtagtcgtg gttgttgttg tagttgtggt cgtctgttct ctaattaaac    129120
caatagtaat tacaacatca ctgccatcta ttactttata actactatat ttatctccaa    129180
ttaatcttaa taaagaccct aaacttaggc attgtgtcac aattgactct cctgtcgcaa    129240
tatccactac tgcgtatcct atatccgcag gggttgctat attttcatcc tcatacgttc    129300
ccccagataa atttccatag ggattcttat caaaagtatt ttgattatcc tctgtggttg    129360
tagctacagt tgtggtacta gttgtagtag ttgttgtggt gctatcttct gtgtcatcgc    129420
ctttaggaga agttgataca atccgagcaa gataaattaa ttcaccagat gaactataag    129480
ctaatatata atcacctaca cctatattat ccgtcttttc ataaaaatta tctaacatat    129540
tatttattgt tgccattatt ttcaccacct tcctgtttat taatctaaaa aagagaagga    129600
atttccttct ctttcgtcta gctgtagata actacaaacg taccatcata ttgaaaaact    129660
aaaggctttt cttctgtggg tgtaaactta gcataagttg caatcttact attaacctca    129720
gccgggctac ccccagaaat aaagaatcca ccgtgtgtta agacttcttc tctaatccca    129780
tccagcaata cattagatgt aatccctaaa gtttctttta cttttttctaa atccatatat    129840 ttaaaacttt catctgaaaa cataaataaa tcaccaccttt aaaatgcttt caataatgct   129900
acgcatacta gtaatgtttc ccatatctaa taattttaat cgagtagcta agtatatac     129960 aatagctaga ctaacaaaga ccaaagaatc taaaatatca tcagataatt ctggatactt    130020
gctgaaactg ttaaggtaaa ttgcaatttg tgaagtaaat tccgaataca gggtggatgt    130080
```

```
ctttgcatca attcctacaa acattcctag catttctttt gaaattaaac tgcctttagg  130140
gtctctacca ccactggttt cttttttaat tttaatcata ttgtaggaca caattgcatc  130200
ataagcgtaa gccaaagatt ctaatactac ctctgctgtt tcttcatttt ctgaaatttc  130260
ttttaattta tttaaactag gttcatacga atctgaaagc atagacacgt atccagacaa  130320
ctcgttttta attaaatcac tcattttgtc atttaaacaa agaattgtaa aataattaat  130380
aagctcatta gcgtcatctc gcaaagtatt atcaatatct tctaactcca acatactgat  130440
tctcatatca cgagaaacta ataagtaaat actaggtaaa atgtctgagt aagaataagc  130500
taacagggaa tctaaatttg taaacttcat agaataaaat ttatcactta aactaatatc  130560
ttttgaactg attgtgagcc acccctttat tatcctttaa cctcaaattg ctcttccttg  130620
taggctctag cacgctcttt agcttgttta tacagaatag gataagtcct atcttgcata  130680
tctataatta aagcagtttt ctttttttgca gatacacgaa gcattcgacc aacccgttga  130740
agaagttgtc tgacactttt accagcagaa gcataaatca taaactttaa gtcaggtaca  130800
tctaacccct catcaattag ttgagtacca attaaaacct gagtttctcc tgatttaact  130860
cgcttaataa ttgcttctct atcctcactt gtatctgagg atgtcataaa ttctgtagta  130920
atatctaact tatctaaatg gtctttaata atctcgccat gttcaatact attaacaaca  130980
attatcatgg ctccttcacc agagtctaat aatttcttgg ctgttagagc taacaagtta  131040
ttacgatagc cattttcgat aacaccgtac ctataagcta tttgatagtc cattaaggct  131100
gtctgtcgct tgttagcatc cttaggcatc ttactatcaa taatctcagc taagttatta  131160
ggcttcgtta caggtagtaa tataatggtt ggcttagcag agtaaccttt attaattaag  131220
tcaatatttt tagtaacaat catttcatta ccaaaaatcc cttggaaata tccgtactta  131280
acttcttttc ctgttccatt aggaactgta cctgttaaac caatcttcat tctagcatgg  131340
gttagattac ttacaacttt ttgatacata ttagaagccg cgtggtgggc ttcatcaata  131400
attaaaatct taacaccgtc taaaatattc tttgcttcct catatttatc aaaagacttt  131460
ttattctttt ttcttaataa tttattgtaa gcatctattt cccattgcat agccttagct  131520
attttcttat ctgaaatatt tgatgaaagc atgtctctta aatcactaga gatatttcta  131580
tcatatgaag tcttaggttt attattaagt aagtatgtct taatcctaat acgctgattt  131640
tcacctgtaa caaacttagg tgcaacctct aaagcaaaat gctttaatgt cttatctttt  131700
tcattcgtta gcttaacacc atcactaggg tcttttaagg ccgaattaag cgttccaacc  131760
atagccacgg taacttgttc caattccttc ttaccatcgc cccacaagcc tacaggcatg  131820
tttaaacgct ctgatattct ttttctggat tgattagcaa taactttatt attacacata  131880
aaaaatactt tttcatctga tgctaaagcg tgtaaggatt cttttaataat tgctgatgct  131940
atttcagttt taccactatt agtcgcacca ttaacaaccc cgacctgatg cttgaacgca  132000
aaattaacgg agtcaacctg atgctttcgt agggagatag tccccagctt actatcgggt  132060
aatgtataag gctctggtaa agtttcgtgt tcagggacga ctttatcacc ccttaaatca  132120
ctaatagtca catttagctc tgggtgccta gacttttctt ccttaattaa tttttcaacc  132180
ttaaacatta atccagaaga aaactcttgg gttttagtat tatacattgc gactcttccg  132240
tcccaagcat gtaatctata agctcttgcg ttaaatctat ctgggtcaaa aggacttaga  132300
gtttcataga ttttttttatt catatactca gcaaattcta tagattcatt attatattct  132360
atttttcctt taacattatc taaatcaatt ttcaagaata ctttcctcct cccaaatttt  132420
```

```
agtattgccc tgagaaatga caacttcata tttccctaat tctaatcctg ctacttgcgg   132480
gtcttcatca taaatgattc cctcactaat tttataggca atatctaaag ataaactttt   132540
agaataagga ataatcttat taccttgtac aatatctatg gagtaaatac cttccatcag   132600
caatacaccg cctttttatt ttataacgcc ttatgttaat tataccacat ttaaagcata   132660
gttaacatat tcatttaagt aaaaaaatag agattactag ctctttacat ctagtaacct   132720
ctatttaatg cctgatggaa gaatatcagc aatactctaa tagggaatcg aaccctaatc   132780
aaaagtttag gaaactattg tgctatccat tacaccatta gagtaatatt atatatttat   132840
atatatcatt taaaaaatat tataataact gttgattata acttaattta gtatgatata   132900 gaaccttttta acatattgga ttaccccctt acttgtacat aataacattt ataataagtt   132960
tagtcaataa ttttttaaaat aaaaaaaagg atagttcccc atccttctat gtggggttta   133020
tccttacgag ttccctcgct aattccgcta ctatctataa tatagtaacg tactcagggt   133080
ttttaccatg accctctcaa ccatctaatg ttagcattag attttgggat attccatatt   133140
aggaatcgcc ttttgctttta ttccccacat atatactgac caaggaaaat tgctaattaa   133200
tgtcagttaa caaggaatca tacatcctcg ccttatttac ctaattatcc cgaagttact   133260
taggccattc ctataattta tgtatgctac taatagggga taatatttaa gaataataaa   133320
atgtataaac tctcgacaac ataatatcat ttacttaatt ccatcctact agtagacttt   133380
actatctcaa ccgaggttag accagatagc ttggtttctc tactaaatac tcatcaccat   133440
agggtgatta acatattttt cgactgcgcg cttctcggaa ctcataaaaa ttcgtaatgt   133500
ttaaagagca tagcagtgct cttaaaatac tccctataag acatgataac aataatacta   133560
attacttgat aaacatagct gtaaataatg ataggctaag ggggtcagat aaatctaaag   133620
ggttatacaa actatctttt ggggtgtctt cttttaattc actatcgtgt gaattaaaag   133680
agtgattggg taagtcttcc ttttcattac tattttgtgt ttcactcatt taagtcacca   133740
cctactattt actagtatta aagattgccc agccgtggag tcgaaccatc gtgttcctag   133800
agtcgcgaac ttctaggctt atccgaatct gggcataata tagtgtaggc cacatcataa   133860
tcctacactt gatgagtttt cggtcatcat caagactaac gctaggttat aatgccaccc   133920
gcggggcaat gagcttttct ttcaatcaat attattaatt aatctagcta ctaagaggta   133980
taactctaac cctatcgggg ccaatgctta tcaccgatgt agcccgacaa taaacattat   134040
aggctaaaaa tgttatcaac atataattta atatattata tgttgataac tacggaaagt   134100
acaggacttg aacctgcaat acccagaggg tacaacgagt tagcaacccg cttcaatacc   134160
aattatgatt aactttccaa atttttatact taatacttgg atgacgggag ttgaacccgc   134220
aacagcttga atcacaatca agtgtgcaac cagtagcacc tcatccaaat gccaaaggta   134280
tgattcgaac atactcaccc ttttgagaac ggttttacag accgctgtgg ctcaccatct   134340
ccaccgcttt ggcatattta attatatatt gtaactaacg gacaagacag gactcgaacc   134400
tgcaagtcgc tcacacggcc aactgttttc aggacagcct gctaaccaat tcgcttcttg   134460
cccaaaatat atacttgata gggattcgaa ccctacactt catctagccc taagcaccta   134520
cttctatagt agtgtcgaac tacttcgcag ttagatgtca gattatgata tttctatctt   134580
tagtgtctac acccttccac cacaagcata tgtagttaag catcaactat aggtccgcat   134640
aaaacaggaa aggaaacatt atctccttta atttgttttc ctactacttg atagtctatt   134700
ttactaccgg agacattttc aacccgaatt gcatgaatgc ctgaaatctc tccaaaatcc   134760
aatgataagt tatttaaagt tgcagttacg tgactgttta cttttgtata gcccttatca   134820
```

```
aggtcacgct catcagaaat gttataaata ccttgttgtc cgtactccct cgttacatct    134880
aaactatgag ctatgccaaa tataactccc atatggttaa taacaaatat tgtgttacca    134940
tgacttactg acataataac ctcctaatag tttaagatag tcccggtggt aatcgaaccc    135000
aaaaacattt catctatctc taatccctta cttccattcc ctactatgtg taggtaaatt    135060 atactttta  caccattttc taagtgaatt atctgtcatg ttaaagcctt ttgctgattc    135120
agtaaagtta ccattagtct taattaagga actagtaatt tcttcttttg ttaaaggctt    135180
cttattcttg tatagggaag gacctttttc ctttgcaatc aactttgtag cacatgcttt    135240
acatcttgtg gctttatatg ttattaattt cccacaatct acacaactat gggttcctaa    135300
tgtgttgtga ctgtctacat agttacccat attaaaaata gccatatcaa tagagttttc    135360
tttcgcggta caccattcta aattagatac gttgttattt tctctattat ggtctatatg    135420
attaacttgt ggcaagttat atttattcgg tatgaaagca tttgcaacga gtctatgaac    135480
taatttacca atagatttat tatctctatt tagacctacg ttaacataac catttctatc    135540
ttttgtagta gaaagttttc taccctttat atgcttactc ataccattag aagcggttat    135600
tactctatct aatgaccgga cattaccttt agaagaaact tgataatatc cctcgtatcc    135660
agttatatct ctccactctt ccaaagtaat cgccttctat catcagtttt tattatggtc    135720
ctagaatgtg ctgcccattc gtctcacact tatagggtgt gccctctact gttgagtata    135780
taggaccaat aactgccctg actggactcg gaccagtgac cttcgcatta acagtgcgcc    135840
gttctaccaa ctgaactaca gagcaatgat agcataccct aaaaggacat taatgaaaaa    135900
cagtatgctg acgttttacc ttattgtatt tatgatacaa gcgaataacg agaatcgaac    135960
tcgtatctac agcttggaag gctgtggttt taccactaaa ctatattcgc ataatggggg    136020
atattagtca tcggtcaccg accttgccac caaatataat agttagtggt tacctatcgt    136080
agcaagcctt gatagatatg ctaataccaa aaacgcacta ttacgattat cactgtttaa    136140
gaacatgaat aacataaata atataaataa taag                                136174
```

LACTOBACILLUS BREVIS BACTERIOPHAGE LAC-BRP-1 AND USE THEREOF FOR INHIBITING LACTOBACILLUS BREVIS PROLIFERATION

CROSS-REFERENCE TO RELATED APPLICATIONS

This application is a U.S. National Phase Application of International Application No. PCT/KR2016/000029, filed Jan. 5, 2016, which claims priority to Korean Application No. 10-2015-0013453, filed Jan. 28, 2015, each of which are hereby incorporated by reference in their entirety.

REFERENCE TO SEQUENCE LISTING

The Sequence Listing submitted Jul. 14, 2017, as a text file named "08162_0035_U1 Sequence_Listing.txt," created on Jun. 16, 2017, and having a size of 172,991 bytes is hereby incorporated by reference pursuant to 37 C.F.R. § 1.52(e)(5).

BACKGROUND OF THE INVENTION

1. Field of the Invention

The present invention relates to a bacteriophage isolated from the nature that infects and kills *Lactobacillus brevis* cells, and a method for preventing and treating the contaminations of *Lactobacillus brevis* in a process for producing bio-ethanol by using a composition comprising the bacteriophage as an active ingredient. More particularly, the present invention relates to a Siphoviridae bacteriophage Lac-BRP-1 that is isolated from the nature and can kill *Lactobacillus brevis* cells specifically, which has a genome represented by the nucleotide sequence of SEQ. ID. NO: 1 (Accession NO: KCTC 12659BP), and a method for preventing and treating the contaminations of *Lactobacillus brevis* in a process for producing bio-ethanol by using the composition comprising the bacteriophage as an active ingredient.

2. Description of the Related Art

*Lactobacillus brevis* is a nonmotile Gram-positive bacillus and also referred to as Labre bacteria. *Lactobacillus brevis* is a kind of Lactic Acid Bacteria (LAB) which ferments arabinose, xylose, glucose, fructose, galactose, maltose and the like, to generate lactic acids. In general, it is reported that *Lactobacillus brevis* distributes widely in a human body including intestines, vagina, feces and the like, is often found within fermented food such as sauerkraut and pickles, and proliferate actively at a late period for fermenting cheese and kimchi.

*Lactobacillus brevis* has a feature to resist gastric acids and bile acids more strongly than other bacteria in a human body. Besides, it is a beneficial bacterium to alleviate gingivosis and gastritis effectively due to anti-inflammatory action and to enhance the production of interferons, thereby reinforcing immunity. The sequence analysis of whole *Lactobacillus brevis* genome has been already performed, and thus *Lactobacillus brevis* is being focused on interestingly (PLoS One 8: e60521, 2013).

Unfortunately, *Lactobacillus brevis* is reported to provoke beer spoilage in spite of such beneficial functions and particularly, is a dominant bacterium contaminated in a process for producing bio-ethanol. When this contamination occurs during producing bio-ethanol, *Lactobacillus brevis* could consume indispensible sugars, and thereby reduce the final productivity of bio-ethanol a lot. Moreover, it may generate organic acids in a large scale so as to inhibit the growth of yeast, a bio-ethanol-producing strain, which plays adverse actions in the process for producing bio-ethanol. Therefore, it is urgently requested to develop an effective method for treating the contaminations of *Lactobacillus brevis* in this process.

Nowadays, the advent of the era of high oil prices is expected, due to increased consumption of petroleum and depletion of fossil fuels. Accordingly, it becomes more important to find alternative energy sources world-widely. Bio-ethanol is a potential bio-fuel to reduce the dependence upon petroleum. Bio-ethanol is produced by fermenting starch crops including sugarcane, wheat, corn, potato, barley and the like. In contrast to fossil fuels, bio-ethanol is advantageous not to generate any environment-pollution substances after being used. Besides, it is further advantageous to be applied for transport fuels, compared to other alternative sources. Considering such merits of bio-ethanol, it is required to solve this problem of *Lactobacillus brevis* contaminations in the process for producing bio-ethanol, which could have an industrial significance since influencing directly on the improvement of its productive yield.

Recently, the use of bacteriophages has drawn our attention as a new way of treating bacterial contaminations. Particularly, the reason of our high interest in bacteriophages is because bacteriophage-based treatment is a nature-friendly method.

Bacteriophages are an extremely small microorganism that infects bacteria, which are called phage in short. Once bacteriophage infects bacteria, the bacteriophage is proliferated in the inside of the bacterial cell. After full proliferation, the progenies destroy the bacterial cell wall to escape from the host, suggesting that the bacteriophage has bacteria killing ability. The bacteriophage infection is characterized by high specificity, so that a certain bacteriophage infects only a specific bacterium. That is, the bacterium that can be infected by certain bacteriophage is limited, suggesting that bacteriophage can kill only a specific bacterium and cannot harm other bacteria.

Bacteriophage was first found out by an English bacteriologist Twort in 1915 when he noticed that *Micrococcus* colonies melted and became transparent by something unknown. In 1917, a French bacteriologist d'Herelle found out that *Shigella dysenteriae* in the filtrate of dysentery patient feces melted by something, and further studied about this phenomenon. As a result, he identified bacteriophage independently, and named it as bacteriophage which means a bacteria killer. Since then, bacteriophages specifically acting against such pathogenic bacteria as *Shigella, Salmonella Typhi*, and *Vibrio cholerae* have been continuously identified.

Owing to the unique capability of bacteriophage to kill bacteria, bacteriophages have been studied and anticipated as a method to treat bacterial infections. However, studies on bacteriophages had been only continued in some of Eastern European countries and the former Soviet Union because of the universalization of antibiotics. After the year of 2000, the merit of the conventional antibiotics faded because of the increase of antibiotic-resistant bacteria. So, bacteriophages are once again spotlighted as a new anti-bacterial agent that can replace the conventional antibiotics.

Furthermore, the recent regulation of using antibiotics is fortified by the government world-widely. The interest on bacteriophages is increasing more and also industrial applications are increasily achieved.

Therefore, the present inventors tried to develop a composition applicable for the prevention or treatment of *Lactobacillus brevis* contaminations by using a bacteriophage that is isolated from the nature and can kill *Lactobacillus brevis* cells selectively, and further to establish a method for preventing or treating the contaminations of *Lactobacillus brevis* in a process for producing bio-ethanol by using the composition. As a result, the present inventors isolated bacteriophages suitable for this purpose and secured the nucleotide sequence of the genome that distinguishes the bacteriophage of the present invention from other bacteriophages. Then, we have developed a composition comprising the isolated bacteriophage as an active ingredient, and confirmed that this composition could be efficiently used for the prevention and treatment of *Lactobacillus brevis* contaminations in a process for producing bio-ethanol, leading to the completion of the present invention.

SUMMARY OF THE INVENTION

It is an object of the present invention to provide a Siphoviridae bacteriophage Lac-BRP-1 that is isolated from the nature and can kill specifically *Lactobacillus brevis*, a dominant bacterium contaminated in a process for producing bio-ethanol, which has the genome represented by the nucleotide sequence of SEQ. ID. NO: 1 (Accession NO: KCTC 12659BP).

It is another object of the present invention to provide a composition applicable for the prevention of *Lactobacillus brevis* contaminations, which comprises the isolated bacteriophage Lac-BRP-1 capable of infecting and killing *Lactobacillus brevis*, a dominant bacterium contaminated in a process for producing bio-ethanol, as an active ingredient.

It is another object of the present invention to provide a composition applicable for the treatment of *Lactobacillus brevis* contaminations, which comprises the isolated bacteriophage Lac-BRP-1 capable of infecting and killing *Lactobacillus brevis*, a dominant bacterium contaminated in a process for producing bio-ethanol, as an active ingredient.

It is another object of the present invention to provide a method for preventing the contaminations of *Lactobacillus brevis* by using the composition which comprises the isolated bacteriophage Lac-BRP-1 capable of infecting and killing *Lactobacillus brevis*, a dominant bacterium contaminated in a process for producing bio-ethanol, as an active ingredient, and is applicable for this prevention in a process for producing bio-ethanol.

It is the other object of the present invention to provide a method for treating the contaminations of *Lactobacillus brevis* by using the composition which comprises the isolated bacteriophage Lac-BRP-1 capable of infecting and killing *Lactobacillus brevis*, a dominant bacterium contaminated in a process for producing bio-ethanol, as an active ingredient, and is applicable for this treatment in a process for producing bio-ethanol.

To achieve the above objects, the present invention provides a Siphoviridae bacteriophage Lac-BRP-1 that is isolated from the nature and can kill *Lactobacillus brevis* cells specifically, which has the genome represented by the nucleotide sequence of SEQ. ID. NO: 1 (Accession NO: KCTC 12659BP), and a method for preventing and treating the contaminations of *Lactobacillus brevis* using a composition comprising the bacteriophage as an active ingredient.

The bacteriophage Lac-BRP-1 has been isolated by the present inventors and then deposited at Korean Collection for Type Cultures, Korea Research Institute of Bioscience and Biotechnology in Aug. 21, 2014 (Accession NO: KCTC 12659BP).

The present invention also provides a composition applicable for the prevention or the treatment of *Lactobacillus brevis* contaminations, which comprises the bacteriophage Lac-BRP-1 used to prevent and treat the contaminations of *Lactobacillus brevis* in a process for producing bio-ethanol, as an active ingredient.

Since the bacteriophage Lac-BRP-1 included in the composition of the present invention kills *Lactobacillus brevis* cells efficiently, it is regarded as effective to prevent or treat the contaminations of *Lactobacillus brevis*. Therefore, the composition of the present invention can be utilized in order to prevent and treat the contaminations of *Lactobacillus brevis* in a process for producing bio-ethanol.

In this specification, the term "treatment" or "treat" indicates (i) to inhibit the growth of *Lactobacillus brevis* contaminated in a process for producing bio-ethanol effectively; and (ii) to reduce *Lactobacillus brevis* contaminated in a process for producing bio-ethanol.

In this description, the term "isolation" or "isolated" indicates all the actions to separate the bacteriophage by using diverse experimental techniques and to secure the characteristics that can distinguish this bacteriophage from others, and further includes the action of proliferating the bacteriophage via bioengineering techniques so as to make it useful.

In one embodiment, the composition of the present invention can be realized in a stable form comprising the bacteriophage without any limitation. For example, it can be prepared in a liquid or solid form and the solid form can be prepared in various forms such as powder, pellet or the like. But it should not be limited to.

The composition of the present invention can further comprise various ingredients in order to improve the stability or the activity of the bacteriophage. Particularly, the composition of the present invention can comprise various salts, pH buffering agents, stabilizers, detergents, wetting agents, emulsifiers, suspending agents, preservatives etc., but not limited to.

In the composition of the present invention, the bacteriophage Lac-BRP-1 is included as an active ingredient. At this time, the bacteriophage Lac-BRP-1 is included at the concentration of $1 \times 10^1$ pfu/ml~$1 \times 10^{30}$ pfu/ml or $1 \times 10^1$ pfu/g~$1 \times 10^{30}$ pfu/g, and preferably at the concentration of $1 \times 10^4$ pfu/ml~$1 \times 10^{15}$ pfu/ml or $1 \times 10^4$ pfu/g~$1 \times 10^{15}$ pfu/g.

The composition of the present invention can be formulated by the method that could be performed easily by those in the art by using a carrier and/or excipient acceptable in the art, in the form of unit dose or in a multi-dose container.

The composition of the present invention can be added and used in a process for producing bio-ethanol according to application modes, but not limited to. It can be used in any procedure adopted from pre-treatment of raw material, liquefaction, glycosylation and fermentation, and preferably fermentation, in the process for producing bio-ethanol.

The composition of the present invention or the method for prevent and treat the contaminations of *Lactobacillus brevis* can be applied for any process for producing bio-ethanol regardless of using sugarcane, corn, girasol, plants and the like as raw material.

Advantageous Effect

The composition comprising the bacteriophage Lac-BRP-1 of the present invention as an active ingredient can be used to prevent and treat the contaminations of *Lactobacillus brevis* in a process for producing bio-ethanol, which prevents loss of sugars caused by the contaminations and thereby increases the productive yield of bio-ethanol.

In addition, the method for prevent and treat the contaminations of *Lactobacillus brevis* in a process for producing bio-ethanol by using the composition comprising the bacteriophage Lac-BRP-1 of the present invention as an active ingredient, is advantageous to be nature-friendly, compared with the conventional methods based on chemical material including conventional antibiotics etc. When exploiting the conventional methods, the chemical material such as conventional antibiotics could remain within byproducts through the procedure, so that the application of products for feeds of livestock, fertilizers or the like could be restricted. However, the method of the present invention using the composition comprising the bacteriophage Lac-BRP-1 as an active ingredient, facilitates the application of products for feeds of livestock, fertilizers or the like without any limitation. In the meantime, the occurrence of antibiotics-resistant bacteria is increasing recently so as to reduce the effectiveness of antibiotics continuously in those conventional methods. The composition of the present invention and the method of the present invention are expected to settle such a problem of antibiotic resistance simply, because the bacteriophage Lac-BRP-1 included as an active ingredient in the composition of the present invention gives the antibiotic efficacy against *Lactobacillus brevis* regardless of the presence of antibiotic resistances.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
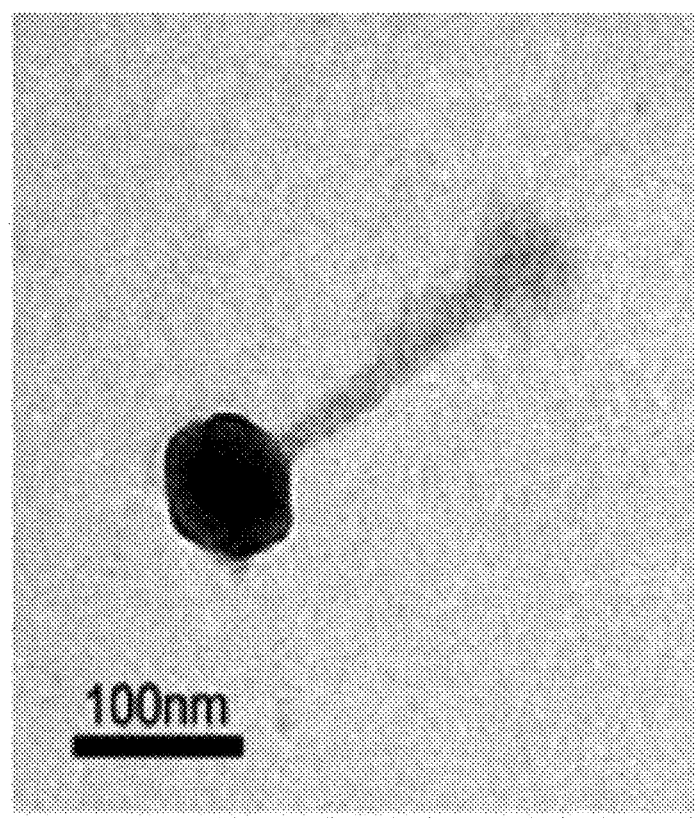
FIG. 1 is an electron micrograph showing the morphology of the bacteriophage Lac-BRP-1.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Isolation of Bacteriophage Capable of Killing *Lactobacillus brevis*

Samples were collected from the nature to screen the bacteriophage capable of killing *Lactobacillus brevis*. The *Lactobacillus brevis* used for the bacteriophage isolation herein were the one that had been isolated by the present inventors and identified as *Lactobacillus brevis* previously.

The isolation procedure of the bacteriophage is described in detail hereinafter. The collected sample was added to the MRS (deMan Rogosa and Sharpe Broth) medium (proteose peptone NO: 3, 10 g/L; beef extract, g/L; yeast extract, 5 g/L; dextrose, 20 g/L; polysorbate 80, 1 g/L; ammonium acetate, 2 g/L; sodium acetate, 5 g/L; magnesium sulfate, 0.1 g/L; manganese sulfate, 0.05 g/L; dipotassium phosphate, 2 g/L) inoculated with *Lactobacillus brevis* at the ratio of 1/100, followed by standing culture at 30° C. for 3~4 hours. Upon completion of the culture, centrifugation was performed at 8,000 rpm for 20 minutes and supernatant was recovered. The recovered supernatant was inoculated with *Lactobacillus brevis* at the ratio of 1/100, followed by standing culture at 30° C. for 3~4 hours. When the sample contained the bacteriophage, the above procedure was repeated total 5 times in order to increase the titer of the bacteriophage. After repeating the procedure 5 times, the culture solution proceeded to centrifugation at 8,000 rpm for minutes and the resulting supernatant was recovered. The recovered supernatant was filtrated by using a 0.45 µm filter. The obtained filtrate was used in spot assay for examining whether or not the bacteriophage capable of killing *Lactobacillus brevis* was included therein.

Spot assay was performed as follows; MRS medium was inoculated with *Lactobacillus brevis* at the ratio of 1/100, followed by standing culture at 30° C. for overnight. 3 ml (2.0 of $OD_{600}$) of the culture broth of *Lactobacillus brevis* prepared above was spread on the MRS-A (deMan Rogosa and Sharpe Agar) medium (proteose peptone NO: 3, 10 g/L; beef extract, 10 g/L; yeast extract, 5 g/L; dextrose, 20 g/L; polysorbate 80, 1 g/L; ammonium acetate, 2 g/L; sodium acetate, 5 g/L; magnesium sulfate, 0.1 g/L; manganese sulfate, 0.05 g/L; dipotasium phosphate, 2 g/L; agar, 15 g/L) plate. The plate stood in a chamber for about 30 minutes to dry. After drying, 10 µl of the resulting filtrate was spotted directly onto the surface of the *Lactobacillus brevis* lawns and dried for about 30 minutes. Following drying, the plate was incubated at 30° C. for a day and then, examined for the formation of clear zones on the surface of the bacterial lawns. If a clear zone was generated where the filtrate was dropped, it could be judged that the bacteriophage capable of killing *Lactobacillus brevis* was included in the filtrate. Through the above procedure, the filtrate containing the bacteriophage having the killing ability of *Lactobacillus brevis* could be obtained.

After that, the bacteriophage was isolated from the filtrate confirmed above to have the bacteriophage capable of killing *Lactobacillus brevis*. The conventional plaque assay was used for the isolation of pure bacteriophages. In detail, a plaque formed in the course of the plaque assay was picked up by using a sterilized tip, which was then added to the culture solution of *Lactobacillus brevis*, followed by standing culture at 30° C. for 4~5 hours. Upon completion of the culture, centrifugation was performed at 8,000 rpm for 20 minutes to obtain supernatant. The recovered supernatant was inoculated with *Lactobacillus brevis* culture at the ratio of 1/50, followed by standing culture again at 30° C. for 4~5 hours. To increase the titer of the bacteriophage, the above procedure was repeated at least 5 times. Then, centrifugation was performed at 8,000 rpm for 20 minutes to obtain supernatant. Plaque assay was performed with the obtained supernatant. In general, the pure bacteriophage isolation is not completed by one-time procedure, so the above procedure was repeated by using the plaque formed above. After at least 5 times of repeated procedure, the solution containing the pure bacteriophage was obtained. The procedure for the isolation of the pure bacteriophage was generally repeated until the generated plaques became similar in sizes and morphologies. And the final pure bacteriophage isolation was confirmed by the observation under electron microscope. Until the pure bacteriophage isolation was confirmed under electron microscope, the above procedure was repeated. The observation under electron microscope was performed by the conventional method. Briefly, the solution containing the pure bacteriophage was loaded on copper grid, followed by negative staining with 2% uranyl acetate. After drying thereof, the morphology was observed under transmission electron microscope. The electron micrograph of the bacteriophage isolated in the present invention is presented in FIG. 1. From the morphological observation, the bacteriophage isolated above was identified as belonging to the family Siphoviridae.

The solution containing the pure bacteriophage confirmed above proceeded to purification. The culture broth of *Lactobacillus brevis* was added to the solution containing the pure bacteriophage at the volume of 1/50 of the total volume of the bacteriophage solution, followed by culturing again for 4~5 hours. Upon completion of the culture, centrifugation was performed at 8,000 rpm for 20 minutes to obtain supernatant. This procedure was repeated 5 times to obtain a solution containing enough numbers of the bacteriophage. The supernatant obtained from the final centrifugation was filtered by a 0.45 μm filter, followed by the conventional polyethylene glycol (PEG) precipitation. Particularly, PEG and NaCl were added to 100 ml of the filtrate until reaching 10% PEG 8000/0.5 M NaCl, which stood at 4° C. for 2~3 hours. Then, centrifugation was performed at 8,000 rpm for 30 minutes to obtain the bacteriophage precipitate. The resulting bacteriophage precipitate was resuspended in 5 ml of buffer (10 mM Tris-HCl, 10 mM $MgSO_4$, 0.1% Gelatin, pH 8.0). This solution was called as the bacteriophage suspension or bacteriophage solution.

As a result, the pure bacteriophage purified above was collected, which was named as the bacteriophage Lac-BRP-1 and then deposited at Korean Collection for Type Cultures, Korea Research Institute of Bioscience and Biotechnology in Aug. 21, 2014 (Accession NO: KCTC 12659BP).

Example 2: Separation and Sequence Analysis of the Bacteriophage Lac-BRP-1 Genome The genome of the bacteriophage Lac-BRP-1 was separated as follows. The genome was separated from the bacteriophage suspension obtained in Example 1. First, in order to eliminate DNA and RNA of *Lactobacillus brevis* included in the suspension, DNase I and RNase A were added 200 U each to 10 ml of the bacteriophage suspension, which was incubated at 37° C. for 30 minutes. 30 minutes later, to remove the DNase I and RNase A activity, 500 μl of 0.5 M ethylenediaminetetraacetic acid (EDTA) was added thereto, which was incubated for 10 minutes. The suspension was further incubated at 65° C. for 10 minutes and then added with 100 μl of proteinase K (20 mg/ml) to break the outer wall of the bacteriophage, followed by incubation at 37° C. for 20 minutes. After that, 500 μl of 10% sodium dodecyl sulfate (SDS) solution was added thereto, followed by incubation at 65° C. for 1 hour. 10 ml of the mixture of phenol:chloroform:isoamylalcohol in a ratio of 25:24:1 was added thereto, followed by mixing well. The mixture was centrifuged at 13,000 rpm for 15 minutes to separate each layer. The upper layer was obtained, to which isopropyl alcohol was added at the volume of 1.5 times the volume of the upper layer, followed by centrifugation at 13,000 rpm for 10 minutes to precipitate the genome of the bacteriophage. After collecting the precipitate, 70% ethanol was added to the precipitate, followed by centrifugation at 13,000 rpm for 10 minutes to wash the precipitate. The washed precipitate was recovered, vacuum-dried and then dissolved in 100 μl of water. This procedure was repeated to obtain a sufficient amount of the bacteriophage Lac-BRP-1 genome.

The nucleotide sequence of the genome of the bacteriophage Lac-BRP-1 obtained above was analyzed by Next Generation Sequencing (NGS) using illumina Mi-Seq device at National Instrumentation Center for Environmental Management, Seoul National University. As a result, it is suggested that the final genome of bacteriophage Lac-BRP-1 have 136,174 bp of size and the nucleotide sequence of the whole genome has SEQ. ID. NO: 1.

Similarity of the genomic sequence of the bacteriophage Lac-BRP-1 obtained above with the previously reported bacteriophage genome sequences was investigated by using BLAST. From the BLAST result, it is noted that genomic sequences having more than 50% homology with the genomic sequence of bacteriophage Lac-BRP-1 were not found.

Based upon this result, it is concluded that the bacteriophage Lac-BRP-1 should be a novel bacteriophage not reported previously.

Example 3: Investigation of Killing Ability of the Bacteriophage Lac-BRP-1 Against *Lactobacillus brevis*

Figure 2:
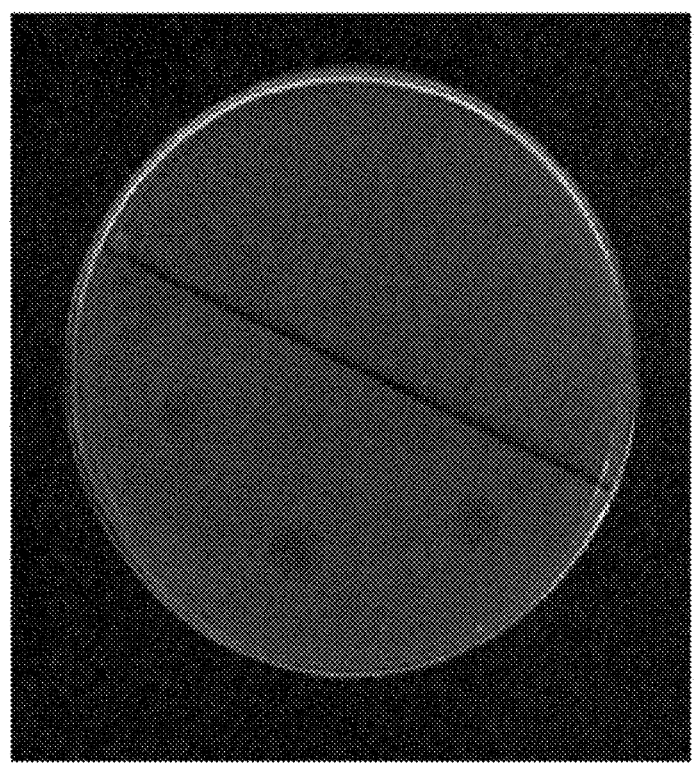
FIG. 2 is a photograph illustrating the capability of the bacteriophage Lac-BRP-1 to kill *Lactobacillus brevis*. The clear zone on the dish is the formation of plaque by lysis of bacteria cells.

The killing ability of the isolated bacteriophage Lac-BRP-1 against *Lactobacillus brevis* was investigated. To do so, the formation of clear zone was observed by the spot assay by the same manner as described in Example 1. The *Lactobacillus brevis* used for this investigation were total 15 strains which had been isolated and identified as *Lactobacillus brevis* previously by the present inventors. The bacteriophage Lac-BRP-1 demonstrated the killing ability against 11 strains of the *Lactobacillus brevis* used in this experiment. The representative result of the killing ability test is shown in FIG. 2. In the meantime, the activity of the bacteriophage Lac-BRP-1 to kill *Staphylococcus aureus, Enterococcus faecalis, Enterococcus faecium, Streptococcus agalactiae, Streptococcus uberis, Haemophilus parasuis, Bordetella bronchiseptica*, and *Escherichia coli* was also investigated. As a result, it is decided that the bacteriophage Lac-BRP-1 did not have the killing activity against these microorganisms.

Therefore, it is confirmed that the bacteriophage Lac-BRP-1 had the specific killing ability against *Lactobacillus brevis* and a broad antibacterial spectrum against *Lactobacillus brevis*, suggesting that the bacteriophage Lac-BRP-1 of the present invention could be used as an active ingredient for the composition for preventing and treating the contaminations of *Lactobacillus brevis*.

Example 4: Preventive Effect of Bacteriophage Lac-BRP-1 on the Contaminations of *Lactobacillus brevis*

The bacteriophage Lac-BRP-1 was investigated under a similar bio-ethanol-producing condition whether it could be used to prevent the contaminations of *Lactobacillus brevis* or not. 100 mL of molasses medium (16% total sugars, 0.046% $KH_2PO_4$, 0.225% urea) was added to 4 of 300 mL erlenmeyer flasks respectively. Then, the bacteriophage Lac-BRP-1 suspension prepared by the same manner as described in Example 1 was added to only 2 flasks to adjust the concentration of bacteriophage at $1 \times 10^6$ pfu/mL, while the other 2 flasks remained intact. After that, *Lactobacillus brevis* cells were added to all flasks to reach $1 \times 10^4$ cfu/mL. The resulting solutions were cultivated at 30° C. for 16 hours. Then, 100 μL of the solution was collected from each flask, ten-fold serially diluted in physiological saline solution, spread onto MRS-A medium plates respectively and then cultivated at 30° C. in a plate incubator for overnight. Upon completion of overnight culture, the number of colonies formed was counted. Then, based upon the count of colonies, the concentration of *Lactobacillus brevis* was calculated in each flask. The results are as follows.

TABLE 1

Suppresion of *Lactobacillus brevis* contamination

| Item | Concentration of *Lactobacillus brevis* cells |
|---|---|
| Flask 1 (− bacteriophage solution) | approximately $10^6$ cfu/mL |
| Flask 2 (− bacteriophage solution) | approximately $10^8$ cfu/mL |
| Flask 1 (+ bacteriophage solution) | approximately $10^2$ cfu/mL |
| Flask 2 (+ bacteriophage solution) | approximately $10^2$ cfu/mL |

The above results indicate that the bacteriophage Lac-BRP-1 not only inhibited the growth of *Lactobacillus brevis* but also could kill them. Therefore, it is concluded that the bacteriophage Lac-BRP-1 could be used as an active ingredient of the composition in order to prevent the contaminations of *Lactobacillus brevis*.

Example 5: Effect of the Treatment with Bacteriophage Lac-BRP-1 on the Contaminations of *Lactobacillus brevis*

The bacteriophage Lac-BRP-1 was investigated under a similar bio-ethanol-producing condition whether it could be used to treat the contaminations of *Lactobacillus brevis* or not. 100 mL of molasses medium was added to 4 of 300 mL erlenmeyer flasks respectively and inoculated with yeast cells to reach $5 \times 10^7$ cfu/mL. Then, *Lactobacillus brevis* ($1 \times 10^4$ cfu/mL) was innocuated to all erlenmeyer flasks. After innoculation, the bacteriophage Lac-BRP-1 suspension prepared by the same manner as described in Example 1 was added to only 2 flasks to adjust the concentration of bacteriophage at $1 \times 10^7$ pfu/mL, while the other 2 flasks remained intact. The resulting solutions were cultivated at 30° C. for 24 hours. Then, 100 μL of the solution was collected from each flask, ten-fold serially diluted in physiological saline solution and spread onto MRS-A medium plates respectively. The resulting plates were cultivated at 30° C. in a plate incubator for 24 hours. Upon completion of overnight culture, the number of colonies formed was counted. Then, based upon the count of colonies, the concentration of *Lactobacillus brevis* was calculated in each flask. The results are as follows.

TABLE 2

Treatment of *Lactobacillus brevis* contamination

| Item | Concentration of *Lactobacillus brevis* |
|---|---|
| Flask 1 (− bacteriophage solution) | approximately $10^8$ cfu/mL |
| Flask 2 (− bacteriophage solution) | approximately $10^8$ cfu/mL |

TABLE 2-continued

Treatment of *Lactobacillus brevis* contamination

| Item | Concentration of *Lactobacillus brevis* |
|---|---|
| Flask 1 (+ bacteriophage solution) | approximately $10^1$ cfu/mL |
| Flask 2 (+ bacteriophage solution) | Not detected |

From the above results, it is concluded that the bacteriophage Lac-BRP-1 of the present invention could be used as an active ingredient of the composition in order to treat the contaminations of *Lactobacillus brevis*.

Example 6: Application Tests

The bacteriophage Lac-BRP-1 was investigated practically in the process for producing bio-ethanol whether it could be applied to improve the productive yield of bio-ethanol or not. For this application, the bacteriophage Lac-BRP-1 suspension prepared by the same manner as described in Example 1 was utilized. The application tests were performed by adding bacteriophage suspension to a yeast cream to be the bacteriophage concentration of $1 \times 10^7$ pfu/mL (test ①), putting bacteriophage suspension into a fermentation tank to be the bacteriophage concentration of $1 \times 10^6$ pfu/mL (test ②), putting bacteriophage suspension into a fermentation tank to be the bacteriophage concentration of $1 \times 10^6$ pfu/mL along with the bacteriophage suspension added to a yeast cream to be the bacteriophage concentration of $1 \times 10^7$ pfu/mL (test ③), and without any treatment (test ④). Test ④ was included as a control group. These application tests were conducted total 10 times and the results are as follows. In Table 3, the bio-ethanol productivity is average values obtained after measuring 10 times and considering that of test ④ as 100%.

TABLE 3

Results of application tests

| Item | Productivity of bio-ethanol |
|---|---|
| Test ① | 104% |
| Test ② | 106% |
| Test ③ | 107% |
| Test ④ | 100% |

From the above results, it is confirmed that the composition of the present invention comprising the bacteriophage Lac-BRP-1 could be effective to improve the productive yield of bio-ethanol.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for treating contaminations of *Lactobacillus brevis*, the method comprising a step of adding a composition comprising Siphoviridae bacteriophage Lac-BRP-1 that is isolated from nature and can kill *Lactobacillus brevis* cells specifically, which has the genome represented by the nucleotide sequence of SEQ ID NO: 1, as an active ingredient.

2. The method according to claim 1, wherein said composition is added to treat the contaminations of *Lactobacillus brevis* in a process for producing bio-ethanol.

* * * * *